United States Patent [19]

Tessier-Lavigne et al.

[11] Patent Number: 5,565,331
[45] Date of Patent: Oct. 15, 1996

[54] NUCLEIC ACIDS ENCODING NEURAL AXON OUTGROWTH MODULATORS

[75] Inventors: Marc Tessier-Lavigne; Tito Serafini; Timothy Kennedy, all of San Francisco, Calif.; Merysia Placzek, London, England; Thomas Jessell; Jane Dodd, both of New York, N.Y.

[73] Assignee: The Regents of the University of California, Oakland, Calif.

[21] Appl. No.: 152,019

[22] Filed: Nov. 12, 1993

[51] Int. Cl.$^6$ .......................... C12N 15/00; C12N 15/12; C12N 5/10
[52] U.S. Cl. .......................... 435/69.1; 435/6; 435/240.2; 435/320.1; 536/23.5
[58] Field of Search .................. 536/23.5; 435/240.2, 435/320.1, 69.1, 6

[56] References Cited

PUBLICATIONS

Gunderson and Barrett, "Characterization of the Turning Response of Dorsal Root Neurites toward Nerve Growth Factor", *J. of Cell Biology* 87:546–554 (1980).

Ishii et al., "UNC–6, a Laminin–Related Protein, Guides cell and Pioneer Axon Migrations in C. elegans", *Neuron* 9:873–881 (1992).

Lohof et al., "Asymmetric Modulation of Cytosolic cAMP Activity Induces Growth Cone Turning", *J. of Neuroscience* 12(4):1253–1261 (1992).

Placzek et al., "Guidance of Developing Axons by Diffusible Chemoattractants", *Cold Spring Harbor Symposia on Quantitative Biology* LV:279–289 (1990).

Placzek et al., "Orientation of Commissural Axons in vitro in Response to a Floor Plate–derived Chemoattractant", *Development* 110:19–30 (1990).

Tessier–Lavigne et al., "Chemotropic Guidance of Developing Axons in the Mammalian Central Nervous Systems", *Nature* 336(6201):775–778 (1988).

Zheng et al., "Chemotaxis of Growth Cone of Xenopus Spinal Neuron in a Gradient of Acetylcholine", *Society for Neuroscience Abstracts* 19:1481 (1993), abstract.

Zheng et al., "Turing of Nerve Growth Cones Induced by Neurotransmitters", *Nature* 368:140–144 (1994).

Klar, A. et al., *Cell*, 69:95–110, 1992.

*Primary Examiner*—Marianne P. Allen
*Attorney, Agent, or Firm*—Richard Aron Osman

[57] ABSTRACT

A novel classes of neural axon outgrowth promoting and orienting proteins, nucleic acids encoding such proteins and receptors which selectively bind such proteins are disclosed. The disclosed neural axon outgrowth promoting and orienting proteins include the laminin-related p75/p78 family; a family of vertebrate proteins which promote axon outgrowth and/or orientation, and p75/p78 family-specific receptors, including receptors found on spinal nerve axons, especially growth cones. Also disclosed are agents including peptides derived from the disclosed neural axon outgrowth promoting proteins capable of effecting axon outgrowth, orientation and regeneration. These agents provide small molecular weight modulators of nerve cell growth useful in the treatment of neurological disease and injury. The disclosed compositions also find use variously in screening chemical libraries for regulators of axon outgrowth and orientation, in genetic mapping, as probes for related genes, as diagnostic reagents for genetic neurological disease and in the production of specific cellular and animal systems for the development of neurological disease therapy.

9 Claims, 50 Drawing Sheets

FIG. 4 p78 aa Sequence

```
           10         20         30         40         50
  1234567890 1234567890 1234567890 1234567890 1234567890
  MPRRGAEGPL ALLLAAAWLA QPLRGGYPXL NMFAVQIXAD PCYDEHGLPX    50
  RCIPDFVNSA FGKEVKVSST CGKPPSRYCV VTEKGEEQVR SCHLCNASDP   100
  KRAHPPSFLT DLNNPHNLTC WQSDSYVQYP HNVTLTLSLG KKFEVTYVSL   150
  QFCSPRPESM AIYKSMDYGK TWVPFQFYST QCRKMYNKPS RAAITKQNEQ   200
  EAICTDSHTD VRPLSGGLIA FSTLDGRPTA HDFDNSPVLQ DWVTATDIKV   250
  TFSRLHIFGD ENEDDSELAR DSYFYAVSDL QVGGRCKCNG HASRCVRDRD   300
  DNLVCDCKHN TAGPECDRCK PFHYDRPWQR ATAREANECV ACNCNLHARR   350
  CRFNMELYKL SGRKSGGVCL NCRHNTAGRH CHYCKEGFYR DLSKPISHRK   400
  ACKECDCHPV GAAGQTCNQT TGQCPCKDGV TGITCNRCAK GYQQSRSPIA   450
  PCIKIPAAPP PTAASSTEEP ADCDSYCKAS KGKLKINMKK YCKKDYAVQI   500
  HILKAEKNAD WWKFTVNIIS VYKQGSNRLR RGDQTLWVHA KDIACKCPKV   550
  KPMKKYLLLG STEDSPDQSG IIADKSSLVI QWRDIWARRL RKFQQREKKG   600
  KCRKA                                                    605
```

Fig. 5 p75 aa Sequence

|  | 10 | 20 | 30 | 40 | 50 |  |
|---|---|---|---|---|---|---|
|  | 1234567890 | 1234567890 | 1234567890 | 1234567890 | 1234567890 |  |
|  | LRLLLTTSVL | RLARAANPFV | AQQTPPDPCY | DESGAPPRCI | PEFVNAAFGK | 50 |
|  | EVQASSTCGK | PPTRHCDASD | PRRAHPPAYL | TDLNTAANMT | CWRSETLHHL | 100 |
|  | PHNVILTLSL | GKKFEVVYVS | LQFCSPRPES | TAIFKSMDYG | KTWVPYQYYS | 150 |
|  | SQCRKTYGKP | SKATVTKQNE | QEALCTDGLT | DLYPLTGGLI | AFSTLDGRPS | 200 |
|  | AQDFDSSPVL | QDWVTAIDIR | VVFSRPHLFR | ELGGREAGEE | DGGAGATPYY | 250 |
|  | YSVGELQVGG | RCKCNGHASR | CVKDKEQKLV | CDCKHNTEGP | ECDRCKPFHY | 300 |
|  | DRPWQRASAR | EANECLACNC | NLHARRCRFN | MELYKLSGRK | SGGVCLNCRH | 350 |
|  | NTAGRHCHYC | KEGFYRDLSK | STTDRKACKA | CDCHPVGAAG | KTCNQTTGQC | 400 |
|  | PCKDGVTGLT | CNRCAKGFQQ | SRSPVAPCIK | IPAINPTSLV | TSTEAPADCD | 450 |
|  | SYCKPAKGNY | KINMKKYCKK | DYVVQVNILE | METVANWAKF | TINILSVYKC | 500 |
|  | RDERVKRGDN | FLWIHLKDLS | CKCPKIQISK | KYLVMGISEN | STDRPGLMAD | 550 |
|  | KNSLVIQWRD | AWTRRLRKLQ | RREKKGKCVK | P |  | 581 |

Fig. 6 p75 & p78 Formatted Alignment

```
p78 aa con  MPRRGAEGPL ALITAAAWLA QHFRGGYPXL NMFAVQTXAD PCYDEHGLPX      50
p75 aa con  ---------- ---RLLITT SVMRLARAAN PFVAQQIPPD PCYDESGAPP      37 p78 aa con  RCIHFVNSA FGKEMKVSST CGKPPSRMCV VIEKGEEQVR SCHIQNASDP      100
p75 aa con  RCIHFVNAA FGKEMQASST CGKPPIRHC- --------- -----DASDP       71 p78 aa con  KRAHPESHLT DINNPHNIIC WSDSYVQYP HNVILTLSIG KKFEVIYVSL       150
p75 aa con  FRAHPPAVLT DINTAANMC WFSEILHHIP HNVILTLSIG KKFEVVVSL        121 p78 aa con  QFCSPRPESM AIMKSMDYGK TWVFQFYST QCRKMVNKPS RAAIIKQNEQ        200
p75 aa con  QFCSPRPEST AIFKSMDYGK TWVFQMYSS QCRKIHYGKPS KATVIKQNEQ       171 p78 aa con  EAICIDSHID VRPLGGLIA FSTLDGRPIA HDFDNSPVLQ DWTATDIKV         250
p75 aa con  EAICIGIID LMPLIGGLIA FSTLDGRPSA QDFDSSPVLQ DWTATDIRV         221 p78 aa con  TFSRLHIFGD -----ENED SELARDSYFY AVSDIQVGGR CKCNGHASRC       295
p75 aa con  VFSRHLFRE LGGREAGEED GGAGATIYMY SVGELQVGER CKCNGHASRC       271
```

Fig. 7a p75 & p78 Formatted Alignment

```
p78 aa con  VHDRDNLVC DCKHNIAGPE CLRCKPFHYD RPWQRAIARE ANECVACNCN  345
p75 aa con  VKDKEQKLVC DCKHNIEGPE CLRCKPFHYD RPWQRASARE ANECLACNCN  321 p78 aa con  LHARRCRFMM ELYKLSGRKS GGVCLNCRHN TAGRHCHYCK EGFYRDLSKP  395
p75 aa con  LHARRCRFMM ELYKLSGRKS GGVCLNCRHN TAGRHCHYCK EGFYRDLSKS  371 p78 aa con  TSHRKACKEC DCHPVGAAGQ TCNQTTGQCP CKDGVIGITC NRCAKGYQQS  445
p75 aa con  ITTRKACKAC DCHPVGAAGK TCNQTTGQCP CKDGVIGITC NRCAKGFQQS  421 p78 aa con  RSFIAPCIKI PAAPPTAAS STFEPADCDS YCKASKGKLK INMKYCCKD    495
p75 aa con  RSFMAPCIKI PAINFTSLVT STFEAPADCDS YCKPAKGNMK INMKYCCKD   471 p78 aa con  YAVQIHILKA EKNAIMWKFT WNIILSVYKCG SNRLRRGDDT LWHAKDIAC   545
p75 aa con  WVQVNIIEM ETVANWAKFT INILSVYKCR DERVKRGENF LWHILKDLSC  521 p78 aa con  KCPKVKPMKK YILIGSTETIS FDSGITADK SSLVIQMRDT MARRLRLRKEQQ  595
p75 aa con  KCPKIQISKK YILMGISENS TDRECMADK NSLVIQMRDA WIRRLRKLQR  571
```

Fig. 7b p75 & p78 Formatted Alignment

```
p78 aa con  REKKGKCRKA  605
p75 aa con  REKKGKCMKP  581
```

B1 domain V-1 Formatted Alignment

```
MSB1  V    FSVGLIAQQC  RCKLHVEGER  CDVCKEGFYD  LSAEDPYGCK  SCACNPLGTI   197
HUMB1 V    FSIGLIAQQC  RCKLNVEGEH  CDVCKEGFYD  LSSEDPFGCK  SCACNPLGTI   197
FFB1  V    LEEGAVAGAC  HCKAFVTGRR  CNQCKDGYWN  LQSDNPHGCE  PCTCNPLGTL   200
p75 V-1    ----------  ----------  ----------  ----------  ----------    56
p78 V-1    ----------  ----------  ----------  ----------  ----------    56
Consensus  ...G..AG.C  .CK..V.G..  C..CK.G...  L.....P.GC  .C.CNPLGT.   200

MSB1  V    PGGNPCDSET  GYCYCKRLVT  GQRCDQCLPQ  HWGLSNDLDG  CRPCDCDLGG   247
HUMB1 V    PGGNPCDSET  GHCYCKRLVT  GQHCDQCLPE  HWGLSNDLDG  CRPCDCDLGG   247
FFB1  V    -NNSGCVMRT  GECKCKKYVT  GKDCNQCMPE  TYGLSESPEG  CSLCNCDAGG   249
p75 V-1    ----------  ----------  ----------  ----------  ----------    56
p78 V-1    ----------  ----------  ----------  ----------  ----------    56
Consensus  -....C...T  G.C.CK..VT  G..C.QC.P.  ..GLS....G  C...C.CD.GG  250

MSB1  V    AINNSCSEDS  GQCSCLPHMI  GRQC------  ----------  ----------   271
HUMB1 V    AINNSCFAES  GQCSCRPHMI  GRQCNEVERG  YY--------  ----------   279
FFB1  V    SYINYCDVIS  GQCRCRPHMI  GRSC------  ----------  ----------   273
p75 V-1    ----------  ----------  ----------  ----------  ----------    56
p78 V-1    ----------  ----------  ----------  ----------  ----------    56
Consensus  ...N.C...S  GQC.C..PHM.  GR.C------  ----------  ----------   282
```

Fig. 10b

B1 domain V-2 Formatted Alignment

```
HUMB1 V     NCFCYGHASE CAPVD-GHN- -EEVEGMVHG HQMCRHNIKG LNCELQMDFY    47
MSB1 V      NCFCYGHASE CAPVD-GVN- -EEVEGMVHG HQMCRHNIKG LNCELQMDFY    47
FFB1 V      SCSCYGHASQ CLPLDPAFSQ ADNEDGMVHG RCECIHNIKG MNCEECEDFF    50
p75 V-2     A--------- ---------- ---------- ---------- ----------     1
p78 V-2     A--------- ---------- ---------- ---------- ----------     1
Consensus   .C.CYGHAS. C.P.D..... -......... .GMVHG .C.C.HNIKG .NCE.C.DF.    50

HUMB1 V     HDLPWRPAEG RNSNACKKQN CNFHSTSCHF DMAVYLATGN VSGGVCDLQ    97
MSB1 V      HDLPWRPAEG RNSNACKKQN CNFHSSSCHF DMAVFLATGN VSGGVCDLQ    97
FFB1 V      NDLPWKPAFG KKINACKKQE CNLHAVSCHF DEAVFTASGF VSGGVCDNL   100
p75 V-2     ---------- ---------- QN HARRCRF NMELYKLSGR KSGGVCLNR    33
p78 V-2     ---------- ---------- QN HARRCRF NMELYKLSGR KSGGVCLNR    33
Consensus   .DLPW.PA.G ...NACKKQN CN.HA.SCHF DMAVY.ASG. VSGGVCLNC.   100

HUMB1 V     QKPFYYQHPE RDTRDPNFQE RCTCDPAGSQ NEGICDSYTD                147
MSB1 V      QKPFYYQHPE RDTRDPNLQE PCTCDPAGSE NGGICDGYTD                147
FFB1 V      QMPYFYRDPE QDTISERVQQ PCDCDPQGSS DDGICDSLNE                150
p75 V-2     QKEGFYRDLS KSIIDRKACK ---------- ----------                 63
p78 V-2     QKEGFYRDLS KEISHRKACK ---------- ----------                 63
Consensus   QKP.FYRDPE .DII.D...Q. .C.CDP.GS. ..GICD....                150
```

Fig. 11a

B1 domain V-2 Formatted Alignment

```
HUMB1 V    FSTGLTAGQC  RCKLNVEGEH  CDVCKEGFYD  LSSEDPFGCK  SCACNPLGTI   197
MSB1 V     FSVGLTAGQC  RCKLHVEGER  CDVCKEGFYD  LSAEDPYGCK  SCACNPLGTI   197
FFB1 V     LEEGAVAGAC  HCKAFVTGRR  CNQCKDGYWN  LQSDNPEGCE  PCTCNPLGTL   200
p75 V-2    ----------  ----------  ----------  ----------  ----------    63
p78 V-2    ----------  ----------  ----------  ----------  ----------    63

Consensus  ...G..AG.C  .CK..V.G..  C..CK.G...  L.....P.GC.  .C.CNPLGT.  200

HUMB1 V    PGGNPCDSET  GHCYCKRLVT  GQHCDQCLPE  HWGLSNDLDG  CRPCDCDLGG   247
MSB1 V     PGGNPCDSET  GYCYCKRLVT  GQRCDQCLPQ  HWGLSNDLDG  CRPCDCDLGG   247
FFB1 V     -NNSGCVMRT  GHCKCKKYVT  GKDCNQCMPE  TYGLSESPEG  CSLCNCDAGG   249
p75 V-2    ----------  ----------  ----------  ----------  ----------    63
p78 V-2    ----------  ----------  ----------  ----------  ----------    63

Consensus  -.....C...T  G.C.CK..VT  G..C.QC.P.  ..GLS.....G  C...C.CD.GG  250

HUMB1 V    ALNNSCFAES  GQCSCRPHMI  GRQCNEVEPG  YY                        279
MSB1 V     ALNNSCSEDS  GQCSCLPHMI  GRQC------  --                        271
FFB1 V     SYDNYCDVIS  GQCRCRPHMI  GRSC------  --                        273
p75 V-2    ----------  ----------  ----------  --                        63
p78 V-2    ----------  ----------  ----------  --                        63

Consensus  ...N.C....S  GQC.C.PHM.  GR.C------  --                       282
```

Fig. 11b

B1 domain V-3    Formatted Alignment

```
HUMB1 V     NCFCYGHASE CAPVD-GFN- -EEVEGMVHG HQMCRHNIKG LNCELCMDFY    47
MSB1 V      NCFCYGHASE CAPVD-GVN- -EEVEGMVHG HQMCRHNIKG LNCELCMDFY    47
FFB1 V      SCSCYGHASQ CLPLDPAFSQ ADNEDGMVHG RCECTHNIKG MNCECEDFF     50
p75 V-3     ---------- ---------- ---------- ---------- ----------
p78 V-3     ---------- ---------- ---------- ---------- ----------
Consensus   .C.CYGHAS. C.P.D.....  -.....GMVHG .C.C.HNIKG .NCE.C.DF.   50

HUMB1 V     HDLPWRPAEG RNSNACKKCN CNEHSISCHF DMAVYLATGN VSGGVCDDCQ    97
MSB1 V      HDLPWRPAEG RNSNACKKCN CNEHSSSCHF DMAVFLATGN VSGGVCINCQ    97
FFB1 V      NDLPWKPAFG KKINACKKCE CNDHAVSCHF DEAVFTASGF VSGGVCINCL   100
p75 V-3     ---------- ---------- ---------- ---------- ----------
p78 V-3     ---------- ---------- ---------- ---------- ----------
Consensus   .DLPW.PA.G ..NACKKC. CN.H..SCHF D.AV..A.G. VSGGVCD.C.    100

HUMB1 V     HNIMGRNCEQ CKPFYYQHPE RDIRDPNFCE RCTCDPAGSQ NEGICDSYTD   147
MSB1 V      HNIMGRNCEQ CKPFYFQHPE RDIRDPNLCE PCTCDPAGSE NGGICDGYTD   147
FFB1 V      HNIRGQHCEE CMPYFYRDPE QDTTSERVCQ PCDCDPQGSS DDGICDSLNE   150
p75 V-3     ---------- ---------- ---------- ---------- ----------
p78 V-3     ---------- ---------- ---------- ---------- ----------
Consensus   HNI.G..CE. C.P.....PE .DI......C. .C.CDP.GS. ..GICD.....   150
```

Fig. 12a

B1 domain V-3  Formatted Alignment

```
HUMB1 V     FSTGLIAGQC  RCKLNVEGEH  CDVCKEGFYD  LSSEDPFGCK  SCACNPIGTI   197
MSB1 V      FSVGLIAGQC  RCKLHVEGER  CDVCKEGFYD  LSAEDPYGCK  SCACNPIGTI   197
FFB1 V      LEEGAVAGAC  HCKAFVTGRR  CNQCKDGVWN  LQSDNPEGCE  PCICNPIGTL   200
p75 V-3     ----------  ----------  ----------  ----------  AGCCPVGA-     9
p78 V-3     ----------  ----------  ----------  ----------  EGCCPVGA-     9
Consensus   ...G..AG.C  .CK..V.G..  C..CK.G...  L.....P.GC  ..C.CNP.GT.  200

HUMB1 V     PGGNFDSET  GYVCKCRIVT  GQFDCDQ.PE  HWGLSNDLDG  CRPCDCDILGG   247
MSB1 V      PGGNFDSET  GYVCKCRIVT  GQFDCDQ.PQ  HWGLSNDLDG  CRPCDCDILGG   247
FFB1 V      -NNSCVMRT  GECKCKVVT  GKDCNCQMPE  TYGLSESPEG  CSLCNCDAGG    249
p75 V-3     -AGKICNQIT  GQCHCDGVT  GLICNFCAK-  -GFQQSRSP   VAPCI---     50
p78 V-3     -AGQICNQIT  GQCFCDGVT  GTICNFCAK-  -GVQQSRSP   IAPCI---     50
Consensus   -.G.....T  G.C.CK..VT  G..CNC..P.  ..GLS.S..G  C.PC.CD.GG   250

HUMB1 V     ALNNSCFAES  GQCSCRPHMI  GRQCNEVERG  YY                      279
MSB1 V      ALNNSCSEDS  GQCSCLPHMI  GRQC------  --                      271
FFB1 V      SYDNYCDVIS  GQCRCRPHMI  GRSC------  --                      273
p75 V-3     ----------  ----------  ----------  --                      50
p78 V-3     ----------  ----------  ----------  --                      50
Consensus   ...N.C....S GQC.C.PHM.  GR.C------  --                      282
```

Fig. 12b

B2 domain V-1 Formatted Alignment

| | | | | |
|---|---|---|---|---|
| MSB2 V | -CKCNGHASE | QVKN----EFD | K-IMQCKFN | TYGVLCEKCL | PFFNDREWRR | 45 |
| HUMB2 V | -CKCNGHASE | QMKN----EFD | K-IMQCKFN | TYGVLCEKCL | PFFNDREWRR | 45 |
| FFB2 V | -CKCNGHASK | QVPSIGMHGE | RIIMQFGRN | TLGPLCDRCL | PLYNDLKWKR | 49 |
| p78 V-1 | FCKCNGHASR | QVRD----RDD | N-IMQCKFN | TAGPECDRCK | PFHYDREWQR | 46 |
| p75 V-1 | FCKCNGHASR | QVKD----KEQ | K-IMQCKFN | TFGPECDRCK | PFHYDREWQR | 46 |
| Consensus | -CKCNGHAS. | QVK.----..D | K-IMQ.CKFN | T.GPLCDRCL | PF.NDREW.R | 50 |

| | | | | |
|---|---|---|---|---|
| MSB2 V | ATAEFSAGESL | PCDCNGRSQE | CYFDPELYRS | TGHGHCINC | RINIDGAKCE | 95 |
| HUMB2 V | ATAEFSAGECL | PCDCNGRSQE | CYFDPELYRS | TGHGHCINC | QINIDGAHCE | 95 |
| FFB2 V | SISTEMNECK | ACNCNGLADK | CFFDANLFNR | TGHGHCLDC | RENRDGPNCE | 99 |
| p78 V-1 | ATARFEANECV | ---------- | ---------- | --------- | ---------- | 56 |
| p75 V-1 | ASARFEANECL | ---------- | ---------- | --------- | ---------- | 56 |
| Consensus | A.A.EANECL | .C.CNG.... | C.FD..L... | TGHGHC..C | ..N.DG..CE | 100 |

| | | | | |
|---|---|---|---|---|
| MSB2 V | RCRENFFRLG | NIEACSPCHC | SPVGSLSTQC | DSYGRCSCKP | GVMGDKCDRC | 145 |
| HUMB2 V | RCRENFFRLG | NIEACSSCHC | SPVGSLSTQC | DSYGRCSCKP | GVMGDKCDRC | 145 |
| FFB2 V | RCKENFY-MR | DDGYCVNCAC | DPVGSRSLQC | NSHGKCQQKP | GVIGDKCDRC | 148 |
| p78 V-1 | ---------- | ---------- | ---------- | --------- | ---------- | 56 |
| p75 V-1 | ---------- | ---------- | ---------- | --------- | ---------- | 56 |
| Consensus | RC.ENF.-.. | ....C..C.C | .PVGS.S.QC | .S.G.C.CKP | GV.GDKCDRC | 150 |

Fig. 13a

B2 domain V-1 Formatted Alignment

```
MSB2 V     QPGFHSLTEA GCRPCSCDLR GSTDE----CN VETGRCVCKD NVEGFNCERC    192
HUMB2 V    QPGFHSLTEA GCRPCSCDPS GSTDE----CN VETGRCVCKD NVEGFNCERC    192
FFB2 V     DNNYQFGPH  GCQQQGCDSG GSHQNTPACD TETGICFCKE NVEGRRCNEC    198
p78 V-1    ---------- ---------- ---------- ---------- ----------     56
p75 V-1    ---------- ---------- ---------- ---------- ----------     56

Consensus  .......... GC..C.CD.. GS...----

B2 domain V-2 Formatted Alignment

```
MSB2 V      CKCNGHASEC VKN---EEFDK -LMCNCKHNT YGVDCEKCLP FFNDRPWRRA         46
HUMB2 V     CKCNGHASEC MKN---EEFDK -LVCNCKHNT YGVDCEKCLP FFNDRPWRRA         46
FFB2 V      CKCNGHASKC VPSIGMHGER TLMCCRHNT  DGPDCDRCLP LYNDLKWKRS         50
p78 V-2     ---------- ---------- ---------- ---------- ----------
p75 V-2     ---------- ---------- ---------- ---------- ----------
Consensus   CKCNGHAS.C .......... .L.C.C.HNT .G.DC..CLP ..ND..W.R.         50

MSB2 V      TAESASESLP QCNGRSQFC  MFDPEIYRST GH--GGICIN CRDNIDGAKC           94
HUMB2 V     TAESASECLP QCNGRSQFC  MFDPEIYRST GH--GGICIN CQDNIDGAHC           94
FFB2 V      TSTEVNECKA QCNGLADKC  FFDANLFNRT GH--GGICLD CRENRIDGANC          98
p78 V-2     ---------A CNCNIHARFC RFNMEIYKLS GRKSGGVCIN CRHNIAGRHC           41
p75 V-2     ---------A CNCNIHARFC RFNMEIYKLS GRKSGGVCIN CRHNIAGRHC           41
Consensus   T......E.A QNCNG.A..C .ED.EIY..T GH--GGICIN CR.NIDG.HC          100

MSB2 V      EFCFENFFRL GNIEACSPCH CSPVGSLSTQ CDSYGRCSCK PGVMGDKCDR          144
HUMB2 V     EFCFENFFRL GNNEACSSCH CSPVGSLSTQ CDSYGRCSCK PGVMGDKCDR          144
FFB2 V      EFCKENFY-M RDDGYCVNCA CDPVGSRSLQ CNSHGKCQCK PGVTGDKCDR          147
p78 V-2     HYCKEGFYR- ---------- ---------- ---------- ----------           50
p75 V-2     HYCKEGFYR- ---------- ---------- ---------- ----------           50
Consensus   EFCKENFYR. ......C.C. C.PVGS.S.Q C.S.G.C.CK PGV.GDKCDR          150
```

Fig. 14a

B2 domain V-2 Formatted Alignment

```
MSB2 V      CQPGFHSLITE AGCRPCSCDL RGSIDE---C NVEIGRCVCK INVEGFNCER     191
HUMB2 V     CQPGFHSLITE AGCRPCSCDP SGSIDE---C NVEIGRCVCK INVEGFNCER     191
FFB2 V      CINNYQFGP HGQQQGCDS GGSHQNTPAC DIEIGICFCK ENVEGRCNE          197
p78 V-2     ---------- ---------DLS- ------ ---------- ----------        53
p75 V-2     ---------- ---------DLS- ------ ---------- ----------        53
Consensus   C........L.. .GC..C.CD. .GS.....-C ..EIG.C.CK .NVEG..C..    200

MSB2 V      CKPGFFNLES SNPKGCTPCF CFGHSSVC  ---------                    219
HUMB2 V     CKPGFFNLES SNPRGCTPCF CFGHSSVC  ---------                    219
FFB2 V      CKPGFFNLDK NNRFGCTPCF CYGHTSEC  ---------                    225
p78 V-2     CKPGFFNL-- --KP------I SHRKACK-  ---------                    63
p75 V-2     CKPGFFNL-- --KS------I TDRKACK-  ---------                    63
Consensus   CKPGFFNL.. SNRKGCTPCF C.GH.S.C                              228
```

Fig. 14b

B2 domain V-3   Formatted Alignment

```
MSB2 V      CKCNGHASEC VKN---EEFDK -LMCNCKHNT YGVDCEKCLP FFNDRPWRRA    46
HUMB2 V     CKCNGHASEC MKN---EEFDK -LVCNCKHNT YGVDCEKCLP FFNDRPWRRA    46
FFB2 V      CKCNGHASKC VPSIGMHGER TLVCECRHNT DGPDCRCLP  LYNDLKWKRS    50
p78 V-3     ---------- ---------- ---------- ---------- ----------
p75 V-3     ---------- ---------- ---------- ---------- ----------
Consensus   CKCNGHAS.C ........   -L.C.C.HNT .G.DC..CLP ..ND..W.R.    50

MSB2 V      TAESASESLP CDCNGRSQEC YFDPELYRST GHGHCTNCR  DNIDGAKECER   96
HUMB2 V     TAESASECLP CDCNGRSQEC YFDPELYRST GHGHCTNCQ  DNIDGAHCER    96
FFB2 V      TSTEMNECKA CNCNGLADKC FFDANLFNRT GHGHCLDCR  ENRDGPNCER   100
p78 V-3     ---------- ---------- ---------- ---------- ----------
p75 V-3     ---------- ---------- ---------- ---------- ----------
Consensus   T......E.. C.CNG.....C .FD..L....T GHGHC..C.  .N.DG..CER  100

MSB2 V      CRENFFRLGN TEACSSCHCS PVGSLSIQCD SYGRCSCKPG VMGKCDCRCQ   146
HUMB2 V     CRENFFRLGN NEACSSCHCS PVGSLSIQCD SYGRCSCKPG VMGKCDCRCQ   146
FFB2 V      CKENFY-MRD DGYCVNCAQD PVGSRSLQCN SHGKCQCKPG VIGKCDCRCD   149
p78 V-3     ---------- ----EQCH   PVGAAQT--  ---------- ----------    13
p75 V-3     ---------- ----AQCH   PVGAAGKT-- ---------- ----------    13
Consensus   C.ENF.-... ....C..Q.Q. PVGS.S.QC. S.G.C.CKPG V.GKCDCRC.   150
```

Fig. 15a

B2 domain V-3   Formatted Alignment

```
MSB2 V      PGFHSLTEAG CRPCSCDLRG SIDE------ QNV EITGRCVCKDN VEGFNCERCK  193
HUMB2 V     PGFHSLTEAG CRPCSCDPSG SIDE------ QNV EITGRCVCKDN VEGFNCERCK  193
FFB2 V      NNYYQFGPHG CQQGCDSGG SHQNTPAQDT EIGICFCKEN VEGRRCNECK  199
p78 V-3     ---------- ---------- ---------- CNQ TTGQPCKDG MTGLTCNRCA   36
p75 V-3     ---------- ---------- ---------- CNQ TTGQPCKDG MIGLTCNRCA   36
Consensus   .........G C..C.CD..G S......   QN. EITG.C.CKDN VEG..CNRCK  200

MSB2 V      HGFFNLESSN PKGCTPCFCF GHSSVC                                 219
HUMB2 V     HGFFNLESSN PRGCTPCFCF GHSSVC                                 219
FFB2 V      HGFFNLDKNN RFGCTPCFCY GHTSEC                                 225
p78 V-3     KGYQQSRSP- ---------- -TAPCI                                  50
p75 V-3     KGFQQSRSP- ---------- -VAPCI                                  50
Consensus   HGFFNL.S.N ..GCTPCFC. GH.S.C                                 226
```

Fig. 15b

B1 domain VI Formatted Alignment

```
p78 VI      GYPXLNFAV QIXADPCYDE HGLPXRCIPD FVNSAFGKEV K--VSSTCG-    47
p75 VI      ANPFV---AQ QTPPDPCYDE SGAPPCIPE FVNAAFGKEV Q--ASSTCG-    44
HUMB1 VI    AQE------PE FS---Y---- GCAEGSCMPA TGDLLIGRAQ KLSVISTCGL   38
MSB1 VI     -QE------PE FS---Y---- GCAEGSCMPA TGDLLIGRAQ KLSVISTCGL   37
FFB1 VI     RRD------RPK YPPNKFIKIH PCERSSCMPA TGNLLIGREN RLITASSICGL  46
Consensus   ..-------P.  ........   .CA..SOMPA TGNLLIGRE. KL.VSSTCGL  50 p78 VI      KPFSRYCVVT EKGEEQ--VR SCHLCNASDP KRA--HPPSF LTID--LNNPH    91
p75 VI      KPFIRFC--- ---------- ------DASDP RRA--HPPAY LTID--LNIAA    72
HUM

B1 domain VI Formatted Alignment

```
p78 VI      DYGKTWVPFQ FYSIQRKMY NKPSRAAIIK QNEQEAICID SHIDVRPLSG   191
p75 VI      DYGKTWVPYQ YYSSQRKIY GKPSKAIVIK QNEQEAICID GLIDLYPLIG   172
HUMB1 VI    DFGKTWGVYR YFAYDEASF --PGISIGEM KKVDDIICDS RYSDIEPSTE   182
MSB1 VI     DFGKTWGVYR YFAYDEASF --PGISIGEM KKVDDIICDS RYSDIEPSTE   181
FFB1 VI     DFGQIWHIYR YFAYDCKESF --PGVPT-VL ENITDMCIS RYSNVEPSRN   188
Consensus   DFGKTW...YR YFAYIQ..SF ..EG..T... .N.D.ICIS RYSD.EPST.   200 p78 VI      GLIAFSIIDG RPTAHDFINS PVLQWTAT DIKVTFSRIH IFGD------E    236
p75 VI      GLIAFSIIDG RPSAQDFDSS PVLQWTAT DIRVVFSRPH LFRELGREA       222
HUMB1 VI    GEVIFFRALDP AFKIED-PYS PRIQNLLKIT NLRIKFVKLH ILGD------N   226
MSB1 VI     GEVIFFRALDP AFKIED-PYS PRIQNLLKIT NLRIKFVKLH ILGD------N   225
FFB1 VI     GEVIFRMIPP NINVID-PYA EHVQNQLKMT NLRIQMIKLH KLGD------N   232
Consensus   GEVIER.LDP ......D-PYS P..QN.IK.T .NLRI.F.KLH ILGD------N   250 p78 VI      NEDDSELARD SYFYAVSDLQ MEG                                 259
p75 VI      GEEDGGAGAT FYMYSVGELQ MEG                                 245
HUMB1 VI    LLDSRMEIRE KYMYAVYDMV VRG                                 249
MSB1 VI     LLDSRMEIRE KYMYAVYDMV VRG                                 248
FFB1 VI     LLDSRLENEE KYMYGISNMV VRG                                 255
Consensus   LLDSR.E.RE KYMYAV.DMV VRG                                 273
```

Fig. 16b

B2 domain VI Formatted Alignment

```
HuMB2 VI    QAAMD------          ----------  -EQIDEGGRP QRQMPFFMA A-NVIVVAIN   34
MSB2 VI     -AAMD------          ----------  -EQADEGGRP QRQMPFFMA A-NVIVVAIN   33
FFB2 VI     RPPINSAGGH ELRGTTFMPA LEQMDPYGRP QKQLPFFINA AYQLQIESIN              50
p78 VI      GYPXINMFAV QIXAD----- -EQMDEGLP XRQIPFMNS AFGKEVKVSS               44
p75 VI      ANPFV----AQ QITPPD----            -EQMDESGAP PRQIPFFMNA AFGKEVQASS  41
Consensus   ..P.. .--- ..........  -EQMDE.GRP QRQ.PFFMNA AF...V.AIN            50

HuMB2 VI    TCGIPPE-EY QVQIG-VIGV TKSCHICDAG QPHLQFGAAF LTDMNQADT                82
MSB2 VI     TCGIPPE-EY QVQIG-VIGV TKSCHICDAG QQHLQFGAAF LTDMNQADT                81
FFB2 VI     TCGEQNDNHF QIQT--MQN HKNCEFC--- -KYNDHNPSF LTD-HDPQSP                94
p78 VI      TCGKPPS-RY QVWTEKGEEQ VRSCHICNAS DPKRAHPPSF LTD-NNPHNL                93
p75 VI      TCGKPPT-RH Q--------- ---------DAS DPRRAHPPAY LTD-NTAANM              74
Consensus   TCG.PP.-.Y QVQT...... .KSCHICDA. .P...H.PAF LTD.NN.A..               100

HuMB2 VI    TWWQSQIMLA GVQMPSSINL TTHGKAFDI TYVRLKFHTS RPESFAIMKR                132
MSB2 VI     TWWQSQIMLA GVQMPNSINL TTHGKAFDI TYVRLKFHTS RPESFAIMKS                131
FFB2 VI     TWWQSEIMFE GIQHPNVNL TTHGKSYDI TYVRILFRSP RPESFTIMKR                 144
p78 VI      TCWQSDSYV- --QMPHNVIL TLSGKKFEV TYVSLQFCSP RPESVAIMKS                140
p75 VI      TCWFSEITLH- ---HIPHNVIL TLSGKKFEV VVVSLQFCSP RPESTAIFKS                121
Consensus   TWWQS.TM.. G.QMP..VNL TTHGK.FDI TYVRL.F.SP RPESFAIMKR                 150
```

Fig. 17a

B2 domain VI Formatted Alignment

```
HUMB2 VI    TREDGHMIFY QMYSGSCENT YSKANRGFIR TGGDEQQAIC TDEFSDFSPL    182
MSB2  VI    TREDGHMIFY QMYSGSCENT YSKANRGFIR TGGDEQQAIC TDEFSDISPL    181
FFB2  VI    TSESGHMIFY QFYSADCRDT YSLPDSRAIR KGEGEAHAIC TSEYSDISPL    194
p78   VI    MDYGKIWMFF QFYSIQCRKM YNKPSRAATT KQNEQE-AIC TDSHIDVRPL    189
p75   VI    MDYGKIWMFY QMYSSQCRKI YGKPSKATVT KQNEQE-AIC TDGLIDLYPL    170
Consensus   T.E.GHMIFY QMYS..CR.T YSKP.R..IR KG..E..AIC TDE.SD.SPL    200

HUMB2 VI    TGGNMAFSIL EGRPSAYNFD NSPVLQFWT AIDIRVTLNR LNIFGD-----   228
MSB2  VI    TGGNMAFSIL EGRPSAYNFD NSPVLQFWT AIDIRVTLNR LNIFGD-----   227
FFB2  VI    RIGEIAFSIL EGRPSGINFE RSGHLQFWT AIDIRTTLDR LNIFGD-----   240
p78   VI    SGGLIAFSIL IGRPIAHDFD NSPVLQFWT AIDIKVIFSR LHIFGD-----   235
p75   VI    TGGLIAFSIL DGRPSAQHFD SSPVLQFWT AIDIRVVFSR PHLFRELGGR    220
Consensus   TGG.IAFSIL EGRBSA.NFD NSPVLQFWT AIDIRVTL.R LNIEGD-----   250

HUMB2 VI    -EVFNDPKV- LKSYMYAISD FAVGR                              252
MSB2  VI    -EVFNEPKV- LKSYMYAISD FAVGR                              251
FFB2  VI    -ELFGDSQV- LKSYFIYAISD IAVGAR                            264
p78   VI    -ENEDDSELA RDSYFIYAVSD LQVGG-                            259
p75   VI    FAGEFDGGAG ATHYMYSVGE LQVGG-                             245
Consensus   -E.F.D..V- LKSYMYAISD .AVGR                              276
```

Fig. 17b chick p78 & mouse p78 Formatted Alignment

```
mouse p78  ---------- ---------- ---------- ---------- ----------
chick p78  MPRRGAEGPL ALLLAAAWLA QPLRGYPXL NMFAVQLXAD PCYDEHGLPX    50 mouse p78  ---------- ---------- ---------- YCV VSEGEFVR SCHLQNSDP   23
chick p78  RCIPDFVNSA FGKEVKVSST CGKPPSRYCV VIEKGEFQVR SCHLQNASDP   100 mouse p78  KFAHPFAFLIT DINNPHNLIC WQSEMYQFP HNVILTLSLG KKFEVTYVSL    73
chick p78  KFAHPFSFLIT DINNPHNLIC WQSDSYMQMP HNVILTLSLG KKFEVTYVSL   150 mouse p78  QFCSPRPESM AIYKSMDYGR IWPFQFYST QCRKMYNRPH RAPITKQNEQ     123
chick p78  QFCSPRPESM AIYKSMDYGK IWPFQFYST QCRKMYNKPS RAPITKQNEQ    200 mouse p78  FAMCIDSHID MRPLSGGLIA FSTLDGRPSA HDFINSPVLQ DWTATDIRV    173
chick p78  FAICIDSHID MRPLSGGLIA FSTLDGRPIA HDFINSPVLQ DWTATDIKV   250 mouse p78  AFSRLHFGD ENEDDSELAR DSYMYAVSDL QVGGRCKCNG HAARCVRDRD    223
chick p78  TFSRLHFGD ENEDDSELAR DSYFYAVSDL QVGGRCKCNG HASRCVRDRD   300
```

Fig. 18a chick p78 & mouse p78 Formatted Alignment

```
mouse p78  DSLVCDCKHN TAGPECDRCK PFHYDRPWQR ATAREANECV ACNNLHARR  273
chick p78  DNLVCDCKHN TAGPECDRCK PFHYDRPWQR ATAREANECV ACNNLHARR  350 mouse p78  CRFMMELYKL SGRKSGGVCL NQXXNXXRH CHYXXGXLL PFHGKPIIHR    323
chick p78  CRFMMELYKL SGRKSGGVCL NQRFNPAGRH CHYCFG-FY RDLSKPISHR   399 mouse p78  KACKXDCHP VGAAGKTCNQ TIGQQPCKDG VIGITCNRCA KGYQQSRSPI   373
chick p78  KACKEDCHP VGAAGQTCNQ TIGQQPCKDG VIGITCNRCA KGYQQSRSPI   449 mouse p78  APCIKIFVRR FTAASXVFFX XHDCDSYCKA SKGKLKMMK KYCKDYAVQ     423
chick p78  APCIKIFAAP EPIAASSIEF PADCDSYCKA SKGKLKIIMK KYCKDYAVQ    499 mouse p78  IHILKADKAG DWKFIVNII SVYKQGTSRI RRGDQSIMR SPDIACKCPK     473
chick p78  IHILKAFKNA DWKFIVNII SVYKQGSNRL RRGDQIIWVH AKDIACKCPK    549 mouse p78  IKHKKYLLL GNAXDSPDQS GIMADKSSLV IQMRDIWARR LRKFQQREKK   523
chick p78  VKMKKYLLL GSTEDSPDQS GIIIADKSSLV IQMRDIWARR LRKFQQREKK   599
```

Fig. 18b chick p78 & mouse p78 Formatted Alignment 529
605 mouse p78  GKQKA
chick p78  GKQRKA

Fig. 18c m p78, p78, p75, unc-6 Formatted Alignment

```
UNC-6         ---------- ---------- ---------- ---------- ----AIGAIC ACAICAGIAT T-GC-GCTAT    24
p78 na con    AIGCCGGGA GGGGGCGGA GGGGCGCTC GCCCIGCIGC TGGGGCGC                              50
mo p78 na con ---------- ---------- ---------- ---------- ---------- ---------- ----------
p75 na con    ---------- ---------- ---------- ---------- ---------- ---------- ----------
Consensus     AIGCCCGGGA GGGGGCGGA GGGMYGMIC RCMYYRSIRY TGGGGCYRY                            50

UNC-6         GIGCTAGCGC TCTACTTTIG T-AIGGGCAT AGTICAIGGA GCATACTTTT                         73
p78 na con    GIGGCIG-GC ACAGGGCIG CGAGGGGCT ACCCNNNCT GAACA-TGTT                            98
mo p78 na con ---------- ---------- ---------- ---------- ---------- ---------- ----------
p75 na con    ---------- ---------- ---------- ---------- ---------- ---------- ----------
Consensus     GIGSYWGGC WCWRCYKYIG YGAKGSGSMT ASCYCNNNSW GMAYACTKTT                          100

UNC-6         CACAGTICIC CAIGAGAGCC CCAGACCAIG AICCTTGCCA TGAICA-TAC                         122
p78 na con    C---GCGIG CA-GAGNCA GCGACC-CC ------TGCTA CGAGAGCAC                            138
mo p78 na con ---------- ---------- ---------- ---------- ---------- ---------- ----------
p75 na con    ---NTCCIG C--GCCIGCT GCTCACCACC A-GGIGCTC CGCCIGGCAC                           43
Consensus     CACANYSIS CAIGMSINCH SCHSACCAYS AISCKIGCYM YGMYBRGYAC                         150
```

Fig. 19a m p78, p78, p75, unc-6 Formatted Alignment

```
UNC-6         TGTCG---A CCAGTTCGAT GTGTTCCCGA GTTCAT-AAA TGC-TG TTT    167
p78 na con              GGGCTG---- CCCNCCGCT GCATCCCGGA CTTCGTCAAC T-CG-G CCTT   182
mo p78 na con  ---------- ---------- ---------- ---TGTATGT TGTGTG RTT     17
p75 na con    GAGCTGCAAA CCCTTCGTG CTCAGCAGA CTCCCCAGA CCCTG TAC     93
Consensus     KRGYYGCAAA CCMSNYCGHK GYDYHSCVGA STYYVYMRH YSYSIG MWY    200

UNC-6         -TG AAAACC TGTTATTGCT AGTGATACAT G GGAACAAA CCGACCAGAC    216
p78 na con    -CG AAGGA GGTCGAAGGT GT-CGAGAC -C TGGGGAA GCGCCGGTCG    228
mo p78 na con -TG CANNNA TAACAATTC ACACAGAAA - AGCNNNNN NNNNNNNN     65
p75 na con    GATCAGAGGG GGGCTCCCCC CCGC-TGCAT -C ---CCGAG TTCGTCAAG    139
Consensus     GWEG NNNNV KRDYDHHBBY RBDSRDRMAH G DGMNNNNN NNNNNNNN    250

UNC-6         AAGTATT GTA CTGT GAAGGA TGG AATTATC GGT GAGCAAT        265
p78 na con    AGTAT ACGG TGG GACGA GAAGG--GCG AGAGC-A-- GGT CGC-TC        272
mo p78 na con -AGNGCTAC TGCG TGG TGAGGA GCGTG--GTG AAGAC-G-- CGT GCGG-TC     109
p75 na con    CCGC-CT TTG GGAAGGAGGT AGCAGGTTCC AGCACCTGT- GGA AAGC-CC       186
Consensus     NVSYAY KYR BKRM GRVSGW GMRKKCYKBV WRSA VYTRIC SGKVM CAHY    300
```

Fig. 19b m p78, p78, p75, unc-6 Formatted Alignment

```
UNC-6         GTGACACTTG TGATCCTAGA AACCATTTC  AATCCCA--- ---TCCA---   306
p78 na con    GTTGCCAC-- ---------- ---CTCTTGC AA-GCCTTC  GACCCAAGC GGGGCCACCC  314
mo p78 na con CTGTCCAC-- ---------- ---CTCTTGC AA-CTCTTTG GATCCAAGA AAGGCACC     151
p75 na con    CCAACAC--- ---------- ---GGCACTT GA-TGCCTTG GACCCAGCC GAGCCCACCC   230
Consensus     SYRHCACTTG TGRYDCTWGM FACYDYYTTS RAMCCMRSM RMGYSCACCC            350

UNC-6         GCCTCTCTTT CTAACTGATC TCAATTCGAT TGGA-AACAT GACTGCCTGG            354
p78 na con    GCCCTCTTTN CTCACGGAC  TCAACAAC-C GCCACAACT GACTGCCTGG              363
mo p78 na con GCCGCTTCC  CTCACGCTTC TCAAATAAC-C GCACAAACT GACTGCCTGG             200
p75 na con    ACCCGCCTAC CTGACGGA   TCAACACGC  GG-CAACT GACGTGCCTGG              279
Consensus     FCCYBYCWMN CTMAMGMVC  TCAAYWMSRY YGSACAAMT GACRTGCCTGG             400

UNC-6         -GTTTGACT  CAAGTTGA  G---CCACAA AAGTTGAC TCACTTTTC                 401
p78 na con    CAGTCCACA  GCTAGCTGCA GTACCCAC  AAGTCACC  TCACGCTGTC               413
mo p78 na con CAGTTCCAGA ACTACCTGA  GTTCCCAC  AAGTGAGA TCACTGTGC                 250
p75 na con    CGTTCCAGA  CCTTGCACCA CCTGCCCA  AAGTCACC TCACCTTTC                 329
Consensus     CREIMCCASW VCHWSBWBSA SYMSCVCAM  AAGTBMCVC TCACBYTKTC              450
```

Fig. 19e m p78, p78, p75, unc-6 Formatted Alignment

```
                                                                                          745
UNC-6       GCTTCAGGAT TGGGT ACG CAAGTGACAT TAAAGTGGTG TTTTCAAGGC  745
p78 na con  GCTGCAGGAC TGGGT ACG CCACTGACAT CAAGGTGAC- CTTTAGCCGC  762
mo p78 na con GCTGCAGGAC TGGGT ACG CCACTGACAT CCGGGTGC-- TTTTCAGCCC  599
p75 na con  GCTGCAGGAC TGGGT ACG CCACTGACAT CCGGGTGT-- CTTTAGCCGT  678
Consensus   GCTKCAGGAY TGGGT SACG CVAQYGACAT MRVGTGRYG  BTTYMRMSGY  800

UNC-6       TTTAGTCAGA TCAGGTGA TCAGGCTGAA CTGTATGGCT TGTCTAATGA TGTCAATTCG  795
p78 na con  CT-GCAGACC TTCGGCGA --GA ---------- G---AA CG       787
mo p78 na con CT-GCAGACG TTCGGCGA --GA ---------- G---AA CG       624
p75 na con  CC-CCAGCTC TTCGGCGAG --GA CTGGGGGGC-- CG------ GGCTGG CG  718
Consensus   YYASYMQMBV IYMSGCIGAR CTGKRKGGCT YGTCTAAGA KGYYRRTTGG  850

UNC-6       TACTGAAAAG AGACGGATGA TGAAGTCAAA CAAGTGTTACT TCTACTCAAT  845
p78 na con  -A-GG---AG ACTCGGA-GC TCGCCCCGGA C--TCCTACT TCTAGGCGTI  830
mo p78 na con -A-AG---AG ACTCGGA-GC TCGCCCCGA C--TCCTATT ACTATGCAGT  667
p75 na con  -A-GG---AG ACGGGGG-GG TGGGCCGGC 0--CCCTACT ACTACTTGGT  761
Consensus   TACTGAAAAG ASDSSGRIGV YSRVSBSMRM CAAYSYTAMT WCTAYKCVRT  900
```

Fig. 19f

Fig. 19g m p78, p78, p75, unc-6 Formatted Alignment

```
unc-6          ATGGGAAGA GCTAGGCAA ATTCTGCCAA CTCATGTGTC GCTTGCAACT  1045
p78 na con     CTGGCAGAGG GGCAGGCC GAGAGGCCAA CGAGTGGTG GCCTGCAACT  1030
mo p78 na con  CTGGCAGCC GCCAGGCCC GCGAGGCCAA GGAGTGCTG GCCTGCAACT   867
p75 na con     CTGGCAGGG GCAGTGCC GGGAGGCCAA CGAGTGCTG GCCTGCAACT   961
Consensus      VIGGSRRMGV GCCASSGCMM RHKMKGCCAA CKMRTGYSTS GCYTGCAACT  1100 unc-6          GCAACCAACA GGCAAAGACA TGCGGATTTG ATGCTGAGCT CTTTAGACTA  1095
p78 na con     GCAACCTTCA TGCACGGC TGCGGCTTCA ACATGGAGCT GTGCAAGCTG   1080
mo p78 na con  GCAACCTTCA TGCACGGGCA TGCGGCTTCA ACATGGAGCT GTATAGCTA    917
p75 na con     GCAACCTTCA GCGTCCGGG TGCCTCGCC ACATGGAGCT GTATAAGCTG   1011
Consensus      GCAACCWWCA MGCWMFGMGM TGCVMGMTOR AYRYKGAGCT STWYARRCTR  1150 unc-6          AGTGGCAACC CGTCAGGAGG AGTGTGCTTG AGTGTGCTTG ATTAACACTGC 1145
p78 na con     TCCGCAGAA AGAGGCGG TGTCTGCTT AACTGTGGC ACAACACGGC      1130
mo p78 na con  TCCGCAGGCA AGAGGGCA AGTGCCTTC AACTGCCNNN ACAACACTCN    967
p75 na con     TCCGCAGA AGAGGGGG CGTTTGCCTC AACTGCCAC ACAACACGGC       1061
Consensus      WSNGGSMRVM RGWSMGGVGG RGTRTGYTLS AACTGYCNNN AYAACACKSN  1200
```

Fig. 19h m p78, p78, p75, unc-6 Formatted Alignment

```
unc-6         TGGAAGAAAT TGTCATCTCT GCAAACAAG -----ATTTGTT CCGTGATTACT  1191
p78 na con    CCGGAGGCAC TGCCACTACT G-CAAGGAAG G----CTTCTA CCGGGACCTC  1176
mo p78 na con NNCCCCCAC TGCCACTACT GNNAAGGAAG GNNNCTTCTA CCGAGACAT-  1016
p75 na con    TGGAGGAC   TGCCACTACT G-CAAGGAG  G----CTTCTA CCGGGACCTC  1107
Consensus     NNGVMGMAY TGYCAYYWCT GNNAASSARG GNNNMTTSTA CCGNGAMYY   1250 unc-6         TCTCTCTGCAA TGACATCG GAAAGCTTGT AAAGCTTGTG GATGTCATCC  1241
p78 na con    AGCAAACCA TCTCCACG GAAAGCTTGC AAAGCTGTGG ATTGTCATCA  1226
mo p78 na con GGCAAGCCA TCCGGAGCCTA GAAAGCTTTG AAAGCTGTG ATTGCACCC  1066
p75 na con    AGCAAGTCCA TCAGGACG GAAAGCTTTG AAAGCTGTG ACTGTCACCC  1157
Consensus     DSYMRYCHA TSMVSAMCG GAARGMTGY AAAGMHTGYG RHTGYCAYCC  1300 unc-6         AGTGGATCA CTTGGAAAA GCTGCAAACA ATCATGGT CAGTGGTCT  1291
p78 na con    CGTGGGCC GCCGGCAA CTGCAAACA AACCAGGG CAGTGTCCAT  1276
mo p78 na con AGTGGGTCT GCTGCAAGA CTGCACTGC CAACACTGGC CAATGTCCCT  1116
p75 na con    AGTTGTGCT GCTGGCAAGA CTGCAACCGG CAACACTGGC CAGTGCCCGT  1207
Consensus     MGTBGGHKCH SYYGGVMARA SCTGCAAVCA AWCMCKGGB CARTGYSYVT  1350
```

Fig. 19i m p78, p78, p75, unc-6 Formatted Alignment

| | | | | |
|---|---|---|---|---|
| UNC-6 | GCAAGCCTGG AGTTACTTGGA ACAACCTGTA ATCGTTGTGC CAAAGGATAC | | | 1341 |
| p78 na con | GCAAGGAGG GGTCACTGGC ATCACCTTGA ACCGTTGGC CAAAGGTTAC | | | 1326 |
| mo p78 na con | GCAAGGAGG CGTGACGGC TGGACCTTGA ACCGATCTGC CAAAGGATAC | | | 1166 |
| p75 na con | GCAAGGAGG CGTGACGGC CTTACCTTGA ACCGGTGTGC CAAAGGTTTC | | | 1257 |
| Consensus | GCAAGSMYGG MGTSACHGGM MYMACCTTGYA AYCGHTGYGC CAARGGWWMC | | | 1400 |

| | | | | |
|---|---|---|---|---|
| UNC-6 | CACMAGCC GTTCTACAGT TACTCCTTGT ATTGAAATTC C-GAC-CAAA | | | 1389 |
| p78 na con | CAGCAGCA GTTCCCCAGA TCGCCCTTC ATAAAGATC CGGCGGCC | | | 1376 |
| mo p78 na con | CAGCAGCC GTTCCCCAT GTTCCCTTG ATCAAGATC CTG-TGGCC | | | 1215 |
| p75 na con | CAGCAGCC GTTCCCCTGT GCCCCCTGC ATCAAGATC CTGCATCAA | | | 1307 |
| Consensus | CARCAHAGCC GYTCMCYHRT BRCMCCBYGY ATMRARATYC CYGMYRYVMM | | | 1450 |

| | | | | |
|---|---|---|---|---|
| UNC-6 | GCTGATTCA TTGGATCATC A-CATTCA-G AA-GAGC--A AGATCAGTG- | | | 1433 |
| p78 na con | GCCCCCACA GCTG-CCAGC AGC-GCAG AGC----CTGC AGA-CTGTGA | | | 1421 |
| mo p78 na con | GCAG-CCACT GCAG-CCAGC AGNTGGAG AACNINNGA AGA-CTGTGA | | | 1261 |
| p75 na con | CCCGACCTGT CTTG-TCAGC AGCAGGAG CAC----CTGC AGA-CTGTGA | | | 1352 |
| Consensus | SCYSMYYMCW BVTGAYCAGC AGNRYKSAGG MRCNNNNKGM AGATGWGTGA | | | 1500 |

Fig. 19m m p78, p78, p75, unc-6 Formatted Alignment

```
UNC-6           ----------- ---------- ---------- AGATACTGA- ---------- ---------- ----------   1839
p78 na con      CGGTTGGGGG GNTTTTTKG  CATCTC----  A--------- ---------- ---------- ----------   1884
mo p78 na con   RRSG-GGGGG GNITTTTKG  -GTATT----  CGGGG-GTG  G-GGCCAGG- --GG-G-CT  C--AC---GG   1727
p75 na con      CAGGGGGCT  GTATATTTG  CCCGTCAGG   CAGGGGCT   G-GCAAAGC  -TGGCAGCCT TGGACT-TGG   1841
p75 na con      AGACCATCC  CAGAGACTCT GTACCGGTTC  AGACCATCC  GTACATACAT ATCGTGTGAA CGGACTCTTC   2000
Consensus       VRVBHVYVS  CRGRGRCKYK GTTRCRHASRY GTTRCRHASRY ATSGYRKSMW YGGACTCTKS UNC-6           ----------- ---------- ---------- ---------- ---------- ---------- ----------   1839
p78 na con      GNIWTTTKG  GNIWTTTKG  G-- AGGATG  GAA-GGGGA  A-AA-----A                         1915
mo p78 na con   CCCGTCAGGG CCAACGGTTC G-- AGGTGG  GNNCGGGC   G-AAGT-CGA                         1773
p75 na con      TGTCTATAGT GTATATTTC  CCAACGGTTC  CCCTTTTGT  GTGGTGTGC                          1891
p75 na con      YVVYSTMWRGK GNIWTTTKG GCAASGGWKS SNNNYKKKGH RTTRMGTGYGM                         2050
Consensus UNC-6           ----------- A--------- ---------- ---ACG----  AAACC-----                        1839
p78 na con                                                                                     1927
mo p78 na con   A-CCGTGGG  TGTGTGTGG  -GCCCTCAGC  CGTCCGGCCC  AGCCCWCCC  T-CACACCCC             1821
p75 na con      TGTGTGTGCC TGTGTGTGCG TGTGTGTGG   TGTGTGTGG  TGTGTGTGTG                         1940
Consensus       AGYGSGYGG  TGYSYKCAVS YGIVYGYSCS  YGIVYGYSCS  WRHSYSMSYS TGYRYRYSYS             2100
```

Fig. 19n m p78, p78, p75, unc-6 Formatted Alignment

```
UNC-6         ----------  ----------  ----------  ----------  ----------  1839
p78 na con    ----------  ----------  ----------  ----------  ----------  1927
mo p78 na con TGGCTGCCT   CTTATGCGC   ATGGCAGAA   AGNCCCTGT   ATTGACAGGC  1871
p75 na con    TGTGTCTCCT  CTCAGTGTGT  AT----TAAAA ATAAGGGGT   AATGACA---  1984
Consensus     TGKSTSYSCT  CTYAKKGYGY  ATGGGYARAA  AKMNSSCKGT  AWTGACAGGC  2150

UNC-6         ----------  ----------  ----------  ----------  ----------  1839
p78 na con    ----------  ----------  ----------  ----------  ----------  1927
mo p78 na con CAGGCCCTGG  ANAAATGAGG  A-CAAGACAT  A--GCTACCT  CACGGG-CT   1917
p75 na con    -A--ACCT--- -TTAATGAGG  AGCAAAGCAG  AGGGGTCCT   GTGGGTGCCT  2028
Consensus     CAGGMCCTGG  ANWAATGAGG  AGCAARRCAK  AGGGSKWCCT  SMSGGYGCCT  2200

UNC-6         ----------  ----------  ----------  ----------  ----------  1839
p78 na con    ----------  ----------  ----------  ----------  ----------  1927
mo p78 na con CCTTCCAGAA  -CAG--AGAT  GCCT--TCC   CTAGGGCTAG  GTG-GGGTC   1961
p75 na con    GCTGCCTGAA  GGAGCTTGAG  GGGCTTGTTT  CTTGCTCCGG  GCGTGCTGTT  2078
Consensus     SCTKCCWGAA  GSAGCTWGAK  GSSCTTGGTYY CTWGSKCYRG  GYGTGSKGTY  2250
```

Fig. 19o m p78, p78, p75, unc-6 Formatted Alignment

```
UNC-6              ----------  ----------  ----------  ----------  ----------  ----------  ----------  ----------  ----------  1839
p78 na con         ----------  ----------  ----------  ----------  ----------  ----------  ----------  ----------  ----------  1927
mo p78 na con      GCNNGTGGAG  GGGTTAGGGA  GGTCCTGAGA  ----------  ----------  ----------  ----------  GCCGGAACA   GAA---TGG   2007
p75 na con         CCTCACCCTT  CTGTC-CTAC  TCTCTCTTTC  ----------  ----------  CCCTTGAGCA  AAACCTCTG              2127
Consensus          SCNNRYSSWK  SKGTYASKRM  KSTCYKWKM   ----------  SSCKKGARCA  RAACCTTYKG                         2300

UNC-6              ----------  ----------  ----------  ----------  ----------  ----------  ----------  ----------  ----------  1839
p78 na con         ----------  ----------  ----------  ----------  ----------  ----------  ----------  ----------  ----------  1927
mo p78 na con      CACAGTGGT-  CT-AC--AG-  ----------  ----------  ----------  TGCCTGTGTT  TGATGT-TA   TTG-AAGGG   2050
p75 na con         CTGTCTGCTG  CTGTCTGAGC  ----------  ----------  ----------  TGGGCTCT    CCTGCTGCA   GAGCCGGTC   2177
Consensus          CMCAGTGSTG  CTGMCTGAGC  ----------  ----------  TGCCKGYKYT  YSMTGSTGYA  KWGCMWGGKS             2350

UNC-6              ----------  ----------  ----------  ----------  ----------  ----------  ----------  ----------  ----------  1839
p78 na con         ----------  ----------  ----------  ----------  ----------  ----------  ----------  ----------  ----------  1927
mo p78 na con      GATGT-AAGA  ACTGTGAAT-  ----------  ----------  TTTTGGC-C   TGCNNCCTGG  GCCAGGGNA              2097
p75 na con         CCTCTCACGT  GCTGCACATG  TGCTCCTC    AGCTCTCTGT  GCC--CCTTT                                     2225
Consensus          SMTSTCAMGW  RCTGTYRMATG TKYTGSKCTC  WGCNNYCTGK  GCCAGSSKNW                                     2400
```

Fig. 19p m p78, p78, p75, unc-6 Formatted Alignment

```
UNC-6            ------------ ------------ ------------ ------------ ------------   1839
p78 na con       ------------ ------------ ------------ ------------ ------------   1927
mo p78 na con    ACCAATCCAC   CACCAGACAC   TA-GTC-ACG   CCCCCTCCT    TTCTCCAT-C     2144
p75 na con       TCTTGTGCAG   CA-GAGACGG   GAGGTOGGTT   TCTTCCATCC   CGTTGCACAC     2274
Consensus        WCYWRTSCAS   CACSAGACRS   KAGGTCGRYK   YCYYCCWYCY   YKCTSCAYAC     2450

UNC-6            ------------ ------------ ------------ ------------ ------------   1839
p78 na con       ------------ ------------ ------------ ------------ ------------   1927
mo p78 na con    AC---CC-GC   TGTCTAG-GA   --ATTC----   ------------ ------------   2163
p75 na con       ACGGACGGC    TGGGTGGAGA   CCATTCCAGG   CTTGCAGGACC  GGCCCCAGGA     2324
Consensus        ACGGACGGC    TGKSTRGAGA   CCATYCAGG    CTGCAGGACC   GGCCCCAGGA     2500

UNC-6            ------------ ------------ ------------ ------------ ------------   1839
p78 na con       ------------ ------------ ------------ ------------ ------------   1927
mo p78 na con    ------------ ------------ ------------ ------------ ------------   2163
p75 na con       GCTCCCCTGG   GAGAACCAAG   TGACCTTTCT   CCAGGCCTGA   TCCTGCAGGA     2374
Consensus        GCTCCCCTGG   GAGAACCAAG   TGACCTTTCT   CCAGGCCTGA   TCCTGCAGGA     2550
```

Fig. 19q m p78, p78, p75, unc-6 Formatted Alignment

| | | | | | | |
|---|---|---|---|---|---|---|
| UNC-6 | ---------- | ---------- | ---------- | ---------- | ---------- | 1839 |
| p78 na con | ---------- | ---------- | ---------- | ---------- | ---------- | 1927 |
| mo p78 na con | ---------- | ---------- | ---------- | ---------- | ---------- | 2163 |
| p75 na con | CCTCAGCTTT | ACATGGACTG | GTCGTGCCGC | CCAGGGGCAG | GGCCCATGA | 2424 |
| Consensus | CCTCAGCTTT | ACATGGACTG | GTCGTGCCGC | CCAGGGGCAG | GGCCCATGA | 2600 |

| | | | | | | |
|---|---|---|---|---|---|---|
| UNC-6 | ---------- | ---------- | ---------- | ---------- | ---------- | 1839 |
| p78 na con | ---------- | ---------- | ---------- | ---------- | ---------- | 1927 |
| mo p78 na con | ---------- | ---------- | ---------- | ---------- | ---------- | 2163 |
| p75 na con | AGTCTTGGG | ACAGCCAGG | CTGTTGCCA | CCACCCACA | GAGCTGTTCT | 2474 |
| Consensus | AGTCTTGGG | ACAGCCAGG | CTGTTGCCA | CCACCCACA | GAGCTGTTCT | 2650 |

| | | | | | | |
|---|---|---|---|---|---|---|
| UNC-6 | ---------- | ---------- | ---------- | ---------- | ---------- | 1839 |
| p78 na con | ---------- | ---------- | ---------- | ---------- | ---------- | 1927 |
| mo p78 na con | ---------- | ---------- | ---------- | ---------- | ---------- | 2163 |
| p75 na con | GAGCAGGGG | CAGGGTCTG | CCTGTCCTG | TCGTGGTCC | AGGTGACCA | 2524 |
| Consensus | GAGCAGGGG | CAGGGTCTG | CCTGTCCTG | TCGTGGTCC | AGGTGACCA | 2700 |

Fig. 19r m p78, p78, p75, unc-6 Formatted Alignment

```
unc-6       ---------- ---------- ---------- ---------- ----------  1839
p78 na con  ---------- ---------- ---------- ---------- ----------  1927
mo p78 na con ---------- ---------- ---------- ---------- ----------  2163
p75 na con  WCAGGAAAGA AGTTTCCT GACCAACTTC CAGTCTTTCA CAGTCTCTGA  2574
Consensus   WCAGGAAAGA AGTTTCCT GACCAACTTC CAGTCTTTCA CAGTCTCTGA  2750 unc-6       ---------- ---------- ---------- ---------- ----------  1839
p78 na con  ---------- ---------- ---------- ---------- ----------  1927
mo p78 na con ---------- ---------- ---------- ---------- ----------  2163
p75 na con  TGCTCTGTGT ACCTTGGCCG TGCCAGAGT GCAGAGGCAG AGGTGGCAGG  2624
Consensus   TGCTCTGTGT ACCTTGGCCG TGCCAGAGT GCAGAGGCAG AGGTGGCAGG  2800 unc-6       ---------- ---------- ---------- ---------- ----------  1839
p78 na con  ---------- ---------- ---------- ---------- ----------  1927
mo p78 na con ---------- ---------- ---------- ---------- ----------  2163
p75 na con  AAGAGAGAG AGTTTCCT GACCAACTTC CAGTCTTTCA TTTCTTCTKC  2674
Consensus   AAGAGAGAG AGTTTCCT GACCAACTTC CAGTCTTTCA TTTCTTCTKC  2850
```

Fig. 19s m p78, p78, p75, unc-6 Formatted Alignment

```
UNC-6         ------------  ------------  ------------  ------------  ------------  1839
p78 na con    ------------  ------------  ------------  ------------  ------------  1927
mo p78 na con ------------  ------------  ------------  ------------  ------------  2163
p75 na con    ATACTGTATT    AGTCTCCAGT    TCAAACAGAC    ATCAGTTTCT    TTCCACGTTG    2724
Consensus     ATACTGTATT    AGTCTCCAGT    TCAAACAGAC    ATCAGTTTCT    TTCCACGTTG    2900

UNC-6         ------------  ------------  ------------  ------------  ------------  1839
p78 na con    ------------  ------------  ------------  ------------  ------------  1927
mo p78 na con ------------  ------------  ------------  ------------  ------------  2163
p75 na con    AGTTATAGT     GGTCTCGAYG    TAATAAACAT    GAATGCAAAT    AATAAAAAAA    2774
Consensus     AGTTATAGT     GGTCTCGAYG    TAATAAACAT    GAATGCAAAT    AATAAAAAAA    2950

UNC-6         ------------                                                          1839
p78 na con    ------------                                                          1927
mo p78 na con ------------                                                          2163
p75 na con    AAAAAAAA                                                              2783
Consensus     AAAAAAAA                                                              2959
```

Fig. 19t

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TAYGGNAARA CNTGGGT                                      17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCYTCYTGYT CRTTYTG                                      17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TGGGTNCCNT TYCARTT                                      17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CKRCARTTNA GRCARAC                                                                                              17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CKRCARTTNA GRCAYAC                                                                                              17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CKRCARTTYA ARCARAC                                                                                              17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CKRCARTTYA ARCAYAC                                                                                              17

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TGGGTNCCNT AYCARTAYTA                                                                                           20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCRTGNCCRT TRCAYTTRCA                                                                                           20

(2) INFORMATION FOR SEQ ID NO:10:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:10:

TCTACTCCAC GCAGTGCCGC                                                                                   20

( 2 ) INFORMATION FOR SEQ ID NO:11:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:11:

TGCTTGGTGA TGGCGGCGCG                                                                                   20

( 2 ) INFORMATION FOR SEQ ID NO:12:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:12:

GTACAACAAG CCGAGCCG                                                                                     18

( 2 ) INFORMATION FOR SEQ ID NO:13:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:13:

AGTCGTCCTC GTTCTC                                                                                       16

( 2 ) INFORMATION FOR SEQ ID NO:14:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:14:

TCTACGGCAA GCCCAGCAAG                                                                                   20

( 2 ) INFORMATION FOR SEQ ID NO:15:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear

5,565,331

37

-continued

38

( i i ) MOLECULE TYPE: cDNA ( x i ) SEQUENCE DESCRIPTION: SEQ ID NO:15:

CGTCCTCCTC GCCAGCCT                                                                                             1 8

( 2 ) INFORMATION FOR SEQ ID NO:16:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

ACCTGACGTG CTGGCAGTCC                                                                                           2 0

( 2 ) INFORMATION FOR SEQ ID NO:17:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

CCGTGTTGTG CTTGCAGTCG                                                                                           2 0

( 2 ) INFORMATION FOR SEQ ID NO:18:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:18:

CCGAGTTCGT CAACGCC                                                                                              1 7

( 2 ) INFORMATION FOR SEQ ID NO:19:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:19:

CGTTCTAGAT GCCGTTC                                                                                              1 7

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:20:

CAAAGCCTCC AAGGGGAAGC                                                                      20

( 2 ) INFORMATION FOR SEQ ID NO:21:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:21:

AGATCCACAT CCTGAAAGCG                                                                      20

( 2 ) INFORMATION FOR SEQ ID NO:22:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:22:

ACAAACAGGG CAGCAACCGG                                                                      20

( 2 ) INFORMATION FOR SEQ ID NO:23:

( i ) SEQUENCE CHARACTERISTICS:
       ( A ) LENGTH: 45 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:23:

AGAGAGAGAG AGAACTAGTC TCGAGCTTCC ATCCCTCAAT ACGAG                                           45

( 2 ) INFORMATION FOR SEQ ID NO:24:

( i ) SEQUENCE CHARACTERISTICS:
       ( A ) LENGTH: 45 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:24:

AGAGAGAGAG AGAACTAGTC TCGAGGTAGA GGTCGGTGAG GCCAT                                           45

( 2 ) INFORMATION FOR SEQ ID NO:25:

( i ) SEQUENCE CHARACTERISTICS:
       ( A ) LENGTH: 45 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:25:

AGAGAGAGAG AGAACTAGTC TCGAGTCCGT TCACACGATA TGTAT                                           45

( 2 ) INFORMATION FOR SEQ ID NO:26:

( i ) SEQUENCE CHARACTERISTICS:
( A ) LENGTH: 605 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:26:

```
Met Pro Arg Arg Gly Ala Glu Gly Pro Leu Ala Leu Leu Leu Ala Ala
 1           5              10                  15

Ala Trp Leu Ala Gln Pro Leu Arg Gly Tyr Pro Xaa Leu Asn Met
            20              25              30

Phe Ala Val Gln Thr Xaa Ala Asp Pro Cys Tyr Asp Glu His Gly Leu
         35              40                  45

Pro Xaa Arg Cys Ile Pro Asp Phe Val Asn Ser Ala Phe Gly Lys Glu
     50              55                  60

Val Lys Val Ser Ser Thr Cys Gly Lys Pro Pro Ser Arg Tyr Cys Val
 65              70              75                  80

Val Thr Glu Lys Gly Glu Glu Gln Val Arg Ser Cys His Leu Cys Asn
                 85              90                  95

Ala Ser Asp Pro Lys Arg Ala His Pro Pro Ser Phe Leu Thr Asp Leu
             100             105                 110

Asn Asn Pro His Asn Leu Thr Cys Trp Gln Ser Asp Ser Tyr Val Gln
             115             120                 125

Tyr Pro His Asn Val Thr Leu Thr Leu Ser Leu Gly Lys Lys Phe Glu
     130             135                 140

Val Thr Tyr Val Ser Leu Gln Phe Cys Ser Pro Arg Pro Glu Ser Met
 145                 150             155                 160

Ala Ile Tyr Lys Ser Met Asp Tyr Gly Lys Thr Trp Val Pro Phe Gln
                 165             170                 175

Phe Tyr Ser Thr Gln Cys Arg Lys Met Tyr Asn Lys Pro Ser Arg Ala
             180             185                 190

Ala Ile Thr Lys Gln Asn Glu Gln Glu Ala Ile Cys Thr Asp Ser His
             195             200             205

Thr Asp Val Arg Pro Leu Ser Gly Gly Leu Ile Ala Phe Ser Thr Leu
 210                 215                 220

Asp Gly Arg Pro Thr Ala His Asp Phe Asp Asn Ser Pro Val Leu Gln
 225             230                 235                 240

Asp Trp Val Thr Ala Thr Asp Ile Lys Val Thr Phe Ser Arg Leu His
             245                 250                 255

Thr Phe Gly Asp Glu Asn Glu Asp Asp Ser Glu Leu Ala Arg Asp Ser
             260                 265                 270

Tyr Phe Tyr Ala Val Ser Asp Leu Gln Val Gly Gly Arg Cys Lys Cys
         275                 280             285

Asn Gly His Ala Ser Arg Cys Val Arg Asp Arg Asp Asp Asn Leu Val
     290                 295             300

Cys Asp Cys Lys His Asn Thr Ala Gly Pro Glu Cys Asp Arg Cys Lys
 305                 310             315                 320

Pro Phe His Tyr Asp Arg Pro Trp Gln Arg Ala Thr Ala Arg Glu Ala
             325                 330                 335

Asn Glu Cys Val Ala Cys Asn Cys Asn Leu His Ala Arg Arg Cys Arg
             340                 345                 350

Phe Asn Met Glu Leu Tyr Lys Leu Ser Gly Arg Lys Ser Gly Gly Val
         355                 360             365

Cys Leu Asn Cys Arg His Asn Thr Ala Gly Arg His Cys His Tyr Cys
```

|  |  |  | 370 |  |  |  |  | 375 |  |  |  |  | 380 |  |  |
|---|---|---|---|---|---|---|---|---|---|---|---|---|---|---|---|

Lys Glu Gly Phe Tyr Arg Asp Leu Ser Lys Pro Ile Ser His Arg Lys
385                     390                 395                         400

Ala Cys Lys Glu Cys Asp Cys His Pro Val Gly Ala Ala Gly Gln Thr
            405                 410                     415

Cys Asn Gln Thr Thr Gly Gln Cys Pro Cys Lys Asp Gly Val Thr Gly
                420                 425                 430

Ile Thr Cys Asn Arg Cys Ala Lys Gly Tyr Gln Gln Ser Arg Ser Pro
        435                 440                 445

Ile Ala Pro Cys Ile Lys Ile Pro Ala Ala Pro Pro Thr Ala Ala
450                 455                 460

Ser Ser Thr Glu Glu Pro Ala Asp Cys Asp Ser Tyr Cys Lys Ala Ser
465                 470                 475                     480

Lys Gly Lys Leu Lys Ile Asn Met Lys Lys Tyr Cys Lys Lys Asp Tyr
                485                 490                     495

Ala Val Gln Ile His Ile Leu Lys Ala Glu Lys Asn Ala Asp Trp Trp
            500                 505                 510

Lys Phe Thr Val Asn Ile Ile Ser Val Tyr Lys Gln Gly Ser Asn Arg
        515                 520                 525

Leu Arg Arg Gly Asp Gln Thr Leu Trp Val His Ala Lys Asp Ile Ala
    530                 535                 540

Cys Lys Cys Pro Lys Val Lys Pro Met Lys Lys Tyr Leu Leu Leu Gly
545                 550                 555                     560

Ser Thr Glu Asp Ser Pro Asp Gln Ser Gly Ile Ile Ala Asp Lys Ser
                565                 570                     575

Ser Leu Val Ile Gln Trp Arg Asp Thr Trp Ala Arg Arg Leu Arg Lys
            580                 585                 590

Phe Gln Gln Arg Glu Lys Lys Gly Lys Cys Arg Lys Ala
    595                 600                 605

( 2 ) INFORMATION FOR SEQ ID NO:27:

( i ) SEQUENCE CHARACTERISTICS:
    ( A ) LENGTH: 581 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:27:

Leu Arg Leu Leu Leu Thr Thr Ser Val Leu Arg Leu Ala Arg Ala Ala
1               5                   10                  15

Asn Pro Phe Val Ala Gln Gln Thr Pro Pro Asp Pro Cys Tyr Asp Glu
            20                  25                  30

Ser Gly Ala Pro Pro Arg Cys Ile Pro Glu Phe Val Asn Ala Ala Phe
        35                  40                  45

Gly Lys Glu Val Gln Ala Ser Ser Thr Cys Gly Lys Pro Pro Thr Arg
    50                  55                  60

His Cys Asp Ala Ser Asp Pro Arg Arg Ala His Pro Pro Ala Tyr Leu
65              70                  75                      80

Thr Asp Leu Asn Thr Ala Ala Asn Met Thr Cys Trp Arg Ser Glu Thr
                85                  90                  95

Leu His His Leu Pro His Asn Val Thr Leu Thr Leu Ser Leu Gly Lys
            100                 105                 110

Lys Phe Glu Val Val Tyr Val Ser Leu Gln Phe Cys Ser Pro Arg Pro
        115                 120                 125

```
Glu  Ser  Thr  Ala  Ile  Phe  Lys  Ser  Met  Asp  Tyr  Gly  Lys  Thr  Trp  Val
          130                 135                 140
Pro  Tyr  Gln  Tyr  Tyr  Ser  Ser  Gln  Cys  Arg  Lys  Ile  Tyr  Gly  Lys  Pro
145                      150                 155                           160
Ser  Lys  Ala  Thr  Val  Thr  Lys  Gln  Asn  Glu  Gln  Glu  Ala  Leu  Cys  Thr
               165                      170                      175
Asp  Gly  Leu  Thr  Asp  Leu  Tyr  Pro  Leu  Thr  Gly  Gly  Leu  Ile  Ala  Phe
               180                 185                           190
Ser  Thr  Leu  Asp  Gly  Arg  Pro  Ser  Ala  Gln  Asp  Phe  Asp  Ser  Ser  Pro
          195                      200                 205
Val  Leu  Gln  Asp  Trp  Val  Thr  Ala  Thr  Asp  Ile  Arg  Val  Val  Phe  Ser
     210                      215                      220
Arg  Pro  His  Leu  Phe  Arg  Glu  Leu  Gly  Gly  Arg  Glu  Ala  Gly  Glu  Glu
225                           230                 235                      240
Asp  Gly  Gly  Ala  Gly  Ala  Thr  Pro  Tyr  Tyr  Ser  Val  Gly  Glu  Leu
                    245                 250                      255
Gln  Val  Gly  Gly  Arg  Cys  Lys  Cys  Asn  Gly  His  Ala  Ser  Arg  Cys  Val
               260                 265                      270
Lys  Asp  Lys  Glu  Gln  Lys  Leu  Val  Cys  Asp  Cys  Lys  His  Asn  Thr  Glu
          275                 280                 285
Gly  Pro  Glu  Cys  Asp  Arg  Cys  Lys  Pro  Phe  His  Tyr  Asp  Arg  Pro  Trp
     290                      295                 300
Gln  Arg  Ala  Ser  Ala  Arg  Glu  Ala  Asn  Glu  Cys  Leu  Ala  Cys  Asn  Cys
305                      310                 315                           320
Asn  Leu  His  Ala  Arg  Arg  Cys  Arg  Phe  Asn  Met  Glu  Leu  Tyr  Lys  Leu
                    325                 330                      335
Ser  Gly  Arg  Lys  Ser  Gly  Gly  Val  Cys  Leu  Asn  Cys  Arg  His  Asn  Thr
               340                 345                      350
Ala  Gly  Arg  His  Cys  His  Tyr  Cys  Lys  Glu  Gly  Phe  Tyr  Arg  Asp  Leu
               355                 360                 365
Ser  Lys  Ser  Ile  Thr  Asp  Arg  Lys  Ala  Cys  Lys  Ala  Cys  Asp  Cys  His
     370                      375                 380
Pro  Val  Gly  Ala  Ala  Gly  Lys  Thr  Cys  Asn  Gln  Thr  Thr  Gly  Gln  Cys
385                      390                 395                           400
Pro  Cys  Lys  Asp  Gly  Val  Thr  Gly  Leu  Thr  Cys  Asn  Arg  Cys  Ala  Lys
               405                 410                      415
Gly  Phe  Gln  Gln  Ser  Arg  Ser  Pro  Val  Ala  Pro  Cys  Ile  Lys  Ile  Pro
          420                 425                      430
Ala  Ile  Asn  Pro  Thr  Ser  Leu  Val  Thr  Ser  Thr  Glu  Ala  Pro  Ala  Asp
          435                 440                 445
Cys  Asp  Ser  Tyr  Cys  Lys  Pro  Ala  Lys  Gly  Asn  Tyr  Lys  Ile  Asn  Met
     450                 455                 460
Lys  Lys  Tyr  Cys  Lys  Lys  Asp  Tyr  Val  Val  Gln  Val  Asn  Ile  Leu  Glu
465                      470                 475                      480
Met  Glu  Thr  Val  Ala  Asn  Trp  Ala  Lys  Phe  Thr  Ile  Asn  Ile  Leu  Ser
               485                 490                      495
Val  Tyr  Lys  Cys  Arg  Asp  Glu  Arg  Val  Lys  Arg  Gly  Asp  Asn  Phe  Leu
               500                 505                      510
Trp  Ile  His  Leu  Lys  Asp  Leu  Ser  Cys  Lys  Cys  Pro  Lys  Ile  Gln  Ile
          515                 520                      525
Ser  Lys  Lys  Tyr  Leu  Val  Met  Gly  Ile  Ser  Glu  Asn  Ser  Thr  Asp  Arg
     530                 535                      540
Pro  Gly  Leu  Met  Ala  Asp  Lys  Asn  Ser  Leu  Val  Ile  Gln  Trp  Arg  Asp
```

|     | 545 |     |     |     | 550 |     |     |     |     | 555 |     |     |     |     | 560 |
| --- | --- | --- | --- | --- | --- | --- | --- | --- | --- | --- | --- | --- | --- | --- | --- |
| Ala | Trp | Thr | Arg | Arg | Leu | Arg | Lys | Leu | Gln | Arg | Arg | Glu | Lys | Lys | Gly |
|     |     |     |     | 565 |     |     |     |     | 570 |     |     |     |     | 575 |     |
| Lys | Cys | Val | Lys | Pro |
|     |     |     |     | 580 |

( 2 ) INFORMATION FOR SEQ ID NO:28:

( i ) SEQUENCE CHARACTERISTICS:
        ( A ) LENGTH: 271 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

| Asn | Cys | Phe | Cys | Tyr | Gly | His | Ala | Ser | Glu | Cys | Ala | Pro | Val | Asp | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Val | Asn | Glu | Glu | Val | Glu | Gly | Met | Val | His | Gly | His | Cys | Met | Cys | Arg |
|     |     |     | 20  |     |     |     |     | 25  |     |     |     |     | 30  |     |     |
| His | Asn | Thr | Lys | Gly | Leu | Asn | Cys | Glu | Leu | Cys | Met | Asp | Phe | Tyr | His |
|     |     |     | 35  |     |     |     |     | 40  |     |     |     |     | 45  |     |     |
| Asp | Leu | Pro | Trp | Arg | Pro | Ala | Glu | Gly | Arg | Asn | Ser | Asn | Ala | Cys | Lys |
|     |     | 50  |     |     |     |     | 55  |     |     |     |     | 60  |     |     |     |
| Lys | Cys | Asn | Cys | Asn | Glu | His | Ser | Ser | Ser | Cys | His | Phe | Asp | Met | Ala |
| 65  |     |     |     |     | 70  |     |     |     |     | 75  |     |     |     |     | 80  |
| Val | Phe | Leu | Ala | Thr | Gly | Asn | Val | Ser | Gly | Gly | Val | Cys | Asp | Asn | Cys |
|     |     |     |     | 85  |     |     |     |     | 90  |     |     |     |     | 95  |     |
| Gln | His | Asn | Thr | Met | Gly | Arg | Asn | Cys | Glu | Gln | Cys | Lys | Pro | Phe | Tyr |
|     |     |     | 100 |     |     |     |     | 105 |     |     |     |     | 110 |     |     |
| Phe | Gln | His | Pro | Glu | Arg | Asp | Ile | Arg | Asp | Pro | Asn | Leu | Cys | Glu | Pro |
|     |     |     | 115 |     |     |     |     | 120 |     |     |     |     | 125 |     |     |
| Cys | Thr | Cys | Asp | Pro | Ala | Gly | Ser | Glu | Asn | Gly | Gly | Ile | Cys | Asp | Gly |
|     |     | 130 |     |     |     |     | 135 |     |     |     |     | 140 |     |     |     |
| Tyr | Thr | Asp | Phe | Ser | Val | Gly | Leu | Ile | Ala | Gly | Gln | Cys | Arg | Cys | Lys |
| 145 |     |     |     |     | 150 |     |     |     |     | 155 |     |     |     |     | 160 |
| Leu | His | Val | Glu | Gly | Glu | Arg | Cys | Asp | Val | Cys | Lys | Glu | Gly | Phe | Tyr |
|     |     |     |     | 165 |     |     |     |     | 170 |     |     |     |     | 175 |     |
| Asp | Leu | Ser | Ala | Glu | Asp | Pro | Tyr | Gly | Cys | Lys | Ser | Cys | Ala | Cys | Asn |
|     |     |     | 180 |     |     |     |     | 185 |     |     |     |     | 190 |     |     |
| Pro | Leu | Gly | Thr | Ile | Pro | Gly | Gly | Asn | Pro | Cys | Asp | Ser | Glu | Thr | Gly |
|     |     | 195 |     |     |     |     | 200 |     |     |     |     | 205 |     |     |     |
| Tyr | Cys | Tyr | Cys | Lys | Arg | Leu | Val | Thr | Gly | Gln | Arg | Cys | Asp | Gln | Cys |
|     | 210 |     |     |     |     | 215 |     |     |     |     | 220 |     |     |     |     |
| Leu | Pro | Gln | His | Trp | Gly | Leu | Ser | Asn | Asp | Leu | Asp | Gly | Cys | Arg | Pro |
| 225 |     |     |     |     | 230 |     |     |     |     | 235 |     |     |     |     | 240 |
| Cys | Asp | Cys | Asp | Leu | Gly | Gly | Ala | Leu | Asn | Asn | Ser | Cys | Ser | Glu | Asp |
|     |     |     |     | 245 |     |     |     |     | 250 |     |     |     |     | 255 |     |
| Ser | Gly | Gln | Cys | Ser | Cys | Leu | Pro | His | Met | Ile | Gly | Arg | Gln | Cys |     |
|     |     |     | 260 |     |     |     |     | 265 |     |     |     |     | 270 |     |     |

( 2 ) INFORMATION FOR SEQ ID NO:29:

( i ) SEQUENCE CHARACTERISTICS:
        ( A ) LENGTH: 279 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

| Asn | Cys | Phe | Cys | Tyr | Gly | His | Ala | Ser | Glu | Cys | Ala | Pro | Val | Asp | Gly |
|---|---|---|---|---|---|---|---|---|---|---|---|---|---|---|---|
| 1 | | | | 5 | | | | | 10 | | | | | 15 | |

| Phe | Asn | Glu | Glu | Val | Glu | Gly | Met | Val | His | Gly | His | Cys | Met | Cys | Arg |
|---|---|---|---|---|---|---|---|---|---|---|---|---|---|---|---|
| | | | 20 | | | | | 25 | | | | | 30 | | |

| His | Asn | Thr | Lys | Gly | Leu | Asn | Cys | Glu | Leu | Cys | Met | Asp | Phe | Tyr | His |
|---|---|---|---|---|---|---|---|---|---|---|---|---|---|---|---|
| | | 35 | | | | | 40 | | | | | 45 | | | |

| Asp | Leu | Pro | Trp | Arg | Pro | Ala | Glu | Gly | Arg | Asn | Ser | Asn | Ala | Cys | Lys |
|---|---|---|---|---|---|---|---|---|---|---|---|---|---|---|---|
| | 50 | | | | | 55 | | | | 60 | | | | | |

| Lys | Cys | Asn | Cys | Asn | Glu | His | Ser | Ile | Ser | Cys | His | Phe | Asp | Met | Ala |
|---|---|---|---|---|---|---|---|---|---|---|---|---|---|---|---|
| 65 | | | | | 70 | | | | | 75 | | | | | 80 |

| Val | Tyr | Leu | Ala | Thr | Gly | Asn | Val | Ser | Gly | Gly | Val | Cys | Asp | Asp | Cys |
|---|---|---|---|---|---|---|---|---|---|---|---|---|---|---|---|
| | | | | 85 | | | | | 90 | | | | | 95 | |

| Gln | His | Asn | Thr | Met | Gly | Arg | Asn | Cys | Glu | Gln | Cys | Lys | Pro | Phe | Tyr |
|---|---|---|---|---|---|---|---|---|---|---|---|---|---|---|---|
| | | | 100 | | | | | 105 | | | | | 110 | | |

| Tyr | Gln | His | Pro | Glu | Arg | Asp | Ile | Arg | Asp | Pro | Asn | Phe | Cys | Glu | Arg |
|---|---|---|---|---|---|---|---|---|---|---|---|---|---|---|---|
| | | 115 | | | | | 120 | | | | | 125 | | | |

| Cys | Thr | Cys | Asp | Pro | Ala | Gly | Ser | Gln | Asn | Glu | Gly | Ile | Cys | Asp | Ser |
|---|---|---|---|---|---|---|---|---|---|---|---|---|---|---|---|
| | 130 | | | | | 135 | | | | | 140 | | | | |

| Tyr | Thr | Asp | Phe | Ser | Thr | Gly | Leu | Ile | Ala | Gly | Gln | Cys | Arg | Cys | Lys |
|---|---|---|---|---|---|---|---|---|---|---|---|---|---|---|---|
| 145 | | | | | 150 | | | | | 155 | | | | | 160 |

| Leu | Asn | Val | Glu | Gly | Glu | His | Cys | Asp | Val | Cys | Lys | Glu | Gly | Phe | Tyr |
|---|---|---|---|---|---|---|---|---|---|---|---|---|---|---|---|
| | | | | 165 | | | | | 170 | | | | | 175 | |

| Asp | Leu | Ser | Ser | Glu | Asp | Pro | Phe | Gly | Cys | Lys | Ser | Cys | Ala | Cys | Asn |
|---|---|---|---|---|---|---|---|---|---|---|---|---|---|---|---|
| | | | 180 | | | | | 185 | | | | | 190 | | |

| Pro | Leu | Gly | Thr | Ile | Pro | Gly | Gly | Asn | Pro | Cys | Asp | Ser | Glu | Thr | Gly |
|---|---|---|---|---|---|---|---|---|---|---|---|---|---|---|---|
| | | 195 | | | | | 200 | | | | | 205 | | | |

| His | Cys | Tyr | Cys | Lys | Arg | Leu | Val | Thr | Gly | Gln | His | Cys | Asp | Gln | Cys |
|---|---|---|---|---|---|---|---|---|---|---|---|---|---|---|---|
| | 210 | | | | | 215 | | | | | 220 | | | | |

| Leu | Pro | Glu | His | Trp | Gly | Leu | Ser | Asn | Asp | Leu | Asp | Gly | Cys | Arg | Pro |
|---|---|---|---|---|---|---|---|---|---|---|---|---|---|---|---|
| 225 | | | | | 230 | | | | | 235 | | | | | 240 |

| Cys | Asp | Cys | Asp | Leu | Gly | Gly | Ala | Leu | Asn | Asn | Ser | Cys | Phe | Ala | Glu |
|---|---|---|---|---|---|---|---|---|---|---|---|---|---|---|---|
| | | | | 245 | | | | | 250 | | | | | 255 | |

| Ser | Gly | Gln | Cys | Ser | Cys | Arg | Pro | His | Met | Ile | Gly | Arg | Gln | Cys | Asn |
|---|---|---|---|---|---|---|---|---|---|---|---|---|---|---|---|
| | | | 260 | | | | | 265 | | | | | 270 | | |

| Glu | Val | Glu | Pro | Gly | Tyr | Tyr |
|---|---|---|---|---|---|---|
| | | 275 | | | | |

( 2 ) INFORMATION FOR SEQ ID NO:30:

( i ) SEQUENCE CHARACTERISTICS:
( A ) LENGTH: 273 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:30:

| Ser | Cys | Ser | Cys | Tyr | Gly | His | Ala | Ser | Gln | Cys | Leu | Pro | Leu | Asp | Pro |
|---|---|---|---|---|---|---|---|---|---|---|---|---|---|---|---|
| 1 | | | | 5 | | | | | 10 | | | | | 15 | |

| Ala | Phe | Ser | Gln | Ala | Asp | Asn | Glu | Asp | Gly | Met | Val | His | Gly | Arg | Cys |
|---|---|---|---|---|---|---|---|---|---|---|---|---|---|---|---|
| | | | 20 | | | | | 25 | | | | | 30 | | |

| Glu | Cys | Thr | His | Asn | Thr | Lys | Gly | Met | Asn | Cys | Glu | Glu | Cys | Glu | Asp |
|---|---|---|---|---|---|---|---|---|---|---|---|---|---|---|---|
| | | 35 | | | | | 40 | | | | | 45 | | | |

```
Phe Phe Asn Asp Leu Pro Trp Lys Pro Ala Phe Gly Lys Lys Thr Asn
    50                  55                  60

Ala Cys Lys Lys Cys Glu Cys Asn Asp His Ala Val Ser Cys His Phe
65                  70                  75                  80

Asp Glu Ala Val Phe Thr Ala Ser Gly Phe Val Ser Gly Gly Val Cys
                85                  90                  95

Asp Asn Cys Leu His Asn Thr Arg Gly Gln His Cys Glu Glu Cys Met
            100                 105                 110

Pro Tyr Phe Tyr Arg Asp Pro Glu Gln Asp Ile Thr Ser Glu Arg Val
        115                 120                 125

Cys Gln Pro Cys Asp Cys Asp Pro Gln Gly Ser Ser Asp Asp Gly Ile
    130                 135                 140

Cys Asp Ser Leu Asn Glu Leu Glu Glu Gly Ala Val Ala Gly Ala Cys
145                 150                 155                 160

His Cys Lys Ala Phe Val Thr Gly Arg Arg Cys Asn Gln Cys Lys Asp
                165                 170                 175

Gly Tyr Trp Asn Leu Gln Ser Asp Asn Pro Glu Gly Cys Glu Pro Cys
            180                 185                 190

Thr Cys Asn Pro Leu Gly Thr Leu Asn Asn Ser Gly Cys Val Met Arg
        195                 200                 205

Thr Gly Glu Cys Lys Cys Lys Lys Tyr Val Thr Gly Lys Asp Cys Asn
    210                 215                 220

Gln Cys Met Pro Glu Thr Tyr Gly Leu Ser Glu Ser Pro Glu Gly Cys
225                 230                 235                 240

Ser Leu Cys Asn Cys Asp Ala Gly Gly Ser Tyr Asp Asn Tyr Cys Asp
                245                 250                 255

Val Ile Ser Gly Gln Cys Arg Cys Arg Pro His Met Thr Gly Arg Ser
            260                 265                 270

Cys
```

( 2 ) INFORMATION FOR SEQ ID NO:31:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Cys Lys Cys Asn Gly His Ala Ser Glu Cys Met Lys Asn Glu Phe Asp
1               5                   10                  15

Lys Leu Val Cys Asn Cys Lys His Asn Thr Tyr Gly Val Asp Cys Glu
            20                  25                  30

Lys Cys Leu Pro Phe Phe Asn Asp Arg Pro Trp Arg Arg Ala Thr Ala
        35                  40                  45

Glu Ser Ala Ser Glu Cys Leu Pro Cys Asp Cys Asn Gly Arg Ser Gln
    50                  55                  60

Glu Cys Tyr Phe Asp Pro Glu Leu Tyr Arg Ser Thr Gly His Gly Gly
65                  70                  75                  80

His Cys Thr Asn Cys Gln Asp Asn Thr Asp Gly Ala His Cys Glu Arg
                85                  90                  95

Cys Arg Glu Asn Phe Phe Arg Leu Gly Asn Asn Glu Ala Cys Ser Ser
            100                 105                 110

Cys His Cys Ser Pro Val Gly Ser Leu Ser Thr Gln Cys Asp Ser Tyr
```

|     |     |     | 115 |     |     |     | 120 |     |     |     | 125 |     |     |     |
|-----|-----|-----|-----|-----|-----|-----|-----|-----|-----|-----|-----|-----|-----|-----|
| Gly | Arg | Cys | Ser | Cys | Lys | Pro | Gly | Val | Met | Gly | Asp | Lys | Cys | Asp | Arg |
|     | 130 |     |     |     |     | 135 |     |     |     |     | 140 |     |     |     |
| Cys | Gln | Pro | Gly | Phe | His | Ser | Leu | Thr | Glu | Ala | Gly | Cys | Arg | Pro | Cys |
| 145 |     |     |     |     | 150 |     |     |     |     | 155 |     |     |     |     | 160 |
| Ser | Cys | Asp | Pro | Ser | Gly | Ser | Ile | Asp | Glu | Cys | Asn | Val | Glu | Thr | Gly |
|     |     |     |     | 165 |     |     |     |     | 170 |     |     |     |     | 175 |     |
| Arg | Cys | Val | Cys | Lys | Asp | Asn | Val | Glu | Gly | Phe | Asn | Cys | Glu | Arg | Cys |
|     |     |     | 180 |     |     |     |     | 185 |     |     |     |     | 190 |     |     |
| Lys | Pro | Gly | Phe | Phe | Asn | Leu | Glu | Ser | Ser | Asn | Pro | Arg | Gly | Cys | Thr |
|     |     | 195 |     |     |     |     | 200 |     |     |     |     | 205 |     |     |     |
| Pro | Cys | Phe | Cys | Phe | Gly | His | Ser | Ser | Val | Cys |     |     |     |     |     |
|     | 210 |     |     |     |     | 215 |     |     |     |     |     |     |     |     |     |

( 2 ) INFORMATION FOR SEQ ID NO:32:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

| Cys | Lys | Cys | Asn | Gly | His | Ala | Ser | Glu | Cys | Val | Lys | Asn | Glu | Phe | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Lys | Leu | Met | Cys | Asn | Cys | Lys | His | Asn | Thr | Tyr | Gly | Val | Asp | Cys | Glu |
|     |     |     | 20  |     |     |     | 25  |     |     |     | 30  |     |     |     |     |
| Lys | Cys | Leu | Pro | Phe | Phe | Asn | Asp | Arg | Pro | Trp | Arg | Arg | Ala | Thr | Ala |
|     |     | 35  |     |     |     | 40  |     |     |     | 45  |     |     |     |     |     |
| Glu | Ser | Ala | Ser | Glu | Ser | Leu | Pro | Cys | Asp | Cys | Asn | Gly | Arg | Ser | Gln |
|     | 50  |     |     |     |     | 55  |     |     |     | 60  |     |     |     |     |     |
| Glu | Cys | Tyr | Phe | Asp | Pro | Glu | Leu | Tyr | Arg | Ser | Thr | Gly | His | Gly | Gly |
| 65  |     |     |     |     | 70  |     |     |     | 75  |     |     |     |     | 80  |     |
| His | Cys | Thr | Asn | Cys | Arg | Asp | Asn | Thr | Asp | Gly | Ala | Lys | Cys | Glu | Arg |
|     |     |     |     | 85  |     |     |     |     | 90  |     |     |     |     | 95  |     |
| Cys | Arg | Glu | Asn | Phe | Phe | Arg | Leu | Gly | Asn | Thr | Glu | Ala | Cys | Ser | Pro |
|     |     |     | 100 |     |     |     | 105 |     |     |     | 110 |     |     |     |     |
| Cys | His | Cys | Ser | Pro | Val | Gly | Ser | Leu | Ser | Thr | Gln | Cys | Asp | Ser | Tyr |
|     |     | 115 |     |     |     | 120 |     |     |     | 125 |     |     |     |     |     |
| Gly | Arg | Cys | Ser | Cys | Lys | Pro | Gly | Val | Met | Gly | Asp | Lys | Cys | Asp | Arg |
|     | 130 |     |     |     |     | 135 |     |     |     |     | 140 |     |     |     |     |
| Cys | Gln | Pro | Gly | Phe | His | Ser | Leu | Thr | Glu | Ala | Gly | Cys | Arg | Pro | Cys |
| 145 |     |     |     |     | 150 |     |     |     |     | 155 |     |     |     |     | 160 |
| Ser | Cys | Asp | Leu | Arg | Gly | Ser | Thr | Asp | Glu | Cys | Asn | Val | Glu | Thr | Gly |
|     |     |     |     | 165 |     |     |     |     | 170 |     |     |     |     | 175 |     |
| Arg | Cys | Val | Cys | Lys | Asp | Asn | Val | Glu | Gly | Phe | Asn | Cys | Glu | Arg | Cys |
|     |     |     | 180 |     |     |     |     | 185 |     |     |     |     | 190 |     |     |
| Lys | Pro | Gly | Phe | Phe | Asn | Leu | Glu | Ser | Ser | Asn | Pro | Lys | Gly | Cys | Thr |
|     |     | 195 |     |     |     |     | 200 |     |     |     |     | 205 |     |     |     |
| Pro | Cys | Phe | Cys | Phe | Gly | His | Ser | Ser | Val | Cys |     |     |     |     |     |
|     | 210 |     |     |     |     | 215 |     |     |     |     |     |     |     |     |     |

( 2 ) INFORMATION FOR SEQ ID NO:33:

( i ) SEQUENCE CHARACTERISTICS:
        ( A ) LENGTH: 225 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

```
Cys Lys Cys Asn Gly His Ala Ser Lys Cys Val Pro Ser Thr Gly Met
  1               5                  10                  15

His Gly Glu Arg Thr Leu Val Cys Glu Cys Arg His Asn Thr Asp Gly
             20                  25                  30

Pro Asp Cys Asp Arg Cys Leu Pro Leu Tyr Asn Asp Leu Lys Trp Lys
         35                  40                  45

Arg Ser Thr Ser Thr Glu Val Asn Glu Cys Lys Ala Cys Asn Cys Asn
     50                  55                  60

Gly Leu Ala Asp Lys Cys Phe Phe Asp Ala Asn Leu Phe Asn Arg Thr
 65                  70                  75                  80

Gly His Gly Gly His Cys Leu Asp Cys Arg Glu Asn Arg Asp Gly Pro
                 85                  90                  95

Asn Cys Glu Arg Cys Lys Glu Asn Phe Tyr Met Arg Asp Asp Gly Tyr
            100                 105                 110

Cys Val Asn Cys Ala Cys Asp Pro Val Gly Ser Arg Ser Leu Gln Cys
            115                 120                 125

Asn Ser His Gly Lys Cys Gln Cys Lys Pro Gly Val Thr Gly Asp Lys
        130                 135                 140

Cys Asp Arg Cys Asp Asn Asn Tyr Tyr Gln Phe Gly Pro His Gly Cys
145                 150                 155                 160

Gln Gln Cys Gly Cys Asp Ser Gly Gly Ser His Gln Asn Thr Pro Ala
                165                 170                 175

Cys Asp Thr Glu Thr Gly Ile Cys Phe Cys Lys Glu Asn Val Glu Gly
            180                 185                 190

Arg Arg Cys Asn Glu Cys Lys Pro Gly Phe Phe Asn Leu Asp Lys Asn
        195                 200                 205

Asn Arg Phe Gly Cys Thr Pro Cys Phe Cys Tyr Gly His Thr Ser Glu
    210                 215                 220

Cys
225
```

( 2 ) INFORMATION FOR SEQ ID NO:34:

( i ) SEQUENCE CHARACTERISTICS:
( A ) LENGTH: 248 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:34:

```
Gln Glu Pro Glu Phe Ser Tyr Gly Cys Ala Glu Gly Ser Cys Tyr Pro
  1               5                  10                  15

Ala Thr Gly Asp Leu Leu Ile Gly Arg Ala Gln Lys Leu Ser Val Thr
             20                  25                  30

Ser Thr Cys Gly Leu His Lys Pro Glu Pro Tyr Cys Ile Val Ser His
         35                  40                  45

Leu Gln Glu Asp Lys Lys Cys Phe Ile Cys Asp Ser Arg Asp Pro Tyr
     50                  55                  60

His Glu Thr Leu Asn Pro Asp Ser His Leu Ile Glu Asn Val Val Thr
 65                  70                  75                  80
```

```
Thr  Phe  Ala  Pro  Asn  Arg  Leu  Lys  Ile  Trp  Trp  Gln  Ser  Glu  Asn  Gly
                85                       90                       95

Val  Glu  Asn  Val  Thr  Ile  Gln  Leu  Asp  Leu  Glu  Ala  Glu  Phe  His  Phe
               100                      105                      110

Thr  His  Leu  Ile  Met  Thr  Phe  Lys  Thr  Phe  Arg  Pro  Ala  Ala  Met  Leu
          115                      120                      125

Ile  Glu  Arg  Ser  Ser  Asp  Phe  Gly  Lys  Thr  Trp  Gly  Val  Tyr  Arg  Tyr
     130                      135                      140

Phe  Ala  Tyr  Asp  Cys  Glu  Ser  Ser  Phe  Pro  Gly  Ile  Ser  Thr  Gly  Pro
145                      150                      155                      160

Met  Lys  Lys  Val  Asp  Asp  Ile  Ile  Cys  Asp  Ser  Arg  Tyr  Ser  Asp  Ile
               165                      170                      175

Glu  Pro  Ser  Thr  Glu  Gly  Glu  Val  Ile  Phe  Arg  Ala  Leu  Asp  Pro  Ala
               180                      185                      190

Phe  Lys  Ile  Glu  Asp  Pro  Tyr  Ser  Pro  Arg  Ile  Gln  Asn  Leu  Leu  Lys
          195                      200                      205

Ile  Thr  Asn  Leu  Arg  Ile  Lys  Phe  Val  Lys  Leu  His  Thr  Leu  Gly  Asp
     210                      215                      220

Asn  Leu  Leu  Asp  Ser  Arg  Met  Glu  Ile  Arg  Glu  Lys  Tyr  Tyr  Tyr  Ala
225                      230                      235                      240

Val  Tyr  Asp  Met  Val  Val  Arg  Gly
               245
```

( 2 ) INFORMATION FOR SEQ ID NO:35:

( i ) SEQUENCE CHARACTERISTICS:
( A ) LENGTH: 249 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:35:

```
Ala  Gln  Glu  Pro  Glu  Phe  Ser  Tyr  Gly  Cys  Ala  Glu  Gly  Ser  Cys  Tyr
1                 5                       10                       15

Pro  Ala  Thr  Gly  Asp  Leu  Leu  Ile  Gly  Arg  Ala  Gln  Lys  Leu  Ser  Val
               20                       25                       30

Thr  Ser  Thr  Cys  Gly  Leu  His  Lys  Pro  Glu  Pro  Tyr  Cys  Ile  Val  Ser
          35                       40                       45

His  Leu  Gln  Glu  Asp  Lys  Lys  Cys  Phe  Ile  Cys  Asn  Ser  Gln  Asp  Pro
     50                       55                       60

Tyr  His  Glu  Thr  Leu  Asn  Pro  Asp  Ser  His  Leu  Ile  Glu  Asn  Val  Val
65                       70                       75                       80

Thr  Thr  Phe  Ala  Pro  Asn  Arg  Leu  Lys  Ile  Trp  Trp  Gln  Ser  Glu  Asn
               85                       90                       95

Gly  Val  Glu  Asn  Val  Thr  Ile  Gln  Leu  Asp  Leu  Glu  Ala  Glu  Phe  His
               100                      105                      110

Phe  Thr  His  Leu  Ile  Met  Thr  Phe  Lys  Thr  Phe  Arg  Pro  Ala  Ala  Met
          115                      120                      125

Leu  Ile  Glu  Arg  Ser  Ser  Asp  Phe  Gly  Lys  Thr  Trp  Gly  Val  Tyr  Arg
     130                      135                      140

Tyr  Phe  Ala  Tyr  Asp  Cys  Glu  Ala  Ser  Phe  Pro  Gly  Ile  Ser  Thr  Gly
145                      150                      155                      160

Pro  Met  Lys  Lys  Val  Asp  Asp  Ile  Ile  Cys  Asp  Ser  Arg  Tyr  Ser  Asp
               165                      170                      175
```

```
Ile Glu Pro Ser Thr Glu Gly Glu Val Ile Phe Arg Ala Leu Asp Pro
            180                 185                 190

Ala Phe Lys Ile Glu Asp Pro Tyr Ser Pro Arg Ile Gln Asn Leu Leu
        195                 200                 205

Lys Ile Thr Asn Leu Arg Ile Lys Phe Val Lys Leu His Thr Leu Gly
        210                 215                 220

Asp Asn Leu Leu Asp Ser Arg Met Glu Ile Arg Glu Lys Tyr Tyr Tyr
225                 230                 235                 240

Ala Val Tyr Asp Met Val Val Arg Gly
                245
```

(2) INFORMATION FOR SEQ ID NO:36:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Arg Arg Asp Arg Pro Lys Tyr Pro Pro Asn Lys Phe Ile Lys Thr His
1               5                   10                  15

Pro Cys Glu Arg Ser Ser Cys Tyr Pro Ala Thr Gly Asn Leu Leu Ile
            20                  25                  30

Gly Arg Glu Asn Arg Leu Thr Ala Ser Ser Thr Cys Gly Leu His Ser
            35                  40                  45

Pro Glu Arg Phe Cys Ile Leu Ser His Leu Gln Asp Lys Lys Cys Phe
        50                  55                  60

Leu Cys Asp Thr Arg Glu Glu Thr Lys His Asp Pro Tyr Lys Asn His
65                  70                  75                  80

Arg Ile Gly Gln Ile Ile Tyr Lys Thr Lys Pro Gly Thr Asn Ile Pro
                85                  90                  95

Thr Trp Trp Gln Ser Glu Asn Gly Lys Glu Asn Ala Thr Ile Gln Leu
            100                 105                 110

Asp Leu Glu Ala Glu Phe His Phe Thr His Leu Ile Ile Thr Phe Thr
        115                 120                 125

Thr Phe Arg Pro Ala Ala Met Tyr Ile Glu Arg Ser Phe Asp Phe Gly
    130                 135                 140

Gln Thr Trp His Ile Tyr Arg Tyr Phe Ala Tyr Asp Cys Lys Glu Ser
145                 150                 155                 160

Phe Pro Gly Val Pro Thr Val Leu Glu Asn Ile Thr Asp Val Met Cys
                165                 170                 175

Thr Ser Arg Tyr Ser Asn Val Glu Pro Ser Arg Asn Gly Glu Val Ile
            180                 185                 190

Phe Arg Val Leu Pro Pro Asn Ile Asn Val Thr Asp Pro Tyr Ala Glu
        195                 200                 205

His Val Gln Asn Gln Leu Lys Met Thr Asn Leu Arg Ile Gln Met Thr
    210                 215                 220

Lys Leu His Lys Leu Gly Asp Asn Leu Leu Asp Ser Arg Leu Glu Asn
225                 230                 235                 240

Glu Glu Lys Tyr Tyr Tyr Gly Ile Ser Asn Met Val Val Arg Gly
                245                 250                 255
```

(2) INFORMATION FOR SEQ ID NO:37:

(i) SEQUENCE CHARACTERISTICS:

(A) LENGTH: 251 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:37:

| Ala | Ala | Met | Asp | Glu | Cys | Ala | Asp | Glu | Gly | Gly | Arg | Pro | Gln | Arg | Cys |
|---|---|---|---|---|---|---|---|---|---|---|---|---|---|---|---|
| 1 | | | | 5 | | | | | 10 | | | | | 15 | |
| Met | Pro | Glu | Phe | Val | Asn | Ala | Ala | Phe | Asn | Val | Thr | Val | Val | Ala | Thr |
| | | | 20 | | | | 25 | | | | | 30 | | | |
| Asn | Thr | Cys | Gly | Thr | Pro | Pro | Glu | Glu | Tyr | Cys | Val | Gln | Thr | Gly | Val |
| | | 35 | | | | | 40 | | | | | 45 | | | |
| Thr | Gly | Val | Thr | Lys | Ser | Cys | His | Leu | Cys | Asp | Ala | Gly | Gln | Gln | His |
| | 50 | | | | | 55 | | | | | 60 | | | | |
| Leu | Gln | His | Gly | Ala | Ala | Phe | Leu | Thr | Asp | Tyr | Asn | Asn | Gln | Ala | Asp |
| 65 | | | | | 70 | | | | 75 | | | | | | 80 |
| Thr | Thr | Trp | Trp | Gln | Ser | Gln | Thr | Met | Leu | Ala | Gly | Val | Gln | Tyr | Pro |
| | | | | 85 | | | | | 90 | | | | | 95 | |
| Asn | Ser | Ile | Asn | Leu | Thr | Leu | His | Leu | Gly | Lys | Ala | Phe | Asp | Ile | Thr |
| | | | | 100 | | | | 105 | | | | | 110 | | |
| Tyr | Val | Arg | Leu | Lys | Phe | His | Thr | Ser | Arg | Pro | Glu | Ser | Phe | Ala | Ile |
| | | 115 | | | | | 120 | | | | | 125 | | | |
| Tyr | Lys | Arg | Thr | Arg | Glu | Asp | Gly | Pro | Trp | Ile | Pro | Tyr | Gln | Tyr | Tyr |
| | 130 | | | | | 135 | | | | | 140 | | | | |
| Ser | Gly | Ser | Cys | Glu | Asn | Thr | Tyr | Ser | Lys | Ala | Asn | Arg | Gly | Phe | Ile |
| 145 | | | | | 150 | | | | | 155 | | | | | 160 |
| Arg | Thr | Gly | Gly | Asp | Glu | Gln | Gln | Ala | Leu | Cys | Thr | Asp | Glu | Phe | Ser |
| | | | | 165 | | | | | 170 | | | | | 175 | |
| Asp | Ile | Ser | Pro | Leu | Thr | Gly | Gly | Asn | Val | Ala | Phe | Ser | Thr | Leu | Glu |
| | | | 180 | | | | | 185 | | | | | 190 | | |
| Gly | Arg | Pro | Ser | Ala | Tyr | Asn | Phe | Asp | Asn | Ser | Pro | Val | Leu | Gln | Glu |
| | | 195 | | | | | 200 | | | | | 205 | | | |
| Trp | Val | Thr | Ala | Thr | Asp | Ile | Arg | Val | Thr | Leu | Asn | Arg | Leu | Asn | Thr |
| | 210 | | | | | 215 | | | | | 220 | | | | |
| Phe | Gly | Asp | Glu | Val | Phe | Asn | Glu | Pro | Lys | Val | Leu | Lys | Ser | Tyr | Tyr |
| 225 | | | | | 230 | | | | | 235 | | | | | 240 |
| Tyr | Ala | Ile | Ser | Asp | Phe | Ala | Val | Gly | Gly | Arg | | | | | |
| | | | | 245 | | | | | 250 | | | | | | |

(2) INFORMATION FOR SEQ ID NO:38:

(i) SEQUENCE CHARACTERISTICS:
(A) LENGTH: 252 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:38:

| Gln | Ala | Ala | Met | Asp | Glu | Cys | Thr | Asp | Glu | Gly | Gly | Arg | Pro | Gln | Arg |
|---|---|---|---|---|---|---|---|---|---|---|---|---|---|---|---|
| 1 | | | | 5 | | | | | 10 | | | | | 15 | |
| Cys | Met | Pro | Glu | Phe | Val | Asn | Ala | Ala | Phe | Asn | Val | Thr | Val | Val | Ala |
| | | | 20 | | | | | 25 | | | | | 30 | | |
| Thr | Asn | Thr | Cys | Gly | Thr | Pro | Pro | Glu | Glu | Tyr | Cys | Val | Gln | Thr | Gly |
| | | | 35 | | | | | 40 | | | | | 45 | | |
| Val | Thr | Gly | Val | Thr | Lys | Ser | Cys | His | Leu | Cys | Asp | Ala | Gly | Gln | Pro |

```
                       50                        55                          60
His  Leu  Gln  His  Gly  Ala  Ala  Phe  Leu  Thr  Asp  Tyr  Asn  Asn  Gln  Ala
65                       70                       75                       80

Asp  Thr  Thr  Trp  Trp  Gln  Ser  Gln  Thr  Met  Leu  Ala  Gly  Val  Gln  Tyr
                    85                       90                       95

Pro  Ser  Ser  Ile  Asn  Leu  Thr  Leu  His  Leu  Gly  Lys  Ala  Phe  Asp  Ile
                    100                      105                      110

Thr  Tyr  Val  Arg  Leu  Lys  Phe  His  Thr  Ser  Arg  Pro  Glu  Ser  Phe  Ala
               115                      120                      125

Ile  Tyr  Lys  Arg  Thr  Arg  Glu  Asp  Gly  Pro  Trp  Ile  Pro  Tyr  Gln  Tyr
          130                      135                      140

Tyr  Ser  Gly  Ser  Cys  Glu  Asn  Thr  Tyr  Ser  Lys  Ala  Asn  Arg  Gly  Phe
145                      150                      155                      160

Ile  Arg  Thr  Gly  Gly  Asp  Glu  Gln  Gln  Ala  Leu  Cys  Thr  Asp  Glu  Phe
                    165                      170                      175

Ser  Asp  Phe  Ser  Pro  Leu  Thr  Gly  Gly  Asn  Val  Ala  Phe  Ser  Thr  Leu
               180                      185                      190

Glu  Gly  Arg  Pro  Ser  Ala  Tyr  Asn  Phe  Asp  Asn  Ser  Pro  Val  Leu  Gln
          195                      200                      205

Glu  Trp  Val  Thr  Ala  Thr  Asp  Ile  Arg  Val  Thr  Leu  Asn  Arg  Leu  Asn
     210                      215                      220

Thr  Phe  Gly  Asp  Glu  Val  Phe  Asn  Asp  Pro  Lys  Val  Leu  Lys  Ser  Tyr
225                      230                      235                      240

Tyr  Tyr  Ala  Ile  Ser  Asp  Phe  Ala  Val  Gly  Gly  Arg
                    245                      250
```

( 2 ) INFORMATION FOR SEQ ID NO:39:

( i ) SEQUENCE CHARACTERISTICS:
        ( A ) LENGTH: 264 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Arg  Pro  Pro  Ile  Asn  Ser  Ala  Gly  Gly  His  Glu  Leu  Arg  Gly  Thr  Thr
1                   5                        10                       15

Phe  Met  Pro  Ala  Leu  Glu  Cys  Tyr  Asp  Pro  Tyr  Gly  Arg  Pro  Gln  Lys
               20                       25                       30

Cys  Leu  Pro  Glu  Phe  Ile  Asn  Ala  Ala  Tyr  Gln  Leu  Gln  Ile  Glu  Ser
          35                       40                       45

Thr  Asn  Thr  Cys  Gly  Glu  Gln  Asn  Asp  Asn  His  Phe  Cys  Ile  Gln  Thr
     50                       55                       60

Met  Asn  Gln  Asn  His  Lys  Asn  Cys  Glu  Phe  Cys  Lys  Tyr  Asn  Asp  His
65                       70                       75                       80

Asn  Pro  Ser  Phe  Leu  Thr  Asp  Leu  His  Asp  Pro  Gln  Ser  Pro  Thr  Trp
                    85                       90                       95

Trp  Gln  Ser  Glu  Thr  Met  Phe  Glu  Gly  Ile  Gln  His  Pro  Asn  Tyr  Val
               100                      105                      110

Asn  Leu  Thr  Leu  His  Leu  Gly  Lys  Ser  Tyr  Asp  Ile  Thr  Tyr  Val  Arg
          115                      120                      125

Ile  Leu  Phe  Arg  Ser  Pro  Arg  Pro  Glu  Ser  Phe  Thr  Ile  Tyr  Lys  Arg
     130                      135                      140

Thr  Ser  Glu  Ser  Gly  Pro  Trp  Ile  Pro  Tyr  Gln  Phe  Tyr  Ser  Ala  Thr
145                      150                      155                      160
```

```
Cys Arg Asp Thr Tyr Ser Leu Pro Asp Ser Arg Ala Ile Arg Lys Gly
                165                 170                 175

Glu Gly Glu Ala His Ala Leu Cys Thr Ser Glu Tyr Ser Asp Ile Ser
            180                 185                 190

Pro Leu Arg Asp Gly Glu Ile Ala Phe Ser Thr Leu Glu Gly Arg Pro
        195                 200                 205

Ser Gly Ile Asn Phe Glu Arg Ser Gly Glu Leu Gln Glu Trp Val Thr
    210                 215                 220

Ala Thr Asp Ile Arg Ile Thr Leu Asp Arg Leu Asn Thr Phe Gly Asp
225                 230                 235                 240

Glu Leu Phe Gly Asp Ser Gln Val Leu Lys Ser Tyr Phe Tyr Ala Ile
            245                 250                 255

Ser Asp Ile Ala Val Gly Ala Arg
            260
```

( 2 ) INFORMATION FOR SEQ ID NO:40:

( i ) SEQUENCE CHARACTERISTICS:
        ( A ) LENGTH: 529 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Tyr Cys Val Val Ser Glu Arg Gly Glu Arg Val Arg Ser Cys His
1               5                   10                  15

Leu Cys Asn Ser Ser Asp Pro Lys Lys Ala His Pro Pro Ala Phe Leu
            20                  25                  30

Thr Asp Leu Asn Asn Pro His Asn Leu Thr Cys Trp Gln Ser Glu Asn
        35                  40                  45

Tyr Leu Gln Phe Pro His Asn Val Thr Leu Thr Leu Ser Leu Gly Lys
    50                  55                  60

Lys Phe Glu Val Thr Tyr Val Ser Leu Gln Phe Cys Ser Pro Arg Pro
65                  70                  75                  80

Glu Ser Met Ala Ile Tyr Lys Ser Met Asp Tyr Gly Arg Thr Trp Val
            85                  90                  95

Pro Phe Gln Phe Tyr Ser Thr Gln Cys Arg Lys Met Tyr Asn Arg Pro
        100                 105                 110

His Arg Ala Pro Ile Thr Lys Gln Asn Glu Gln Glu Ala Val Cys Thr
        115                 120                 125

Asp Ser His Thr Asp Met Arg Pro Leu Ser Gly Gly Leu Ile Ala Phe
    130                 135                 140

Ser Thr Leu Asp Gly Arg Pro Ser Ala His Asp Phe Asp Asn Ser Pro
145                 150                 155                 160

Val Leu Gln Asp Trp Val Thr Ala Thr Asp Ile Arg Val Ala Phe Ser
            165                 170                 175

Arg Leu His Thr Phe Gly Asp Glu Asn Glu Asp Asp Ser Glu Leu Ala
            180                 185                 190

Arg Asp Ser Tyr Tyr Tyr Ala Val Ser Asp Leu Gln Val Gly Gly Arg
        195                 200                 205

Cys Lys Cys Asn Gly His Ala Ala Arg Cys Val Arg Asp Arg Asp Asp
    210                 215                 220

Ser Leu Val Cys Asp Cys Lys His Asn Thr Ala Gly Pro Glu Cys Asp
225                 230                 235                 240
```

| | | | | | | | | | | | | | | |
|---|---|---|---|---|---|---|---|---|---|---|---|---|---|---|
| Arg | Cys | Lys | Pro | Phe<br>245 | His | Tyr | Asp | Arg | Pro<br>250 | Trp | Gln | Arg | Ala | Thr<br>255 | Ala |
| Arg | Glu | Ala | Asn<br>260 | Glu | Cys | Val | Ala | Cys<br>265 | Asn | Cys | Asn | Leu | His<br>270 | Ala | Arg |
| Arg | Cys | Arg<br>275 | Phe | Asn | Met | Glu | Leu<br>280 | Tyr | Lys | Leu | Ser | Gly<br>285 | Arg | Lys | Ser |
| Gly | Gly<br>290 | Val | Cys | Leu | Asn | Cys<br>295 | Xaa | Xaa | Asn | Thr | Xaa<br>300 | Xaa | Arg | His | Cys |
| His<br>305 | Tyr | Xaa | Xaa | Gly | Gly<br>310 | Xaa | Leu | Leu | Pro | Arg<br>315 | His | Gly | Lys | Pro | Ile<br>320 |
| Thr | His | Arg | Lys | Ala<br>325 | Cys | Lys | Ala | Cys | Asp<br>330 | Cys | His | Pro | Val | Gly<br>335 | Ala |
| Ala | Gly | Lys | Thr<br>340 | Cys | Asn | Gln | Thr | Thr<br>345 | Gly | Gln | Cys | Pro | Cys<br>350 | Lys | Asp |
| Gly | Val | Thr<br>355 | Gly | Ile | Thr | Cys | Asn<br>360 | Arg | Cys | Ala | Lys | Gly<br>365 | Tyr | Gln | Gln |
| Ser | Arg<br>370 | Ser | Pro | Ile | Ala | Pro<br>375 | Cys | Ile | Lys | Ile | Pro<br>380 | Val | Arg | Arg | Pro |
| Thr<br>385 | Ala | Ala | Ser | Xaa | Val<br>390 | Glu | Glu | Xaa | Xaa | Glu<br>395 | Asp | Cys | Asp | Ser | Tyr<br>400 |
| Cys | Lys | Ala | Ser | Lys<br>405 | Gly | Lys | Leu | Lys | Met<br>410 | Asn | Met | Lys | Lys | Tyr<br>415 | Cys |
| Arg | Lys | Asp | Tyr<br>420 | Ala | Val | Gln | Ile | His<br>425 | Ile | Leu | Lys | Ala | Asp<br>430 | Lys | Ala |
| Gly | Asp | Trp<br>435 | Trp | Lys | Phe | Thr | Val<br>440 | Asn | Ile | Ile | Ser | Val<br>445 | Tyr | Lys | Gln |
| Gly | Thr | Ser<br>450 | Arg | Ile | Arg | Arg<br>455 | Gly | Asp | Gln | Ser | Leu<br>460 | Trp | Ile | Arg | Ser |
| Arg | Asp<br>465 | Ile | Ala | Cys | Lys<br>470 | Cys | Pro | Lys | Ile | Lys<br>475 | Pro | Leu | Lys | Lys | Tyr<br>480 |
| Leu | Leu | Leu | Gly | Asn<br>485 | Ala | Xaa | Asp | Ser | Pro<br>490 | Asp | Gln | Ser | Gly | Ile<br>495 | Val |
| Ala | Asp | Lys | Ser<br>500 | Ser | Leu | Val | Ile | Gln<br>505 | Trp | Arg | Asp | Thr | Trp<br>510 | Ala | Arg |
| Arg | Leu | Arg<br>515 | Lys | Phe | Gln | Gln | Arg<br>520 | Glu | Lys | Lys | Gly | Lys<br>525 | Cys | Lys | Lys |
| Ala | | | | | | | | | | | | | | | |

( 2 ) INFORMATION FOR SEQ ID NO:41:

( i ) SEQUENCE CHARACTERISTICS:
        ( A ) LENGTH: 2783 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

```
NTCCTGCGCC  TGCTGCTCAC  CACCAGCGTG  CTCCGCCTGG  CACGAGCTGC  AAACCCCTTC      60
GTGGCTCAGC  AGACTCCCCC  AGACCCCTGC  TACGATGAGA  GCGGGGCTCC  CCCGCGCTGC     120
ATCCCCGAGT  TCGTCAACGC  CGCCTTTGGG  AAGGAGGTGC  AGGCTTCCAG  CACCTGTGGG     180
AAGCCCCCAA  CACGGCACTG  CGATGCCTCG  GACCCCCGCC  GAGCCCACCC  ACCCGCCTAC     240
CTGACCGACC  TCAACACCGC  CGCCAACATG  ACGTGCTGGC  GCTCCGAGAC  CCTGCACCAC     300
CTGCCCCACA  ACGTCACCCT  CACCCTTTCC  CTCGGCAAGA  AGTTTGAGGT  GGTCTACGTC     360
```

| | | | | | |
|---|---|---|---|---|---|
| AGCCTCCAGT | TCTGCTCGCC | CCGGCCGGAG | TCCACCGCCA | TCTTCAAGTC | CATGGACTAC | 420 |
| GGCAAGACGT | GGGTCCCCTA | CCAGTACTAC | TCCTCGCAGT | GCCGCAAGAT | CTACGGCAAG | 480 |
| CCCAGCAAGG | CCACCGTCAC | CAAGCAGAAC | GAGCAGGAGG | CGCTGTGCAC | CGATGGCCTC | 540 |
| ACCGACCTCT | ACCCGCTCAC | TGGCGGCCTC | ATCGCCTTCA | GCACGCTCGA | CGGGCGGCCC | 600 |
| TCGGCCCAGG | ACTTCGACAG | CAGCCCTGTG | CTGCAGGACT | GGGTGACGGC | CACCGACATC | 660 |
| CGGGTGGTGT | TCAGCCGTCC | CCACCTCTTC | CGCGAGCTGG | GGGCCGCGA | GGCTGGCGAG | 720 |
| GAGGACGGGG | GGGCCGGGGC | CACCCCCTAC | TACTACTCGG | TGGGCGAGCT | GCAGGTCGGC | 780 |
| GGGCGCTGCA | AGTGCAACGG | GCACGCCTCG | CGCTGCGTCA | AGGACAAGGA | GCAGAAGCTG | 840 |
| GTGTGTGACT | GCAAGCACAA | CACCGAGGGG | CCCGAGTGCG | ACCGCTGCAA | GCCCTTCCAC | 900 |
| TACGACCGGC | CGTGGCAGCG | GGCCAGCGCC | CGCGAGGCCA | ACGAGTGCCT | GGCCTGCAAC | 960 |
| TGCAACCTGC | ACGCTCGGCG | CTGCCGCTTC | AACATGGAGC | TGTATAAGCT | GTCCGGCAGG | 1020 |
| AAGAGCGGCG | GCGTTTGCCT | CAACTGCCGA | CACAACACGG | CTGGGAGGCA | CTGCCACTAC | 1080 |
| TGCAAGGAGG | GCTTCTACCG | GGACCTCAGC | AAGTCCATCA | CGGACCGCAA | GGCCTGCAAA | 1140 |
| GCCTGTGACT | GCCACCCAGT | TGGTGCTGCT | GGCAAGACCT | GCAACCAAAC | AACAGGGCAG | 1200 |
| TGCCCGTGCA | AGGACGGCGT | GACCGGCCTC | ACCTGCAACC | GCTGCGCCAA | GGGCTTCCAG | 1260 |
| CAGAGCCGCT | CGCCTGTGGC | CCCCTGCATC | AAGATCCCTG | CCATCAACCC | GACCTCTCTT | 1320 |
| GTCACCAGCA | CGGAGGCACC | TGCAGACTGT | GACTCCTACT | GCAAGCCAGC | CAAAGGCAAC | 1380 |
| TACAAGATTA | ACATGAAGAA | GTACTGCAAG | AAGGATTACG | TGGTCCAAGT | GAACATTTTG | 1440 |
| GAAATGGAGA | CGGTGGCCAA | CTGGGCCAAG | TTCACCATCA | ACATCCTCTC | TGTCTACAAG | 1500 |
| TGCCGCGACG | AGCGGGTCAA | GCGCGGAGAC | AACTTCTTGT | GGATCCACCT | CAAGGACCTG | 1560 |
| TCCTGCAAGT | GCCCCAAAAT | CCAGATCAGC | AAGAAGTACC | TGGTGATGGG | CATCAGCGAG | 1620 |
| AACTCCACCG | ACCGGCCGGG | ACTGATGGCC | GACAAGAACA | GCCTGGTCAT | CCAGTGGAGG | 1680 |
| GACGCCTGGA | CTCGCCGCCT | TCGGAAACTG | CAGCGGAGGG | AGAAGAAAGG | GAAGTGTGTG | 1740 |
| AAGCCCTGAG | GGCCTCGTGC | CCCACGCGGG | TCCCGGCCCC | ACTGCACACG | CAGACCATGC | 1800 |
| CCAGAGACTC | TGTACATACA | TATCGTGTGA | ACGGACTCTT | CTGTCTATAG | TGTATATTTT | 1860 |
| GGCAACGGTT | CCCCTTTTTG | TGTGCGTGTG | CACGCGTGGG | TGTGTGCACG | TGTGTGTGCG | 1920 |
| TGTGTGTGT | TGTGTGTGTG | TGTGTCTCCT | CTCAGTGTGT | ATTAAAAATA | AGGCGGTAAT | 1980 |
| GACAAACCTT | TAATGAGGAG | CAAAGCAGAG | GGGGTCCTGT | GGGTGCCTGC | TGCCTGAAGG | 2040 |
| AGCTTGAGGG | GCTGGTTTCT | TGCTCCGGGC | GTGCTGTTCC | TCACCCTTCT | GTCCTACTCT | 2100 |
| CTCTTTCCCC | TTGAGCAAAA | CCTTCTGCCC | AGTGCTGCTG | TCTGAGCTCG | CGGCTCTCCC | 2160 |
| TGCTGCAGAG | CCCGGTCCCT | CTCACGTGCT | GCACATGTGC | TGCTCTCAGC | TCTCTGTGCC | 2220 |
| CCTTTTCTTG | TGCAGCAGAG | ACGGGAGGTC | GGTTCCTCC | ATCCCGCTGC | ACACGGAC | 2280 |
| CGGCTGGGTG | GAGACCATCC | AGCGCTGCAG | GACCGGCCCC | AGGAGCTCCG | CTGGGAGAAC | 2340 |
| CAAGTGACCT | TTCTCCAGGC | CTGATCCTGC | AGGACCTCAG | CTTTACATGG | ACTGGTCGTG | 2400 |
| CCGCCCAGGG | GCAGGGCCCA | TGGAAGTCTT | GGGGACAGCC | AGGGCTGTTG | GCCACCACCC | 2460 |
| CACAGAGCTG | TTCTGAGCAG | GGCGCAGGGG | TCTGCCTGTC | CTGGTGCGTG | GTCCAGGTGA | 2520 |
| CCCAWCAGGA | AAGACCTGCA | GATACCCATA | TTCTCCTCTC | GTGCCAGCTC | TGCATGCTGC | 2580 |
| TGTGACCTTG | GCCGTGCCAG | AGGTGCAGAG | GCAGAGGTGG | CAGGAAGAGA | GGAGAGCTTT | 2640 |
| CGCTGACCAA | CCTCCAGTCT | TTCATTTCTT | CTKCATACTG | TATTAGTCTC | CAGTTCAAAC | 2700 |
| AGACATCAGT | TTCTTTCCAC | GTTGAGGTTA | TAGTGGTCTC | GAYGTAATAA | ACATGAATGG | 2760 |

AAATAATAAA AAAAAAAAA AAA                                                                        2783

(2) INFORMATION FOR SEQ ID NO:42:

( i ) SEQUENCE CHARACTERISTICS:
        ( A ) LENGTH: 2166 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

```
TGTATGTTGT  GTGRRTTGTG  ANNNNATAAC  AATTTCACAC  AGGAAACAGC  NNNNNNNNNN     60
NNNNNNGCTA  CTGCGTGGTG  AGCGAGCGTG  GTGAAGAGCG  CGTGCGCTCC  TGTCACCTCT    120
GCAACTCTTC  GGATCCCAAG  AAAGCGCACC  CGCCCGCCTT  CCTCACCGAC  CTCAATAACC    180
CGCACAACCT  GACGTGCTGG  CAGTCCGAGA  ACTACCTGCA  GTTCCCGCAC  AACGTGACGC    240
TCACTCTGTC  GCTCGGCAAG  AAGTTTGAGG  TGACCTATGT  GAGCCTGCAA  TTCTGCTCGC    300
CGCGGCCAGA  GTCCATGGCC  ATCTACAAGT  CCATGGACTA  CGGGCGCACG  TGGGTGCCCT    360
TCCAGTTCTA  TTCCACGCAG  TGCCGCAAAA  TGTACAACCG  GCCGCACCGC  GCGCCTATCA    420
CCAAACAGAA  CGAGCAGGAG  GCCGTGTGCA  CCGACTCGCA  CACCGACATG  CGCCCGCTCT    480
CTGGCGGGCT  GATCGCTTTC  AGCACGCTGG  ACGGGCGGCC  CTCGGCGCAC  GACTTCGACA    540
ACTCGCCGGT  GCTGCAGGAC  TGGGTCACGG  CCACCGACAT  CCGCGTGGCT  TTCAGCCGCC    600
TGCACACGTT  CGGCGACGAG  AACGAAGACG  ACTCGGAGCT  GGCGCGCGAC  TCCTATTACT    660
ATGCAGTGTC  TGACCTGCAG  GTTGGCGGCC  GCTGCAAGTG  CAACGGCCAC  GCGGCGCGTT    720
GCGTGCGCGA  CCGAGACGAC  AGTCTGGTGT  GTGACTGTAG  CACAACACG   GCCGGCCCTG    780
AATGCGACCG  TTGCAAGCCC  TTCCACTACG  ACCGGCCCTG  GCAGCGCGCC  ACGGCCCGCG    840
AGGCCAACGA  GTGCGTGGCC  TGCAACTGCA  ACCTCCATGC  TCGGCGCTGC  AGATTCAACA    900
TGGAGCTCTA  TAAGCTATCA  GGGCGCAAGA  GCGGGGGAGT  STGTCTCAAC  TGCCNNNACA    960
ACACTCNNNG  CCGCCACTGC  CACTACTGNN  AAGGAGGGNN  NCTTCTACCG  AGACATGGGC   1020
AAGCCTATCA  CCCACCGGAA  GGCTTGCAAA  GCCTGTGATT  GCCACCCAGT  GGGTGCTGCT   1080
GGCAAGACCT  GCAATCAAAC  CACTGGCCAA  TGTCCCTGCA  AGGACGGCGT  GACGGGCATC   1140
ACCTGCAACC  GATGTGCCAA  AGGCTACCAG  CAGAGCCGTT  CCCCATCGC   CCCTTGCATC   1200
AAGATTCCTG  TGGCGCCGCC  CACCACTGCA  GCCAGCAGCN  GTGGAGGAAC  NNNNGGAAGA   1260
CTGTGATTCC  TATTGCAAGG  CCTCCAAAGG  CAAGCTGAAG  ATGAACATGA  AGAAATACTG   1320
CAGGAAGGAC  TATGCTGTCC  AGATCCACAT  CCTGAAGGCC  GACAAAGCAG  GGACTGGTG    1380
GAAGTTCACC  GTGAACATCA  TCTCCGTGTA  CAAGCAGGGC  ACAAGTCGTA  TTCGCCGTGG   1440
TGACCAGAGT  TTGTGGATCC  GCTCACGAGA  CATCGCCTGY  AAGTGTCCCA  AAATCAAGCC   1500
CCTCAAGAAG  TACTTGCTGT  TGGGTAATGC  CNGAGGACTC  ACCTGACCAG  AGTGGCATCG   1560
TGGCAGACAA  GAGCAGCCTG  GTGATCCAGT  GGCGGGACAC  ATGGGCACGG  CGGCTGCGCA   1620
AGTTCCAGCA  ACGGGAGAAG  AAGGGCAAGT  GCAAGAAGGC  CTAGCGCGGA  GGTGGCGCGG   1680
GCTCCAGGAG  GGCGGGCAGG  GCGCTGGCAA  AGGCTGGCAG  CCTTGGACTT  GGCCGTCAGG   1740
GGNNTTTTTK  GGAGGGTGGG  NNNCGGGGCG  AAGTCGAAGT  GGCGGGGCCC  TCAGCCGTCC   1800
GCCCCAGCCC  CWCCCTCACA  CCCCTGGCTG  CGCTCTTATG  GCGCATGGGC  AGAAAGCNCC   1860
CTGTATTGAC  AGGCCAGGCC  CTGGANAAAT  GAGGACAAGA  CATAGCTACC  TCACGGCGCT   1920
```

-continued

| | | | | | |
|---|---|---|---|---|---|
| CCTTCCAGAA | CAGAGATGCG | CTTCCCTAGG | GCTAGGTGGG | GGTCGCNNGT | GGAGGGGTTA | 1980 |
| GGGAGGTCCT | GAGAGGCGGG | AACAGAATGG | CACAGTGGTC | TACAGTCGCT | GTGTTTGATG | 2040 |
| GTTATTGAAG | GGGGATGTAA | GAACTGTGAA | TTTTTGGGCC | TGCNNCCTGG | GCCAGGGGNA | 2100 |
| ACCAATCCAC | CACCAGACAC | TAGTCACGCC | CCCCTCCTTT | CTCCATCACC | CGCTGTCTAG | 2160 |
| GAATTC | | | | | | 2166 |

( 2 ) INFORMATION FOR SEQ ID NO:43:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

| | | | | | |
|---|---|---|---|---|---|
| ATGCCGCGGA | GGGGCGCGGA | GGGGCCGCTC | GCCCTGCTGC | TGGCGGCCGC | GTGGCTGGCA | 60 |
| CAGCCGCTGC | GAGGCGGCTA | CCCCNNNCTG | AACATGTTCG | CCGTGCAGAC | GNCAGCCGAC | 120 |
| CCCTGCTACG | ACGAGCACGG | GCTGCCCCNC | CGCTGCATCC | CGGACTTCGT | CAACTCGGCC | 180 |
| TTCGGCAAGG | AGGTGAAGGT | GTCGAGCACC | TGCGGGAAGC | CGCCGTCGAG | GTACTGCGTG | 240 |
| GTGACGGAGA | AGGGCGAGGA | GCAGGTCCGC | TCGTGCCACC | TCTGCAACGC | CTCCGACCCC | 300 |
| AAGCGCGCCC | ACCCGCCCTC | CTTCCTCACC | GACCTCAACA | ACCCGCACAA | CCTGACGTGC | 360 |
| TGGCAGTCCG | ACAGCTACGT | GCAGTACCCG | CACAACGTCA | CCCTCACGCT | GTCCCTCGGC | 420 |
| AAGAAGTTCG | AGGTGACCTA | CGTGAGCCTG | CAGTTCTGCT | CGCCGCGCCC | CGAGTCCATG | 480 |
| GCCATCTACA | AGTCCATGGA | CTACGGCAAG | ACGTGGGTGC | CCTTCCAGTT | CTACTCCACG | 540 |
| CAGTGCCGCA | AGATGTACAA | CAAGCCGAGC | CGCGCCGCCA | TCACCAAGCA | GAACGAGCAG | 600 |
| GAGGCCATCT | GCACCGACTC | GCACACCGAC | GTGCGGCCCC | TCTCCGGCGG | CCTCATCGCC | 660 |
| TTCAGCACCC | TGGACGGCCG | CCCCACCGCC | CACGACTTCG | ACAACTCGCC | CGTGCTGCAG | 720 |
| GACTGGGTGA | CGGCCACCGA | CATCAAGGTG | ACCTTCAGCC | GCCTGCACAC | CTTCGGCGAC | 780 |
| GAGAACGAGG | ACGACTCCGA | GCTCGCCCGC | GACTCCTACT | TCTACGCCGT | GTCCGACCTG | 840 |
| CAGGTCGGCG | GGCGCTGCAA | GTGCAACGGG | CACGCGTCCC | GCTGCGTCCG | CGACCGCGAC | 900 |
| GACAACCTGG | TGTGCGACTG | CAAGCACAAC | ACGGCCGGGC | CCGAGTGCGA | CCGCTGCAAA | 960 |
| CCCTTCCACT | ACGACCGGCC | CTGGCAGAGG | GCGACCGCCC | GAGAGGCCAA | CGAGTGCGTG | 1020 |
| GCCTGCAACT | GCAACCTGCA | TGCACGGCGC | TGCCGCTTCA | ACATGGAGCT | GTACAAGCTG | 1080 |
| TCGGGCAGAA | AGAGCGGCGG | TGTCTGCCTC | AACTGCCGGC | ACAACACGGC | CGGGCGGCAC | 1140 |
| TGCCACTACT | GCAAGGAAGG | CTTCTACCGC | GACCTCAGCA | AACCCATCTC | CCACCGCAAG | 1200 |
| GCCTGCAAAG | AGTGCGATTG | CCATCCCGTG | GGCGCCGCCG | CCAAACCTG | CAACCAAACC | 1260 |
| ACGGGGCAGT | GTCCATGCAA | GGACGGCGTC | ACCGGCATCA | CCTGCAACCG | CTGCGCCAAG | 1320 |
| GGCTACCAGC | AGAGCCGCTC | GCCCATTGCC | CCCTGCATAA | AGATCCCCGC | CGCGCCGCCC | 1380 |
| CCCACAGCTG | CCAGCAGCAC | GGAGGAGCCT | GCAGACTGTG | ACTCGTACTG | CAAAGCCTCC | 1440 |
| AAGGGGAAGC | TGAAGATCAA | CATGAAGAAG | TACTGCAAGA | AGGACTACGC | TGTGCAGATC | 1500 |
| CACATCCTGA | AAGCGGAAAA | AAATGCCGAC | TGGTGGAAGT | TCACCGTCAA | CATCATCTCT | 1560 |
| GTCTACAAAC | AGGGCAGCAA | CCGGCTGCGG | CGCGGGGACC | AGACCCTGTG | GGTGCACGCC | 1620 |
| AAGGACATCG | CCTGCAAGTG | CCCCAAGGTG | AAGCCCATGA | AGAAGTACCT | CCTGCTGGGC | 1680 |
| AGCACCGAGG | ACTCTCCCGA | CCAGAGCGGC | ATCATCGCGG | ACAAGAGCAG | CCTGGTGATC | 1740 |

| | | | | | |
|---|---|---|---|---|---|
| CAATGGCGGG | ACACGTGGGC | ACGGCGGCTG | CGGAAGTTCC | AGCAGAGGGA | GAAGAAGGGG | 1800 |
| AAGTGTAGGA | AGGCGTAGGG | AGGAGCGGTG | ATGGACTGAG | CGCTGCCGGG | TGCGGGCGGG | 1860 |
| GGGTGGGCGC | AGGGGGCTCA | CGGCATCTCG | TATTGAGGGA | TGGAAGGGGA | AAAAAAACAC | 1920 |
| GAAACC | | | | | | 1926 |

( 2 ) INFORMATION FOR SEQ ID NO:44:

( i ) SEQUENCE CHARACTERISTICS:
        ( A ) LENGTH: 1839 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

| | | | | | |
|---|---|---|---|---|---|
| ATGATCACAT | CAGTATTGCG | CTATGTGCTA | GCGCTCTACT | TTTGTATGGG | CATAGCTCAT | 60 |
| GGAGCATACT | TTTCACAGTT | CTCCATGAGA | GCCCCAGACC | ATGATCCTTG | CCATGATCAT | 120 |
| ACTGGTCGAC | CAGTTCGATG | TGTTCCCGAG | TTCATAAATG | CTGCTTTTGG | AAAACCTGTT | 180 |
| ATTGCTAGTG | ATACATGCGG | AACAAACCGA | CCAGACAAGT | ATTGTACTGT | GAAGGAGGGT | 240 |
| CCGGATGGAA | TTATCCGTGA | GCAATGTGAC | ACTTGTGATG | CTAGAAACCA | TTTCCAATCC | 300 |
| CATCCAGCCT | CTCTTCTAAC | TGATCTCAAT | TCGATTGGAA | ACATGACATG | CTGGGTTTCC | 360 |
| ACTCCAAGTT | TGAGCCCACA | AAACGTTTCA | CTCACTTTGT | CACTCGGAAA | AAAGTTTGAG | 420 |
| CTCACTTACG | TCTCAATGCA | CTTCTGTTCC | CGTCTCCCAG | ATTCAATGGC | ACTTTACAAG | 480 |
| TCTGCTGACT | TTGGAAAGAC | CTGGACCCCG | TTTCAATTCT | ACTCCTCCGA | ATGTCGTCGT | 540 |
| ATATTTGGCA | GAGATCCCGA | CGTGTCGATA | ACAAAGTCAA | ACGAGCAAGA | AGCCGTTTGT | 600 |
| ACTGCCTCTC | ATATAATGGG | TCCAGGAGGA | AACCGTGTAG | CGTTCCCTTT | CTAGAGAAC | 660 |
| AGACCTTCTG | CACAAAACTT | CGAAAACTCG | CCGGTGCTTC | AGGATTGGGT | CACCGCAACT | 720 |
| GACATTAAAG | TGGTGTTTTC | AAGGCTTAGT | CCAGATCAGG | CTGAACTGTA | TGGCTTGTCT | 780 |
| AACGATGTCA | ATTCGTACGG | AAACGAGACG | GATGATGAAG | TCAAACAACG | TTACTTCTAC | 840 |
| TCAATGGGAG | AACTGGCAGT | TGGTGGTCGC | TGCAAATGTA | ATGGTCACGC | CAGTAGATGC | 900 |
| ATCTTTGACA | AAATGGGCCG | GTACACTTGT | GACTGCAAGC | ATAACACTGC | CGGAACTGAA | 960 |
| TGCGAAATGT | GCAAACCATT | CCATTACGAT | CGTCCATGGG | AAGAGCCAC | CGCAAATTCT | 1020 |
| GCCAACTCAT | GTGTCGCTTG | CAACTGCAAC | CAACACGCAA | AGAGATGCCG | ATCGATGCT | 1080 |
| GAGCTCTTTA | GACTAAGTGG | CAACCGGTCA | GGAGGAGTGT | GCTTGAACTG | TCGTCATAAC | 1140 |
| ACTGCTGGAA | GAAATTGTCA | TCTCTGCAAA | CCAGGATTTG | TCCGTGATAC | TTCTCTGCCA | 1200 |
| ATGACACATC | GGAAAGCTTG | TAAAGCTTGT | GGATGTCATC | CAGTCGGATC | ACTTGGAAAA | 1260 |
| AGCTGCAACC | AATCATCGGG | TCAGTGCGTC | TGCAAGCCTG | GAGTCACTGG | AACAACCTGT | 1320 |
| AATCGTTGTG | CCAAAGGATA | CCAACAAAGC | CGTTCTACAG | TTACTCCGTG | TATCGAAATT | 1380 |
| CCGACCAAAG | CTGATTTCAT | TGGATCATCA | CATTCAGAAG | AGCAAGATCA | GTGTTCGAAG | 1440 |
| TGCAGAATTG | TTCCGAAGAG | ACTCAACCAG | AAGAAGTTCT | GCAAGCGGGA | TCATGCTGTC | 1500 |
| CAGATGGTTG | TGGTCAGCCG | TGAGATGGTT | GATGGATGGG | CCAAGTACAA | GATTGTGGTT | 1560 |
| GAATCAGTTT | TCAAACGAGG | CACCGAGAAC | ATGCAACGTG | GCGAAACATC | ATTGTGGATT | 1620 |
| TCCCCTCAAG | GTGTCATTTG | CAAGTGCCCA | AGCTCCGCG | TCGGACGCCG | TTATCTCCTC | 1680 |
| CTTGGTAAGA | ATGATTCCGA | TCACGAGCGC | GATGGATTGA | TGGTCAATCC | ACAGACTGTA | 1740 |

```
TTGGTGGAAT GGGAGGACGA TATTATGGAT AAGGTACTAC GCTTCTCGAA AAAAGATAAA      1800

CTTGGACAAT GCCCAGAGAT TACGTCACAC AGATACTGA                            1839
```

( 2 ) INFORMATION FOR SEQ ID NO:45:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

```
Met Glu Leu Tyr Lys Leu Ser Gly Arg Lys Ser Gly Gly Val Xaa Leu
 1               5                  10                    15

Asn Xaa Arg His
            20
```

( 2 ) INFORMATION FOR SEQ ID NO:46:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Met Glu Leu Tyr Lys Leu Ser Gly Gln Lys Ser Gly Gly Val
 1               5                  10
```

NUCLEIC ACIDS ENCODING NEURAL AXON OUTGROWTH MODULATORS

The research carried out in the subject application was supported in part by grants from the National Institutes of Health. The government may have rights in any patent issuing on this application.

INTRODUCTION

1. Technical Field

The technical field of this invention concerns proteins involved in neural axon outgrowth.

2. Background

In the developing nervous system, axons project considerable distances along stereotyped pathways to reach their targets. Axon growth and guidance depends partly on the recognition of cell-surface and extracellular matrix cues along these pathways.

The identification of such nerve cell growth and guidance cues is the holy grail of neurobiology. These are the compounds that tell neurons when to grow, where to grow, and when to stop growing. The medical applications of such compounds are enormous and include modulating neuronal growth regenerative capacity, treating neurodegenerative disease, and mapping (e.g. diagnosing) genetic neurological defects.

Over decades of concentrated research, various hypotheses involving chemo-attractants and repellents, labeled pathways, cell adhesion molecules, etc. have been invoked to explain guidance. Molecules such as N-CAM and N-cadherin have been reported to provide favorable substrates for axon growth and certain sensory axons may be responsive to NGF and NGF-like factors. Recent reports suggest the existence of diffusible chemotropic molecule(s) which influence the pattern and orientation of commissural axon growth.

Relevant Literature

Placzek et al. (1990) Development 110, 19–30; Placzek et al. (1990) Cold Spring Harbor Symposia on Quantitative Biology 55, 279–302.; and Tessier-Lavigne et al. (1988) Nature 336: 775–778 report evidence for diffusible chemotropic molecules which influence the pattern and orientation of commissural axon growth.

Gundersen and Barret (1980) JCB 87, 546–554, Lohof et al. (1992) J. Neurosci. 12 (4), 1253–1261 and Zheng et al. (1993) Soc. Neurosci. Abstr 19, 608.9 report neural chemotaxis in response to NGF, cAMP and acetylcholine, respectively.

Ishii et at. (1992) Neuron 9, 873–881 disclose a gene, unc-6, derived from C. elegans, which has sequence similarity to the some of the nucleic acids disclosed herein.

For a recent review of axon guidance, see Goodman and Shatz (1993) Cell Neuron 10, 77–98.

SUMMARY OF THE INVENTION

Methods and compositions relating to novel classes of neural axon outgrowth promoting and orienting proteins, nucleic acids encoding such proteins and receptors which selectively bind such proteins are disclosed. The disclosed neural axon outgrowth promoting and orienting proteins include the p75/p78 family; the first known family of vertebrate proteins which can promote spinal axon outgrowth in three-dimensions, and p75/p78 family-specific receptors, including receptors found on spinal axons, especially growth cones.

Also disclosed are agents including peptides derived from the disclosed neural axon outgrowth promoting proteins capable of effecting axon outgrowth, orientation and regeneration. These agents provide small molecular weight modulators of nerve cell growth useful in the treatment of neurological disease and injury.

The disclosed compositions also find use variously in screening chemical libraries for regulators of axon outgrowth and orientation, in genetic mapping, as probes for related genes, as diagnostic reagents for genetic neurological disease and in the production of specific cellular and animal systems for the development of neurological disease therapy.

BRIEF DESCRIPTION OF THE FIGURES

FIG. 4: Expression of p78 (top) and p75 bottom) transcripts in the early developing chick embryo (E2.5), as assessed by non-radioactive in situ hybridization using digoxygenin-labeled anti-sense cRNA probes. Top. Within the spinal cord, p78 is selectively expressed in the floor plate (dark triangle at ventral midline of the spinal cord). Outside of the spinal cord, p78 is expressed in two symmetrically located bands of cells which constitute the left and right dermomyotomes of the embryo. Bottom. p75 is expressed in a ventral to dorsal gradient within the spinal cord (at lower levels than p78), and also in the dermomyotomes. Additional staining seen here is probably background.

FIG. 5: Deduced amino acid sequence of chick p78 (SEQ ID NO:26), starting at the initiation methionine. The mature amino-terminus starts at residue 26 (GYP . . . ).

FIG. 6: Deduced amino acid sequence of chick p75 (SEQ ID NO:27), starting inside the signal sequence (the sequence is thought to lack several amino acids from the N-terminus, within the signal sequence). The mature amino terminus starts at residue 16 (ANP . . . ).

FIG. 7a–c: Comparison of the amino acid sequences of p78 (SEQ ID NO:26) and p75 (SEQ ID NO:27), showing the stretches of sequence identity between the proteins.

Figure 10A:
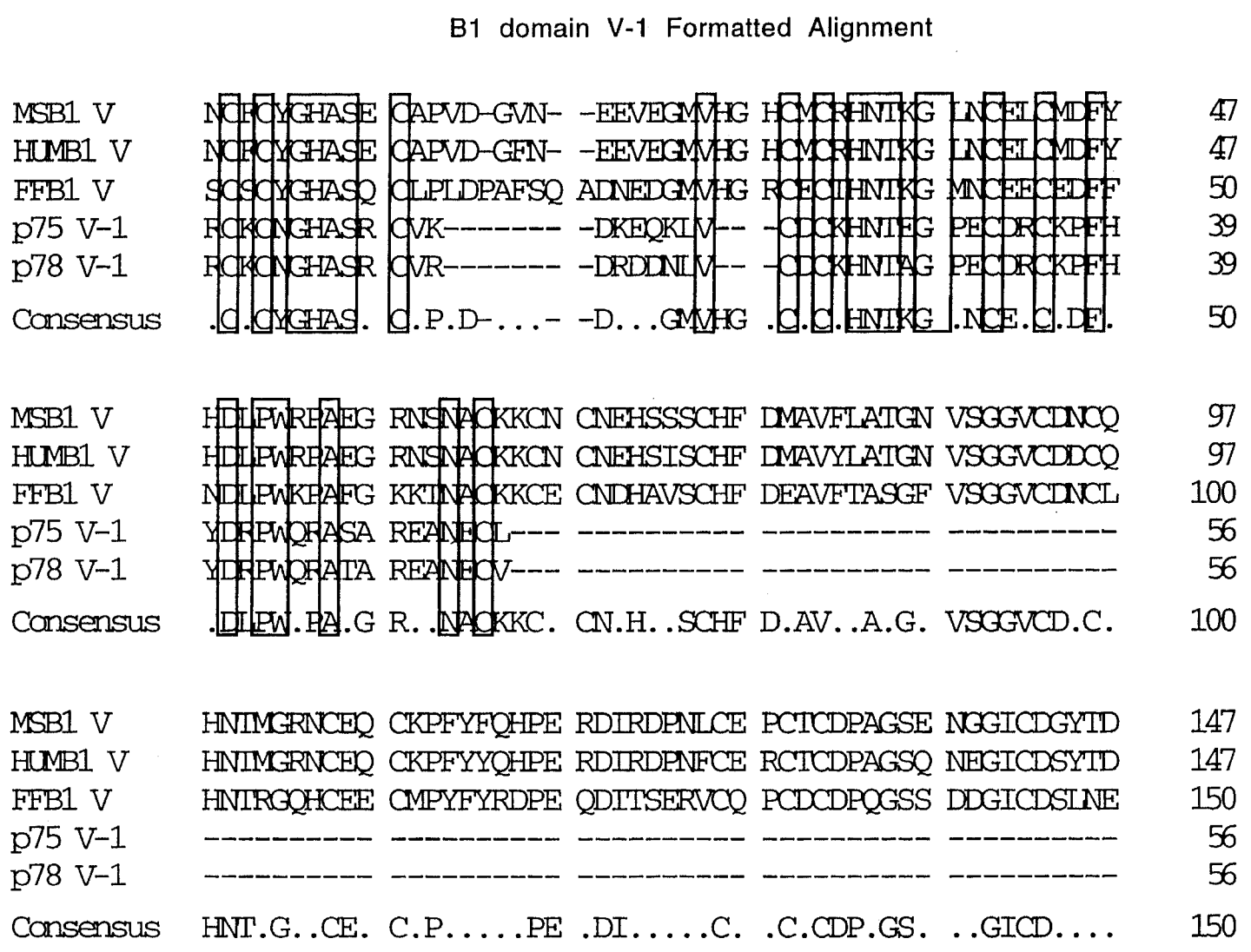

FIGS. 10a–b, 11a–b, and 12a–b: Alignment of each of the three EGF-like repeats within domain V of p78 (SEQ ID NO:26, residues 285–340, 341–403, and 404–453, respectively) and p75 (SEQ ID NO:27, residues 261–316, 317–379, and 404–453, respectively) to those present in domain V of laminin B1 from mouse (MSB1 (SEQ ID NO:28)), human (HUMB1 (SEQ ID NO:29)), and Drosophila (FFB1 (SEQ ID NO:30)). Laminin B1 contains EGF-like repeats, and each of the three repeats within p78 and p75 are most homologous to sequential repeats within the laminin domain V (repeats 1, 2, and 4).

FIGS. 13a–b, 14a–b, and 15a–b: Alignment of each of the three EGF-like repeats within domain V of p78 (SEQ ID NO:26, residues 285–340, 341–403, and 404–453, respectively) and p75 (SEQ ID NO:27, residues 261–316, 317–379, and 380–439, respectively) to those present in domain V of laminin B2 from mouse (MSB2 (SEQ ID NO:32)), human (HUMB2 (SEQ ID NO:31)), and Drosophila (FFB2 (SEQ ID NO:33)). Laminin B2 also contains EGF-like repeats, and each of the three repeats within p78 and p75 are most homologous to sequential repeats (and parts of repeats) within the laminin domain V (repeats 1, 2, and part of 3 with part of 4).

FIGS. 16a–b and 17a–b: Alignment of domain VI of p75 (SEQ. ID NO:27, residues 16–266) and p78 (SEQ ID NO:26, residues 26–284) with domain VI of laminin B1 (SEQ ID NOS: 34–36) (FIG. 16) and laminin B2 (SEQ ID NOS: 37–39) (FIG. 17). While this region in p75 (SEQ ID NO:27, residues 16–26) and p78 (SEQ ID NOS: 26, residues 26–284) is more homologous to that of laminin B2 (27% identity with B 2 vs. 15% identity with B1), there are significant homologies to laminin B1 sequences not present in laminin B2, suggesting that domain VI of p75 and p78 is more closely related to an ancestral laminin B chain rather than to either of the two chains separately.

FIG. 18a–c: Alignment of chick p78 (SEQ ID NO:26) with mouse p78 (SEQ ID NO:40). The two sequences are 86% identical in the regions currently available for both.

Figure 19D:
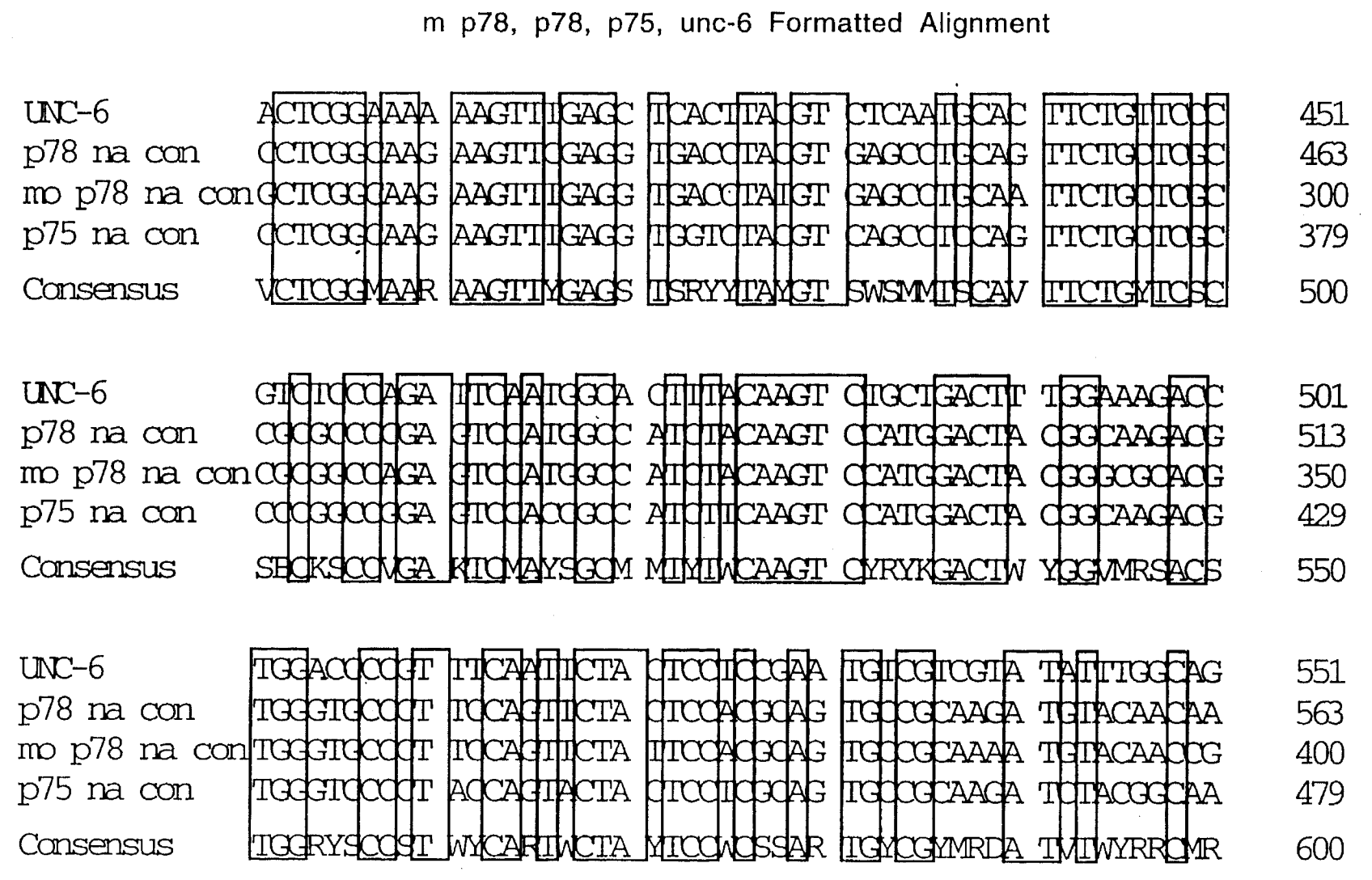
Figure 19E:
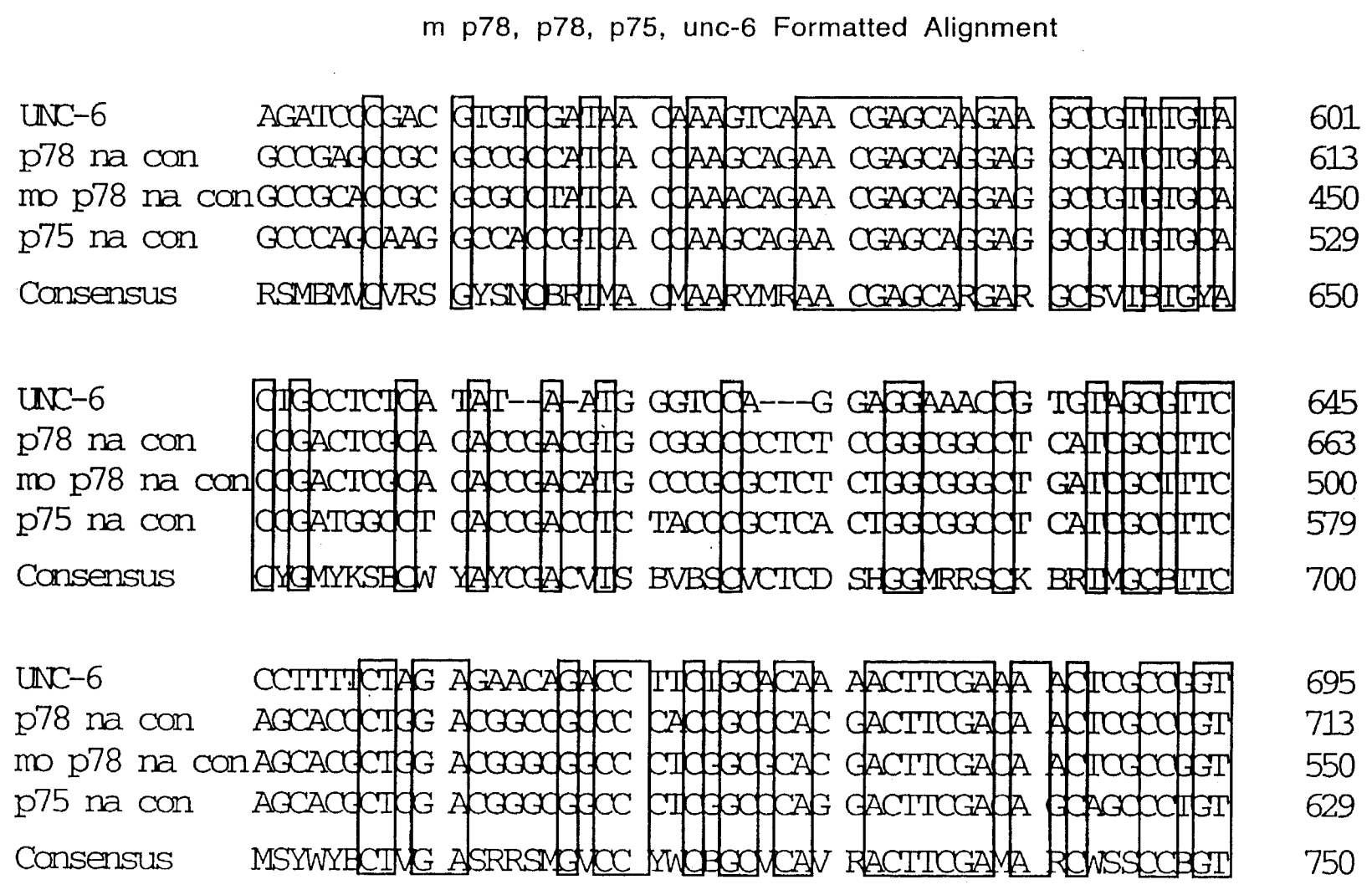
Figure 19G:
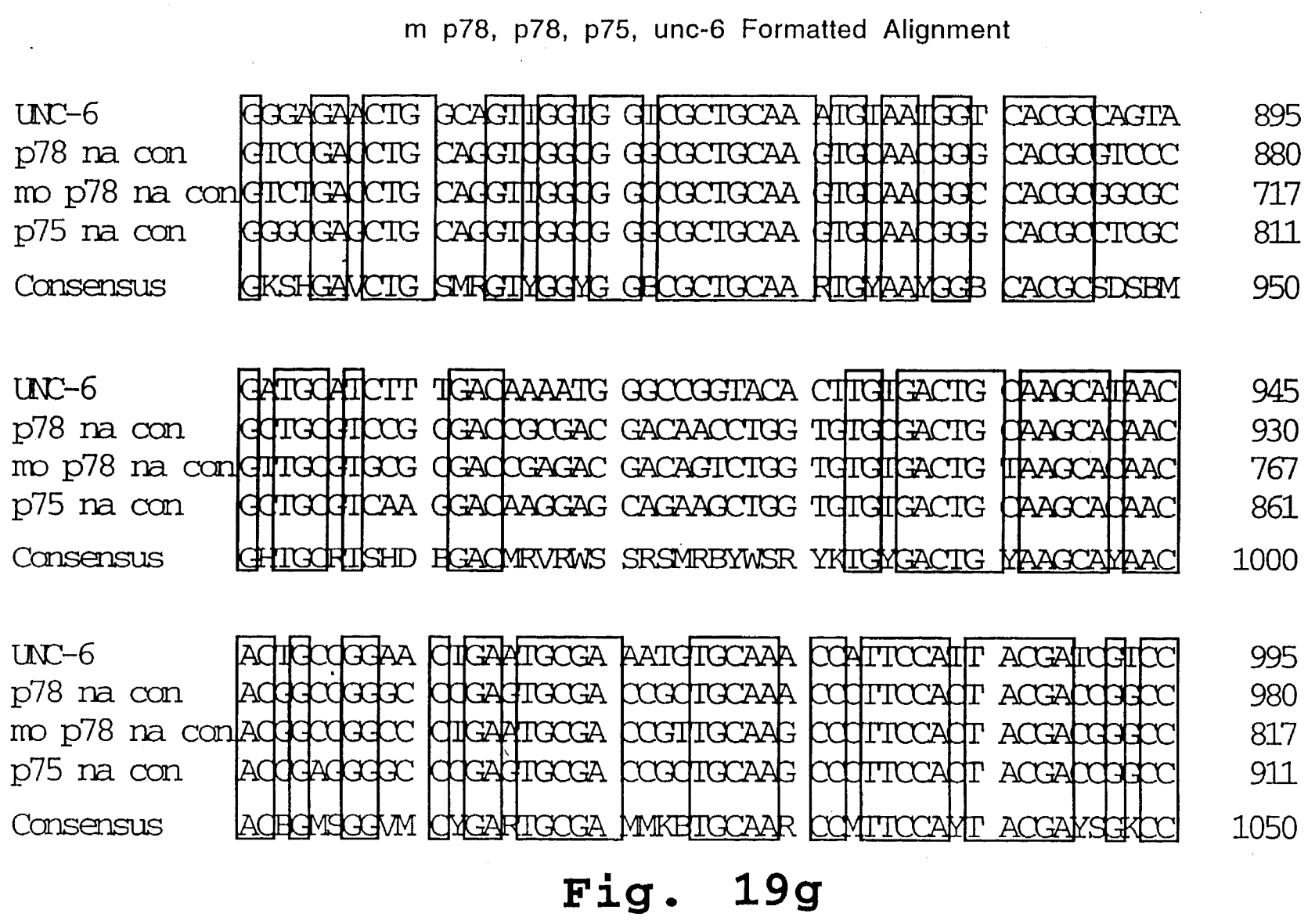
Figure 19K:
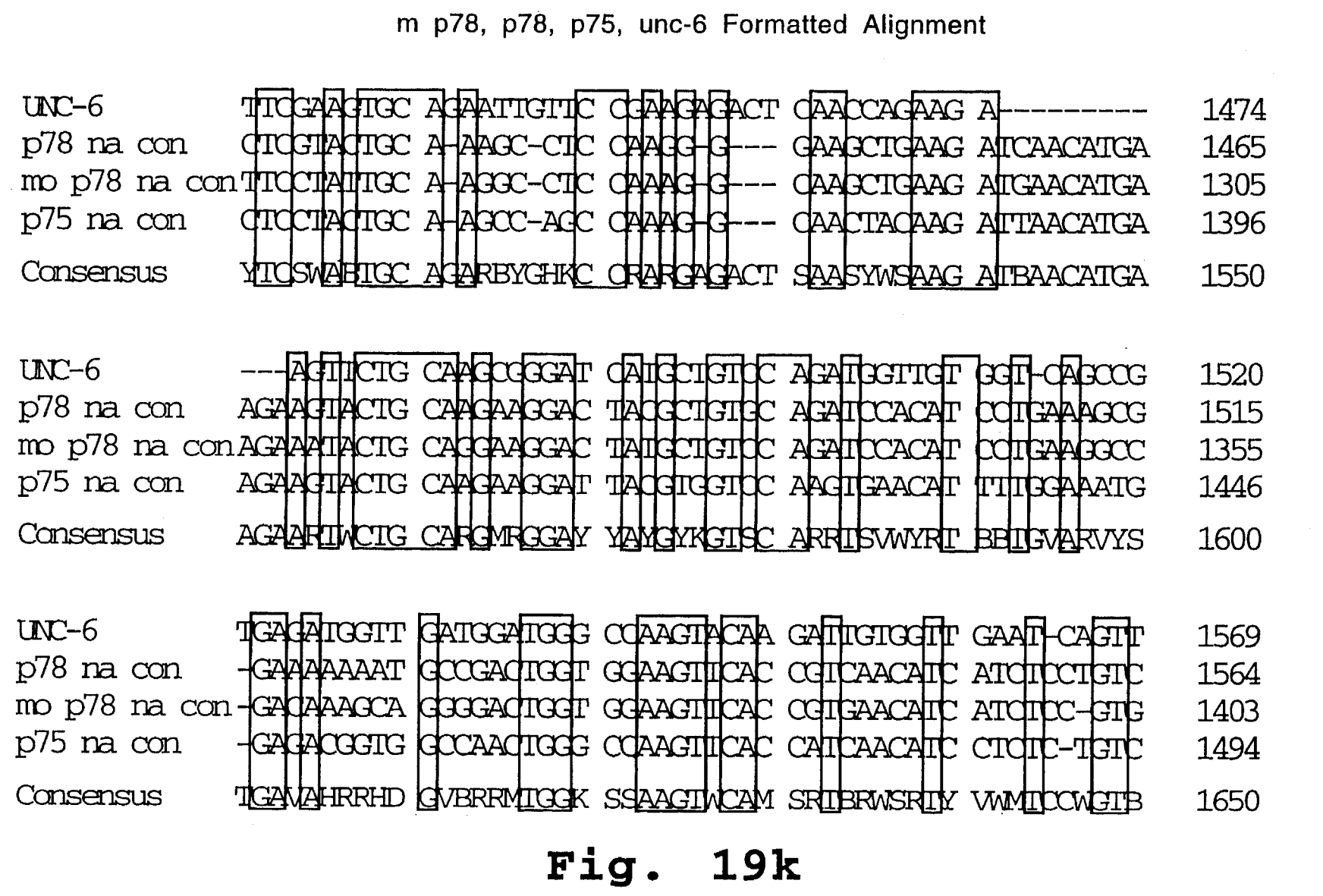
Figure 19M:
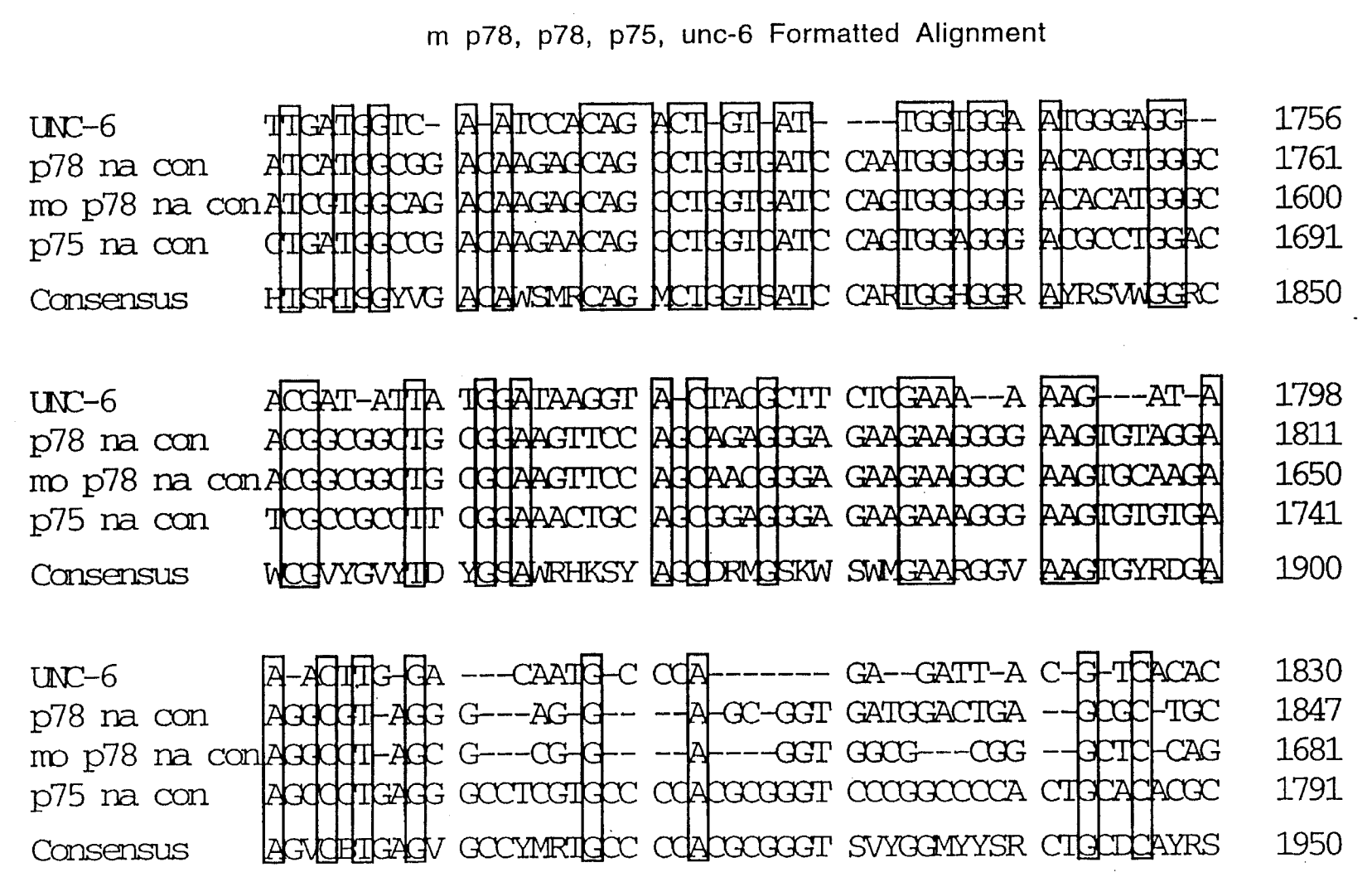

FIG. 19a–t: Aligned cDNAs of chick p75 (SEQ ID NO:41) and p78 (SEQ ID NO:43), mouse p78 (SEQ ID NO:42) and unc-6 (SEQ ID NO:44).

DESCRIPTION OF SPECIFIC EMBODIMENTS

Figure 1:
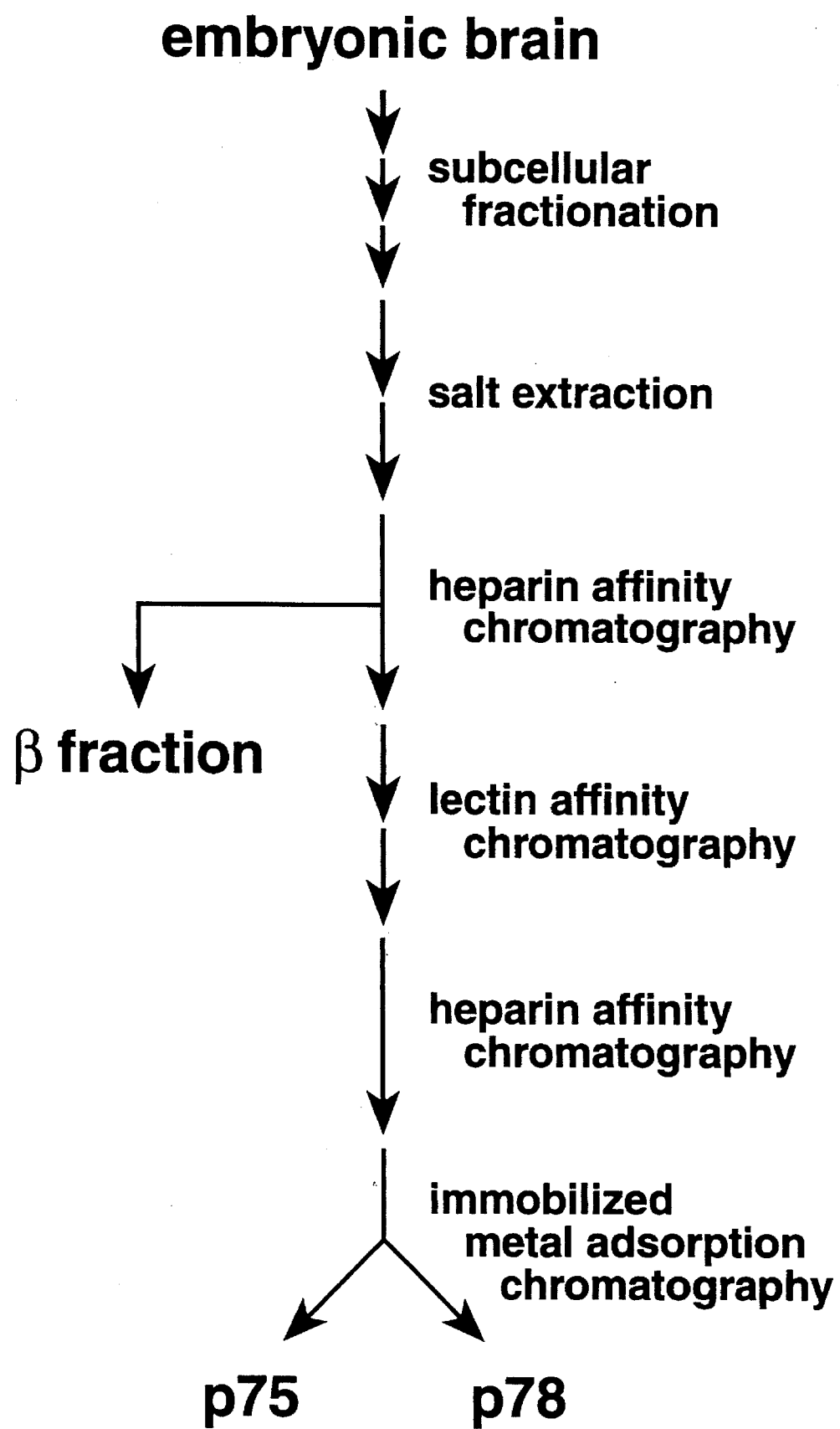
FIG. 1: Purification scheme. Refer to the Examples section for details of the steps involved.

The present invention discloses methods and compositions relating to modulators of nerve cell growth and function. The compositions include novel neural axon outgrowth promoting and/or orienting proteins, henceforth OPPs (now called "netrins") and their receptors. These compositions are shown to be capable of selectively promoting neural axon outgrowth and/or orientation. Preferred axon targets are spinal axons—axons residing at least partly in the spinal chords of vertebrates—of interneurons. Furthermore, the many of the compositions of the invention are shown to promote outgrowth in three dimensions in a semi-solid matrix such as a collagen gel or a physiological tissue, as opposed to merely providing a favorable substrate surface. Finally, many of the subject compositions are active as soluble factors.

OPPs include a novel class of proteins exemplified by p75 (netrin-2) and p78 (netrin-1). The invention provides agents, including OPP peptides, which specifically bind and act as agonists for OPP receptors. These agents find a wide variety of clinical, therapeutic and research uses where nerve cell growth is indicated, e.g. traumatic injury to nerve cells, neurodegenerative disease, etc. A wide variety of OPP and OPP receptor-specific binding agents and methods for identifying, making and using the same are described below.

The peptides of the invention comprise unique portions of the disclosed OPPs and OPP receptors (OPPs/receptors). A "unique portion" has an amino acid sequence unique to that disclosed in that it is not found in any previously known protein and has a length at least long enough to define a novel peptide. Unique portions are found to vary from about 5 to about 25 residues, preferably from 5 to 10 residues in length, depending on the particular amino acid sequence and are readily identified by comparing the subject portion sequences with known peptide/protein sequence data bases. Preferred unique portions include OPP residues that directly bind and activate (agonize) OPP receptors, especially residues that derive from the EGF-like domains of the disclosed sequences, especially those of the human varieties.

Particular preferred OPP peptides are listed here. These peptides are shown by functional assays disclosed herein to have biological activity including axon outgrowth and/or orienting activity. It is apparent to those of ordinary skill in the art that substitutions of chemically conservative residues can be made while preserving function. Preferred peptides derived from domain V of p75 and p78:

1. NGH AA/SR (SEQ ID NOS:26/27, residues 289–294/ 265–270)
2. VRD RDD N/SLV (SEQ ID NO:26, residues 296–304)
3. VKD KEQ KLV (SEQ ID NO:27, residues 272–280)
4. KHN TE/AG PE (SEQ ID NOS:26/27, residues 308–315/ 284–291)
5. KPF HYD RP WQR AT/SA REA NE (SEQ ID NOS:26/ 27, residues 320–338/296–319)
6. NLH ARR (SEQ ID NO:26, residues 345–350)
7. RFN MEL YKL SGR KSG GV (SEQ ID NOS:26/27, residues 352–368/328–344)
8. RHN TAG RH (SEQ ID NOS:26/27, residues 373–380/ 349–356)
9. KEG FYR DLS KP/SIS/TH/DR KA (SEQ ID NOS:26/27, residues 385–401/361–377)
10. HPV GAA GK/QT (SEQ ID NOS:26/27, residues 408–416/384–392)
11. NQT TGQ (SEQ ID NOS:26/27, residues 418–423/ 394–399)
12. KDG VTG I/LT (SEQ ID NOS:26/27, residues 427–434/ 403–410)
13. AKG Y/FQQ SRS PI/VA P (SEQ ID NOS:26/27, residues 439–451/415–427)

Preferred peptides derived from the C terminal domains of p75 and p78:
14. IKI PAI/AN/P (SEQ ID NOS:26/27, residues 457–459/ 429–435)
15. IKI PVR (SEQ ID NO:40, residues 377–382)
16. STE A/EPA DCD SYC K (SEQ ID NOS:26/27, residues 466–478/442–454)
17. KI/MN MKK YCK/R KDY V/AVQ (SEQ ID NOS:26/ 27, residues 485–499/461–475)

18. KFT I/VNI L/T/ISV YK (SEQ ID NOS:26/27, residues 513–523/489–499)
19. CKC PKI/V (SEQ ID NOS:26/27, residues 545–550/521–526)
20. ADK S/NSL VIQ WRD (SEQ ID NOS:26/27, residues 573–584/549–560)
21. RLR RGD QTL W (SEQ ID NO:26, residues 528–537)
22. RVK RGD NFL W (SEQ ID NO:27, residues 504–513)

Preferred peptides derived from domain VI of p75 and p78:

23. DPC YDE (SEQ ID NOS:26/27, residues 40–45/27–30)
24. RCI PE/DF VNA/S AFG KEV (SEQ ID NOS:26/27, residues 51–65/38–52)
25. SST CGK PP (SEQ ID NOS:26/27, residues 68–75/55–62)
26. A/SSD PKR/K AHP PA/S (SEQ ID NO:26, residues 97–107)
27. LTD LNN PH (SEQ ID NO:26, residues 109–116)
28. LTD LNT AA (SEQ ID NO:27, residues 80–87)
29. NL/MT CWR/Q S (SEQ ID NOS:26/27, residues 117–123/88–94)

The subject peptides may be free or covalently coupled to other atoms or molecules. Frequently the peptides are present as a portion of a larger polypeptide comprising the subject peptide where the remainder of the polypeptide need not be OPP/receptor-derived. Alternatively, the subject peptide may be present as a portion of a "substantially full-length" OPP/receptor which comprises at least about 200, preferably at least about 300, more preferably at least about 400 amino acids of a disclosed polypeptide sequence. The invention provides polypeptides comprising a sequence substantially similar to that of substantially full-length OPPs/receptors. "Substantially similar" sequences share at least about 40%, more preferably at least about 60%, and most preferably at least about 80% sequence identity. Where the sequences diverge, the differences are generally point insertions/deletions or conservative substitutions, i.e. a cysteine/threonine or serine substitution, an acidic/acidic or hydrophobic/hydrophobic amino acid substitution, etc.

The subject poly/peptides are "isolated", meaning unaccompanied by at least some of the material with which they are associated in their natural state. Generally, an isolated poly/peptide constitutes at least about 1%, preferably at least about 10%, and more preferably at least about 50% by weight of the total poly/peptide in a given sample. By pure peptide/polypeptide is intended at least about 60%, preferably at least 80%, and more preferably at least about 90% by weight of total poly/peptide. Included in the subject poly/peptide weight are any atoms, molecules, groups, etc. covalently coupled to the subject poly/peptides, such as detectable labels, glycosylations, phosphorylations, etc.

The subject poly/peptides may be isolated or purified in a variety of ways known to those skilled in the art depending on what other components are present in the sample and to what, if anything, the poly/peptide is covalently linked. Purification methods include electrophoretic, molecular, immunological and chromatographic techniques, especially affinity chromatography and RP-HPLC in the case of peptides. For general guidance in suitable purification techniques, see Scopes, R., Protein Purification, Springer-Verlag, N.Y. (1982).

The subject poly/peptides generally comprise naturally occurring amino acids but D-amino acids or amino acid mimetics coupled by peptide bonds or peptide bond mimetics may also be used. Amino acid mimetics are other than naturally occurring amino acids that conformationally mimic the amino acid for the purpose of the requisite OPP/receptor binding specificity. Suitable mimetics are known to those of ordinary skill in the art and include β-γ-δ amino and imino acids, cyclohexylalanine, adamantylacetic acid, etc., modifications of the amide nitrogen, the α-carbon, amide carbonyl, backbone modifications, etc. See, generally, Morgan and Gainor (1989) Ann. Repts. Med. Chem 24, 243–252; Spatola (1983) Chemistry and Biochemistry of Amino Acids, Peptides and Proteins, Vol VII (Weinstein) and Cho et. al (1993) Science 261, 1303–1305 for the synthesis and screening of oligocarbamates.

The subject poly/peptides have OPP/receptor binding specificity meaning that the subject poly/peptide retains a molecular conformation specific to one or more of the disclosed OPPs/receptors. As such, binding specificity may be provided by an OPP-specific immunological epitope, lectin binding site, etc. However, preferred OPP binding specificity is specificity for an OPP receptor, and vice versa. "Selective binding" is empirically determined by contacting, for example a OPP receptor poly/peptide with a mixture of components and identifying those components that preferentially bind the peptide. Selective binding is most conveniently shown by competition with labeled ligand using recombinant OPP peptide either in vitro or in cellular expression systems as disclosed herein. Generally, selective binding requires a binding affinity of $10^{-6}$M, preferably $10^{-8}$M, more preferably $10^{-10}$M, under in vitro conditions as exemplified below.

The poly/peptides may be modified or joined to other compounds using physical, chemical, and molecular techniques disclosed or cited herein or otherwise known to those skilled in the relevant art to affect their OPP/receptor binding specificity or other properties such as solubility, membrane transportability, stability, toxicity, bioavailability, localization, detectability, in vivo half-life, etc. as assayed by methods disclosed herein or otherwise known to those of ordinary skill in the art. For example, point mutations are introduced by site directed mutagenesis of nucleotides in the DNA encoding the disclosed poly/peptides or in the course of in vitro peptide synthesis.

Other modifications to further modulate binding specificity/affinity include chemical/enzymatic intervention (e.g. fatty acid-acylation, proteolysis, glycosylation) and especially where the poly/peptide is integrated into a larger polypeptide, selection of a particular expression host, etc. Amino and/or carboxyl termini may be functionalized e.g., for the amino group, acylation or alkylation, and for the carboxyl group, esterification or amidification, or the like.

Many of the disclosed poly/peptides contain glycosylation sites and patterns which may be disrupted or modified, e.g. by enzymes like glycosidases. For instance, N or O-linked glycosylation sites of the disclosed poly/peptides may be deleted or substituted for by another basic amino acid such as Lys or His for N-linked glycosylation alterations, or deletions or polar substitutions are introduced at Ser and Thr residues for modulating O-linked glycosylation. Glycosylation variants are also produced by selecting appropriate host cells, e.g. yeast, insect, or various mammalian cells, or by in vitro methods such as neuraminidase digestion. Other covalent modifications of the disclosed poly/peptides may be introduced by reacting the targeted amino acid residues with an organic derivatizing (e.g. methyl-3-[(p-azido-phenyl)dithio]propioimidate) or crosslinking agent (e.g. 1,1-bis(diazoacetyl)- 2-phenylethane) capable of reacting with selected side chains or termini. For therapeutic and diagnostic localization, the subject poly/peptides thereof may be labeled directly (radioisotopes, fluorescers, etc.) or indirectly with an agent capable of providing a detectable signal, for example, a heart muscle kinase labeling site.

Using the disclosed OPP poly/peptides, OPP receptors are identified by a variety of techniques known to those skilled in the art where a ligand to the target receptor is known, including expression cloning. For other examples of receptor isolation with known ligand using expression cloning, see, Staunton et al (1989) Nature 339, 61; Davis et al (1991) Science 253, 59; Lin et al (1992) Cell 68, 775; Gearing et al (1989) EMBO 8, 3667; Aruffo and Seed (1987) PNAS 84, 8573 and references therein. Generally, COS cells are transfected to express a fetal brain cDNA library or PCR product and cells producing poly/peptides which bind a target OPP poly/peptide are isolated. Alternatively, PCR primers based upon sequences disclosed herein are used to amplify PCR product from such tissues/cells. Other receptor/ligand isolation methods using immobilized ligand or antibody are known to those skilled in the art.

Additional OPP peptides with receptor binding specificity are identified by a variety of ways including crosslinking to receptor or specific antibody, or preferably, by screening such peptides for binding or disruption of OPP-OPP receptor binding. For example, OPP routants, including deletion routants are generated from and used to identify regions important for specific protein-ligand or protein-protein interactions, for example, by assaying for the ability to mediate axon outgrowth in cell-based assays as described herein. Further, structural x-ray crystallographic and/or NMR data of the disclosed protein are used to rationally design binding molecules of determined structure or complementarity for modulating axon outgrowth and guidance.

Additional OPP/receptor-specific agents include specific antibodies that can be modified to a monovalent form, such as Fab, Fab', or Fv, specifically binding oligopeptides or oligonucleotides and most preferably, small molecular weight organic receptor agonists. For example, the disclosed OPP and OPP receptor peptides are used as immunogens to generate specific polyclonal or monoclonal antibodies. See, Harlow and Lane (1988) Antibodies, A Laboratory Manual, Cold Spring Harbor Laboratory, for general methods. Anti-idiotypic antibody, especially internal imaging anti-ids are also prepared using the disclosures herein.

Other prospective OPP/receptor specific agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful agents are identified with assays employing a compound comprising the subject poly/peptides or encoding nucleic acids. A wide variety of in vitro, cell-free binding assays, especially assays for specific binding to immobilized compounds comprising OPP/receptor poly/peptide find convenient use. See, e.g. Fodor et al (1991) Science 251, 767 for the light directed parallel synthesis method. Such assays are amenable to scale-up, high throughput usage suitable for volume drug screening. While less preferred, cell-based assays may be used to determine specific effects of prospective agents on e.g. OPP receptor function.

Useful agents are typically those that bind to and activate an OPP receptor, e.g. induce axon outgrowth and/or orientation. Preferred agents are receptor-specific and do not cross react with other neural or lymphoid cell membrane proteins. Useful agents may be found within numerous chemical classes, though typically they are organic compounds; preferably small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways as described above, e.g. to enhance their proteolytic stability. Other methods of stabilization may include encapsulation, for example, in liposomes, etc. The subject binding agents are prepared in any convenient way known to those skilled in the art.

For therapeutic uses, the compositions and agents disclosed herein may be administered by any convenient way. Small organics are preferably administered orally; other compositions and agents are preferably administered parenterally, conveniently in a pharmaceutically or physiologically acceptable carrier, e.g., phosphate buffered saline, or the like. Typically, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells.

As examples, many of the disclosed therapeutics are amenable to direct injection or infusion, topical, intratracheal/nasal administration e.g. through aerosal, intraocularly, or within/on implants e.g. fibers e.g. collagen, osmotic pumps, grafts comprising appropriately transformed cells, etc. A particularly useful application involves coating, imbedding or derivatizing fibers, such as collagen fibers, protein polymers, etc. with theraputic peptides. Other useful approaches are described in Otto et at. (1989) J Neuroscience Research 22, 83–91 and Otto and Unsicker (1990) J Neuroscience 10, 1912–1921. Generally, the amount administered will be empirically determined, typically in the range of about 10 to 1000 µg/kg of the recipient. For peptide agents, the concentration will generally be in the range of about 50 to 500 µg/ml in the dose administered. Other additives may be included, such as stabilizers, bactericides, etc. These additives will be present in conventional amounts.

The invention provides isolated nucleic acids encoding the disclosed poly/peptides. An "isolated" nucleic acid is present as other than a naturally occurring chromosome or transcript in its natural state and is typically joined in sequence to at least one nucleotide with which it is not normally associated on a natural chromosome.

Nucleic acids with substantial sequence similarity hybridize under low stringency conditions, for example, at 50° C. and SSC (0.9M saline/0.09M sodium citrate) and remain bound when subject to washing at 55° C. with SSC. Regions of non-identity of substantially similar nucleic acid sequences preferably encode redundant codons.

A partially pure nucleotide sequence constitutes at least about 5%, preferably at least about 30%, and more preferably at least about 90% by weight of total nucleic acid present in a given fraction.

Unique portions of the disclosed nucleic acids are of length sufficient to distinguish previously known nucleic acids. Thus, a unique portion has a nucleotide sequence at least long enough to define a novel oligonucleotide, usually at least about 18 bp in length.

The invention also provides for the disclosed nucleic acids modified by transitions, transversions, deletions, insertions, or other modifications such as alternative splicing and also provides for genomic sequences, and gene flanking sequences, including regulatory sequences; included are DNA and RNA sequences, sense and antisense. Preferred DNA sequence portions encode the preferred amino acid sequence portions disclosed above. For antisense applications where the inhibition of expression is indicated, especially useful oligonucleotides are between about 10 and 30 nucleotides in length and include sequences surrounding the disclosed ATG start site, especially the oligonucleotides defined by the disclosed sequence beginning about 5 nucleotides before the start site and ending about 10 nucleotides after the disclosed start site.

Typically, the invention's OPP/receptor poly/peptide encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. According to a particular embodiment of the invention, portions of the coding sequence are spliced with heterologous sequences to produce soluble, secreted fusion proteins, using appropriate signal sequences and optionally, a fusion partner such as β-Gal.

The OPP/receptor encoding nucleic acids can be subject to alternative purification, synthesis, modification, sequencing, expression, transfection, administration or other use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, New York, N.Y., 1992) or that are otherwise known in the art.

The invention also provides vectors comprising nucleic acids encoding OPP/receptor poly/peptides. A large number of vectors, including plasmid and viral vectors, have been described for expression in a variety of eukaryotic and prokaryotic hosts. Advantageously, vectors will often include a promotor operably linked to the OPP/receptor poly/peptide-encoding portion, one or more replication systems for cloning or expression, one or more markers for selection in the host, e.g. antibiotic resistance. The inserted coding sequences may be synthesized, isolated from natural sources, prepared as hybrids, etc. Suitable host cells may be transformed/transfected/infected by any suitable method including electroporation, CaCl$_2$ mediated DNA uptake, viral infection, microinjection, microprojectile, or other methods.

Appropriate host cells include bacteria, archebacteria, fungi, especially yeast, and plant and animal cells, especially mammalian cells. Of particular interest are *E. coli, B, Subtilis, Saccharomyces cerevisiae*, SF9 cells, C129 cells, 293 cells, Neurospora, and CHO, COS, HeLa cells, immortalized mammalian myeloid and lymphoid cell lines, and pluripotent cells, especially mammalian ES cells and zygotes. Preferred expression systems include COS-7, 293, BHK, CHO, TM4, CV1, VERO-76, HELA, MDCK, BRL 3A, W138, Hep G2, MMT 060562, TRI cells, and baculovirus systems. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art.

For the production of stably transformed cells and transgenic animals, the subject nucleic acids may be integrated into a host genome by recombination events. For example, such a nucleic acid can be electroporated into a cell, and thereby effect homologous recombination at the site of an endogenous gene, an analog or pseudogene thereof, or a sequence with substantial identity to an OPP/receptor-encoding gene. Other recombination-based methods such as nonhomologous recombinations, deletion of endogenous gene by homologous recombination, especially in pluripotent cells, etc., provide additional applications. Preferred transgenics and stable transformants over-express or under-express (e.g. knock-out cells and animals) a disclosed OPP/receptor gene and find use in drug development and as a disease model. Methods for making transgenic animals, usually rodents, from ES cells or zygotes are known to those skilled in the art.

The compositions and methods disclosed herein may be used to effect gene therapy. See, e.g. Zhu et al. (1993) Science 261, 209–211; Guiterrez et al. (1992) Lancet 339, 715–721. For example, cells are transfected with OPP/receptor-encoding sequences operably linked to gene regulatory sequences capable of effecting altered OPP/receptor expression or regulation. To modulate OPP/receptor translation, target cells may be transfected with complementary antisense polynucleotides. For gene therapy involving the grafting/implanting/transfusion of transfected cells, administration will depend on a number of variables that are ascertained empirically. For example, the number of cells will vary depending on the stability of the transfered cells. Transfer media is typically a buffered saline solution or other pharmacologically acceptable solution. Similarly the amount of other administered compositions, e.g. transfected nucleic acid, protein, etc., will depend on the manner of administration, purpose of the therapy, and the like.

The following examples are offered by way of illustration and not by way of limitation.

EXAMPLES

1. Development of a novel assay for commissural axon outgrowth

In our published work, the outgrowth-promoting activity of floor plate cells was assayed on E11 rat dorsal spinal cord. In these experiments, two-segment stretches of E11 dorsal spinal cord are cocultured with floor plate in collagen gels for 40 hr (Tessier-Lavigne et at, 1988). In initial attempts to screen potentially more abundant tissue sources for activity, we found that this assay is very sensitive to impurities present in crude tissue homogenates, so that it was necessary to identify a more robust assay. We therefore tested whether the floor plate could also promote the outgrowth of commissural axons from older spinal cord, which was expected to be less fragile. When small pieces of dorsal spinal cord (approximately 50 μm×50 μm) were cultured with floor plate in collagen gels, dramatic outgrowth of axons was observed after 16hr of culture; at that time, little or no outgrowth was observed in cultures without floor plate. Floor plate-conditioned medium had the same effect as floor plate tissue; moreover, when conditioned medium was titered, it was found that it was as effective in promoting outgrowth from E13 explants as from E11 explants.

The E13 tissue was found to be more robust than the E11 tissue; i.e., it was not killed by crude extracts. It was therefore used to screen for a more abundant source of activity and to purify the activity.

2. Identification of embryonic brain as a source of commissural axon outgrowth-promoting activity Floor plate tissue is too small a source of commissural axon outgrowth-promoting activity to effect a purification. To try to identify a more abundant source of activity, we screened a number of adult and embryonic tissues. Because we were concerned that activity might be present at too low a level to be detected, we first sought to identify a few steps of purification and enrichment of the activity in floor plate homogenates, with the aim of applying these steps to potentially more abundant sources.

When floor plate homogenates were applied to dorsal spinal cord explants, robust commissural axon outgrowth was evoked by these homogenates. When the homogenates were fractionated into soluble and membrane fractions, essentially all the activity was found associated with the membranes. We found that the activity in floor plate membranes could be solubilized by exposure to 1M NaCl.

We therefore screened several tissues for the presence of commissural axon outgrowth activity by making tissue homogenates, isolating a membrane fraction, and extracting this fraction with 1M NaCl. This showed that embryonic brain contained commissural axon outgrowth activity. Activity was detected in both rat and chick brain, but the latter was used for further characterization and purification due to the relative ease with which it can be isolated.

3. Molecular dissection of the activity in embryonic brain

We analyzed whole chick embryos (E4 through E7) and dissected brains (E10 and E13) as to relative ease of dissection and ability to accumulate large amounts of source material, through the isolation of membrane fractions with subsequent 1M NaCl extraction and E13 assay. We found that E10 brain was roughly equivalent to E7 whole embryo in terms of the speed with which we could accumulate total activity; however, because we expected the protein composition of brain tissue to be less complex, we decided to use this tissue as the source material for our purification. Likewise, although homogenization of embryonic brain tissue using either a Potter-Ehrehjem homogenizer or Waring blender led to equal recoveries of the activity, the specific activity in salt extracts was higher in the former, and thus the gentler method of homogenization was used. Differential centrifugation experiments identified the microsomal membrane fraction as containing almost all of the salt-extractable activity. Although this differential centrifugation strategy leads to only modest increases in specific activity, we nonetheless retained these steps at the onset of the purification scheme because we expected to decrease the complexity of the eventual salt extract by increasing the homogeneity of the membrane fraction.

Differential salt extraction of microsomal membrane fractions led to a large increase in specific activity. Therefore, a low salt wash at approximatley 500 mM NaCl followed by a high salt extraction of the activity at approximately 1M NaCl was routinely used to prepare a soluble form of the activity amenable to column chromatography.

The first chromatography step (Heparin Sepharose CL-6B) served both to purify and to concentrate the activity. (The entire purification scheme is diagrammed in FIG. 1.) In order to maximize the purification, the column was loaded at approximately 0.9M NaCl, a salt concetration at which the activity partitioned into the stationary phase just enough to prevent bleed-through during loading and washing. The 2M NaCl eluate from the column contained all of the outgrowth promoting activity present in the column fractions. In addition, however, we discovered that the flow-through fraction, containing the bulk of the protein, contained an activity which synergizes with eluted activity. At low concentrations of the eluate (which we term the "α" Fraction), the flow-through fraction (the "β" Fraction) acted to enhance the outgrowth (in terms of fascicle length, number, and thickness) of commissural axons elicited by the former. At higher concentrations of α the effect of β is less pronounced. The β Fraction by itself caused no outgrowth in these experiments. In order to maximize the sensitivity of the assay to the active component in the α Fraction, β was routinely included in the assays of fractions generated at this step of the purification and beyond. We term the activity in the β Fraction which synergizes with the α Fraction "SA" (for "synergizing activity"). In subsequent experiments, SA was shown to be stable to boiling and freeze/thawing, retained by 10K MW cut-off filters, and protease sensitive. Purification, characterization and gene cloning of β are performed analogously to that of α.

Figure 2:
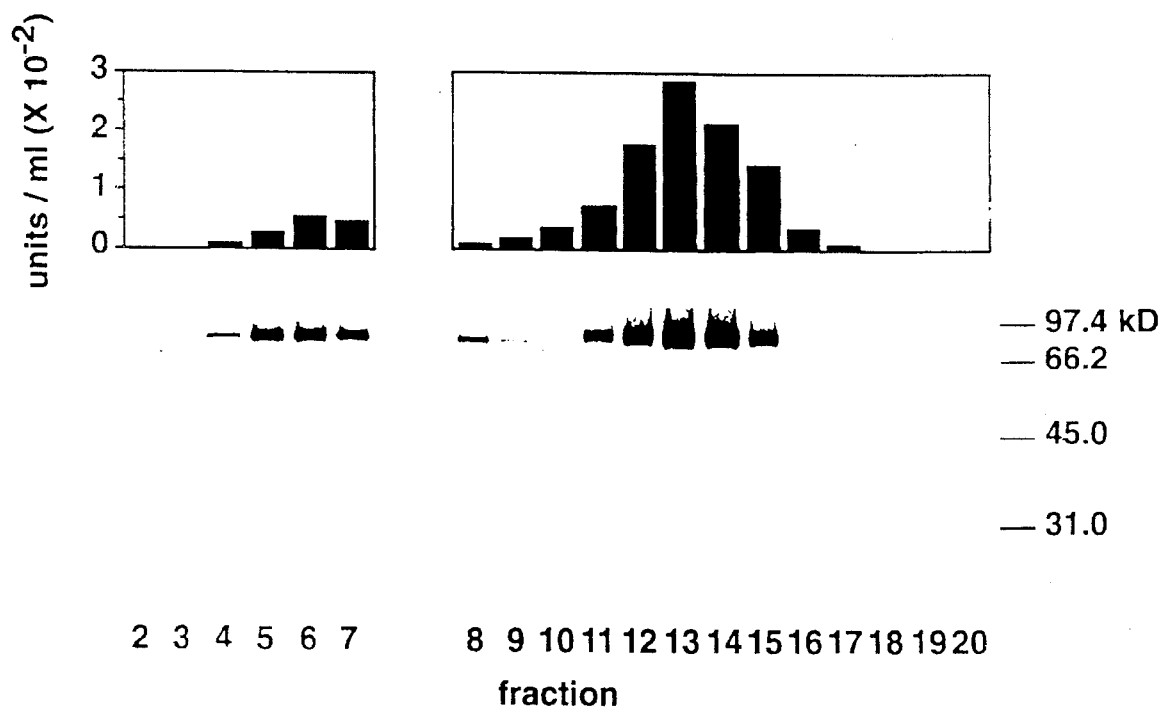
FIG. 2: SDS-PAGE and activity profile of IMAC fractions (final step in purification). Two hundred μl of each fraction from the IMAC chromatography step of the purification of p75 and p78 was TCA precipitated and subjected to SDS-PAGE and silver staining. p75 is seen to elute in fractions 4–8, while p78 elutes in fractions 10–16; the activity profile mirrors the presence of the two proteins in the fractions.

Three subsequent steps of purification follow: Wheat Germ Agglutinin (WGA) Agarose, Heparin Sepharose High Performance (HSHP), and Immobilized Metal Adsorption Chromatography (IMAC) on a $Zn^{2+}$-charged resin. At this last step, outgrowth-promoting activity was found to co-chromatograph separately with two proteins: one of 75 kD (as assessed by SDS-PAGE) which eluted isocratically from the column at approximately a pH of 6.5, and one of 78 kD which eluted during the application of a decreasing pH gradient at a pH of approximately 6.1. As judged by silver staining of overloaded SDS-PAGE gels of the active fractions (FIG. 2), the two proteins have been purified to homogeneity. (A faint band of slightly lower molecular weight is present in the fractions containing p75, in exactly the same relative abundance as p75, indicative of a differentially glycosylated form of the protein.)

To develop the purification of p75 and p78, approximately 20,000 E10 chick brains were used. From 2000 E10 chick brains (one purification run), approximately 10 μg p78 and 3 μg p75 can be obtained after an approximate 30,000-fold purification with an approximately 2% yield.

Figure 3:
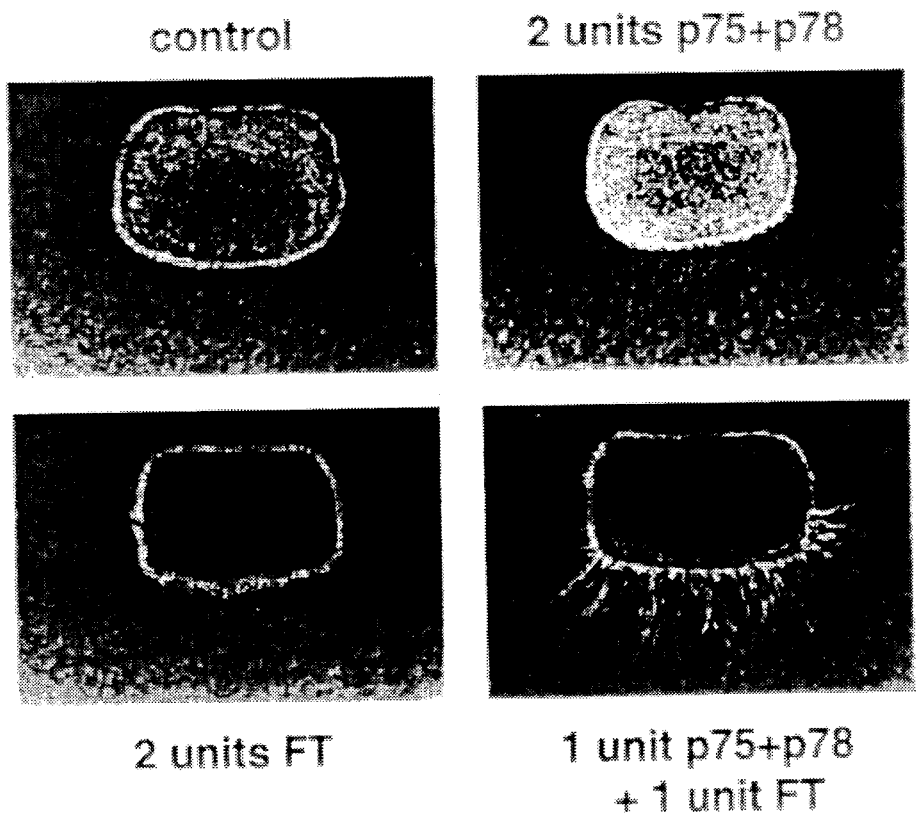
FIG. 3: Demonstration of synergy between p75/p78 and SA (FT=flow-through, or b Fraction) on E11 rat dorsal spinal cord explants. Top left panel shows a control explant cultured only in complete medium for 36 hr. Top right panel shows a similar explant cultured in the presence of two "units" of a mixture of p75 and p78. The bottom left panel shows an explant cultured in the presence of two "units" of SA. In both cases, there is little or no outgrowth of axons into the surrounding collagen matrix. The bottom fight panel shows an explant cultured in the presence of one unit of the p75/p78 mixture and one unit of SA: There is tremendous outgrowth clearly not seen under any of the other conditions. Because only one unit of each of the two fractions suffices to elicit this response, while double that amount of each separately has almost no effect, one can conclude that the two activities are synergistic rather than additive.

4. Requirement for both p75/p78 and SA for reconstitution of floor plate effect on E11 explants Surprisingly, whereas p75 and p78, when added to the medium of E13 explant cultures, were both equally capable of evoking the full response seen when these E13 explants are cocultured with floor plate, the proteins were relatively incapable of causing this robust outgrowth from E11 explants. However, with the addition of SA (i.e., the β Fraction), the full effect was reconstituted. As is seen in FIG. 3, this effect of SA is a true synergy. Two units of either a mix of p75 and p78 or SA alone have little or no effect on an E11 dorsal explant (compare with control), yet culturing such an explant with only one unit of p75/p78 and only one unit of SA leads to robust outgrowth.

5. Protein sequencing of p75 and p78

Purified p75 and p78 from approximately 5000 E10 chick brains (two and one-half purification runs) was trichloroacetic acid (TCA) precipitated and cleaved with cyanogen bromide (CNBr). The resulting peptides were separated by SDS-PAGE and electroblotted to polyvinylidene difluoride (PVDF) membrane, from which they were subjected to gas phase Edman degradation sequencing directly. In addition, purified protein was sequenced directly in order to obtain N-terminal sequence. The following lists sequences obtained that were considered reliable enough for gene cloning purposes (the "M" in brackets at the beginning of most sequences indicates the methionine residue implied by the generation of the peptide by CNBr):

from p78 (N-term) ??????MFAVQT (SEQ ID NO:26, residues 32–37)

(1) [M]ELYKLSGRKSGGVXLNXRH (SEQ ID NO:45)
(2) [M]ELYKLSGQKSGGV (SEQ ID NO:46)
(3) [M]DYGKTWVPFQFYS (SEQ ID NO:26, residues 166–179)
(4) [M]YNKPSRAAITKQNEQEAI (SEQ ID NO:26, residues 185–203)
from p75 (N-term) ANPFVAQQTP (SEQ ID NO:27, residues 16–25)
(1) [M]ELYKLSGRKSGGVXLNXRH (SEQ ID NO:45)
(2) [M]DYGKTWVPYQYYS (SEQ ID NO:27, residues 137–150)

In this scheme, "X" denotes the absence of any phenylthiohydantoin (PTH) derivative observed during that cycle of sequencing. When PTH derivatives are easily assigned in previous and following cycles, this situation is usually due to the presence of a cysteine residue at that position in the peptide. "?" denotes an ambiguous result for that cycle of sequencing; i.e., no assignment could be made. The sequences suggested that at least portions of the two proteins were very homologous, since sequence (1) from p78 and sequence (1) from p75 were identical. However, the above sequences also showed that p75 and p78 are distinct proteins, since sequence (3) from p78 and sequence (2) from p75 are homologous but distinct.

6. RNA isolation

Total RNA was isolated from E10 chick brains as described (Auffray and Rougeon, 1980).

7. PCR amplification of fragments of the cDNAs for p75 and p78 p78

Degenerate oligonucleotide primers were made based upon the amino acid sequences obtained for p78 peptides. These primers represented the sequences both in sense and antisense orientations, as the placement of the sequences relative to one another in the full sequence of the protein was unknown. Because PCR using pairs of these primers yielded very heterogeneous mixtures of products, a nested PCR strategy was employed. In this strategy, primers (presumably) internal to those used in primary reactions are used in secondary PCR in order to selectively amplify bona fide fragments of the cDNA of interest from the mixture of primary reaction products. Using such a strategy, three primers were used to amplify a single 92 bp fragment. Because the sequence of this fragment was found to encode p78 peptide sequence not used for any of the three primers (and found in correct orientation with respect to the primers), this PCR product was a fragment of the cDNA for p78, yielding 62 bp of unique, nondegenerate sequence for the cDNA.

p75

A nested PCR strategy was also used to amplify a fragment of the cDNA encoding p75. Because an alignment of the derived p78 amino acid sequence showed that regions of identity existed between p78 and the B2 chains of laminin (see Sequences, below), and the peptide sequences obtained for p75 suggested that p75 and p78 were very homologous, it was very likely that those regions of identity between p78 and the laminin B2 chains would also be conserved in p75. Furthermore, the alignment allowed a prediction of the relative placement of p75 peptide sequences relative to one another. Therefore, a primer for the second stage of the nested PCR was designed based upon sequences within p78 that were identical to sequences of the laminin B2 chains and were predicted to lie within the amplified fragment generated using the selected first stage PCR primers. Also, the alignment of p78 and laminin B2 sequences allowed sense and antisense primers to be selected in accordance with their expected positions relative to one another.

After performing the nested PCR, restriction digestion of the "single" amplified product eliminated any p78 sequences from the DNA that was subsequently cloned and sequenced. Sequencing of a 377 bp fragment resulting from the PCR and subsequent digestion yielded a derived amino acid sequence that was highly homologous to that of p78; therefore, this fragment was very likely to be a fragment of the gene for p75, which was borne out after the entire cDNA was cloned and sequenced, and the N-terminal sequence obtained for p75 was present at the predicted N-terminus of the mature protein (see below).

8. Library construction and screening

In order to isolate cDNAs corresponding to p78 and p75 an E10 chick brain cDNA library was constructed. A 61 bp $\alpha^{32}$P-dCTP labelled probe to p78 was generated by PCR using primers complementary to the original p78 fragment sequence described above. A 258 bp probe was also generated for p75 by PCR. Using these probes, and probes generated from additional p75 and p78 clones as the screening proceeded, a total of $3\times10^6$ clones of the E10 chick brain cDNA library were screened yielding two partial p78 clones and eleven partial p75 clones. An additional partial p78 clone was identified in a screen of $2\times10^6$ clones from an amplified E2.5 chick spinal cord library.

9. 3' RACE and specifically primed cDNA libraries

Following these screens, cDNAs containing 5' coding sequence of p75 and 3' coding sequence of p78 had not been obtained. A 3' RACE protocol was used to obtain the 3' coding sequence of p78 (as descibed by Frohman and Martin, 1989). The sequence obtained using 3' RACE was used to design a p78 oligonucleotide complementary to sequence 3' of the translational stop codon, which was then used to prime the synthesis of first strand cDNA for the generation of a library enriched in p78 sequences. Similarly, sequence 3' to the translational stop site in one of the p75 cDNAs and sequence at the 5' end of one of the partial p75 cDNA clones were used to generate two primers to prime the first strand synthesis of cDNA libraries designed to obtain the missing 5' sequence of p75. cDNA synthesized in this way was cloned directly into pBluescript (Stratagene). Screens of these plasmid libraries using probes derived from the partial p75 and p78 cDNAs were used to identify cDNAs containing the full coding sequences of p75 and p78.

10. Northern and Southern analysis, and in situ hybridization

Northern analysis suggested that p78 and p75 are each encoded in E10 chick brain by approximately 4 kb transcripts and Southern analysis confirmed that p78 and p75 are each encoded by different genes.

In situ hybridization to E2.5 chick embryo sections and whole mounts revealed that p78 is expressed in the floor plate of the spinal cord, consistent with it contributing to the chemoattractant and outgrowth promoting properties of the floor plate (FIG. 4, top panel). p75 transcripts were found in an apparent ventral to dorsal gradient within the spinal cord, implicating a role for it, too, in axon guidance within the developing spinal cord (FIG. 4, bottom panel). These functions of p75 and p78 are confirmed using function blocking antibodies generated against recombinant p75 and p78.

11. Expressed recombinant p75 and p78

Recombinant p75 and p78 are obtained from culture supernatants and cell extracts of COS cells transfected with SV40-origin containing expression vectors. Large amounts of p75 and p78 are also obtained from recombinant baculovirus infected Sf9 cells.

12. Sequences

The derived amino acid sequences for p75 and p78 are shown in FIGS. 5 and 6. Their structures indicate secreted proteins: Each has an amino-terminal signal sequence (von Heijne, 1983), followed immediately by a mature amino-terminal sequence that is identical to the peptide sequence obtained by microsequencing; there is no other hydrophobic stretch that could represent a transmembrane domain in either protein, nor does either have any indication at its C-terminus of a potential phospholipid linkage. The deduced sizes of the mature proteins are 580 and 566 amino acids for p78 and p75, respectively. There is a very high degree of amino acid sequence homology between the two proteins: 69% identity over the entire coding region (FIG. 7), and even more so in the amino terminal two-thirds of the proteins (see below).

Further analysis of the protein sequences shows that each protein is divided into three structural domains with distinct functional roles. The amino terminal two thirds of the proteins are homologous in amino acid sequence to the amino termini of the B chains of laminin, a large heterotrimeric glycoprotein of the extracellular matrix (its three chains are called A, B1 and B2). This region of homology corresponds to two domains termed VI and V of the laminin chains. Because of this homology, we will also term these regions of p75 and p78 domains VI and V. The remaining C terminal thirds of p75 and p78 are homologous to each other, but diverge completely from the laminin sequence. Each domain is briefly discussed in turn, starting with the middle one.

Figure 8:
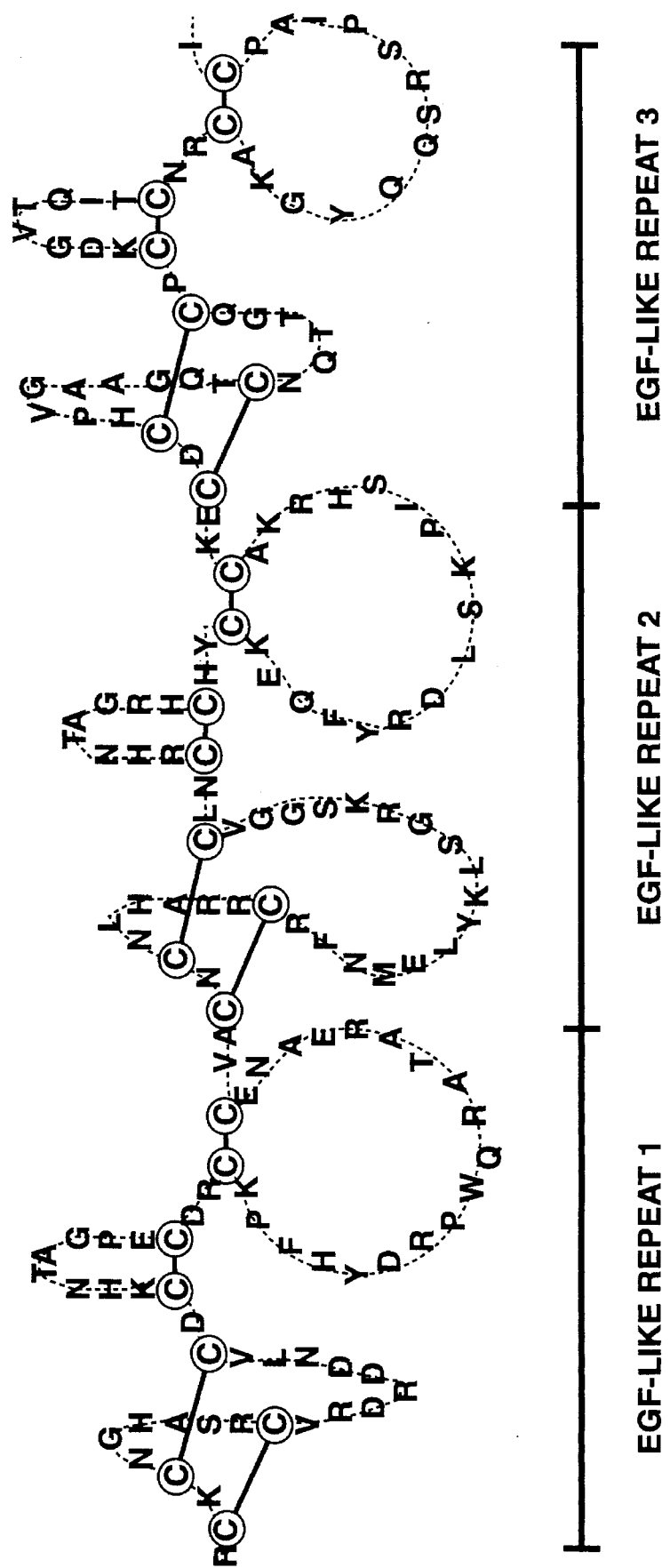
FIG. 8: Predicted structure of domain V of p78, based on the known structure of EGF-like repeats (Cooke et at, 1987), as adapted to laminin by Engel (1989). This domain corresponds to amino acids 285–453 (inclusive) of p78 (SEQ ID NO:26) shown in FIG. 5. Solid lines show disulfide bonds between cysteine residues. The thin line shows the linear polypeptide chain.
Figure 9:
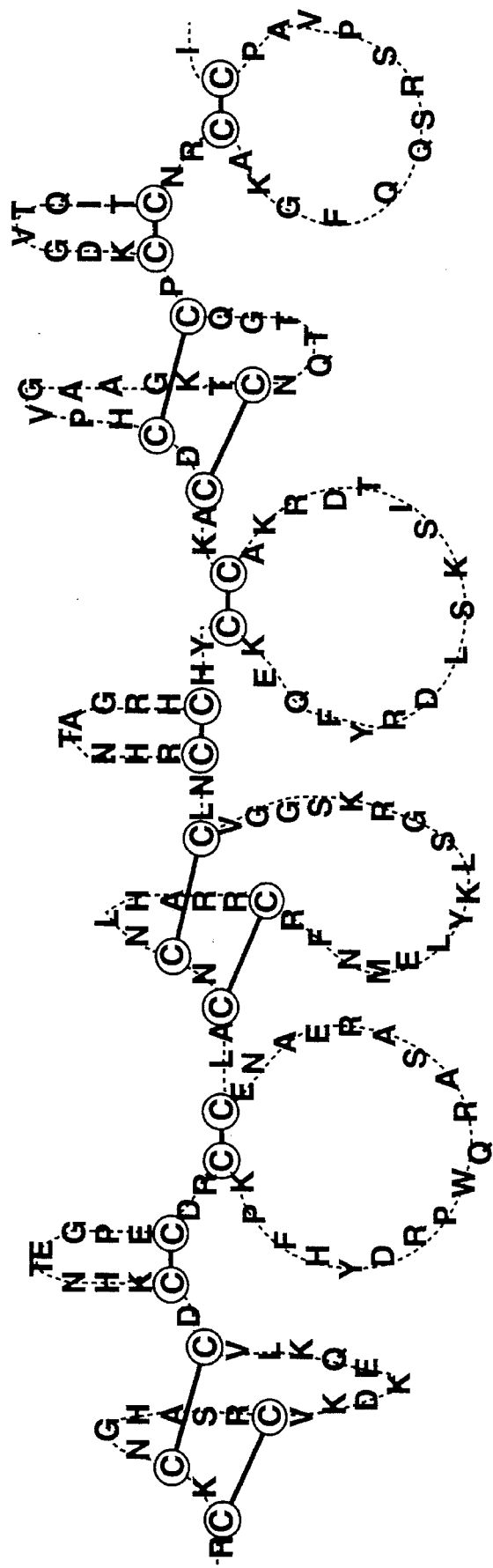
FIG. 9: Predicted structure of domain V of p75, based on the known structure of EGF-like repeats (Cooke et al, 1987), as adapted to laminin by Engel (1989). This domain corresponds to amino acids 261–429 (inclusive) of p75 (SEQ ID NO:27) shown in FIG. 6. Solid lines show disulfide bonds between cysteine residues. The thin line shows the linear polypeptide chain.

Domain V: The amino acid sequences of p75 and p78 are almost identical in this region (FIG. 5: residues 285–453; FIG. 6: residues 261–429; 90% identity over 168 amino acids). The sequences are rich in cysteine residues, which are arranged in a pattern characteristic of so-called EGF-like repeats (Engel, 1989). p75 and p78 each have three EGF-like repeats that make up domain V. The pattern of disulfide linkages in these repeats can be inferred from what is known of the structure of EGF-like repeats (Engel, 1989), leading to the structures of domains V in p75 and p78 that are shown in FIGS. 8 and 9, respectively. The disulfide likages between cysteine residues are oriented to confer a rod-like rigid structure on this region of the polypeptide; loops of amino acids protrude from this backbone, and are available for interaction with other proteins and macromolecules. As in other proteins (Engel, 1989), the loop regions of EGF-like repeats in p75 and p78 are shown to play important roles in cell signaling and adhesions. For example, loop regions are functionally expressed with signal sequences and assayed singly or in combination with other regions, for activity on nerve cells (See, Mayer et al., (1993) EMBO J 125, 1879–1885). Further, residues within the loops are sequentially mutated by insertion, deletion or substitution to identify loops with enhanced or modified activities. Accordingly, peptides comprising p75 and p78-derived EGF-like repeat sequences providing a wide variety of specific neuomodulating activities are provided.

Domain VI: This domain in p75 and p78 (FIG. 5: residues 26 to 284;

FIG. 6: residues 16 to 260) also shows several regions of amino acid sequence homology with domain VI of laminin B chains, in particular with B2 chains of several species (FIGS. 16 and 17). In laminin, domain VI is thought to mediate a calcium dependent assembly of laminin polymers (Yurchenco and Cheng, 1993). In p75 and p78, regions within domain VI are similarly shown to be involved in protein-protein complex formation. Domain VI eptides are functionally expressed with signal sequences and assayed singly or in combination with other regions, for activity on nerve cells (See, supra).

C terminal third: The C-terminal third of p75 and p78 (FIG. 5: resiudes 454 to 605; FIG. 6: residues 430 to 581) is unrelated to laminin sequences. There is a small degree of homology to the C-terminal regions of complement components C3, C4 and C5. In p75 and p78, the C terminal third is rich in basic residues (lysine (K) and arginine (R)), which may explain the tight binding of these proteins to heparin. These regions might therefore also bind heparan-sulfate and mediate binding of p75 and p78 to heparan-sulfate proteoglycans on the surface of the neural cells; this could serve to modulate the functions of these proteins, as binding to heparan-sulfate proteoglycans is known to modulate the function of aFGF (Massague, 1991 ). This domain also contains the amino acid sequence RGD which is shown to mediate cell attachment and guidance. C terminal regions are functionally expressed with signal sequences and assayed singly or in combination with other regions, for activity on nerve cells (See, supra).

13. Mammalian homologues of p75 and p78

The identification of the amino acid sequences of p75 and p78 and the demonstration of regions of homology between the proteins shows that they define a novel family of proteins that are distantly related to the laminin family of extracellular glycoproteins. The differences in sequence between p75/p78 and laminins are sufficient to enable the cloning of cDNAs for the homologues of these genes in other species. We used the chick p75 and p78 sequences to identify conserved amino acid sequences, which were then used to design degenerate oligonucleotide primers for the amplification of a fragment of the mouse p78 cDNA (FIG. 18). This cDNA fragment has been used to isolate the entire coding sequence of mouse p78. This strategy, together with low stringency hybridization screening of genomic and cDNA libraries, is used to isolate p75 from mouse, and p75 and p78 sequences from human.

14. Other members of the p75/p78 family

The disclosed p75 and p78 sequences enable the identification of other members of this novel p75/p78 family of proteins. First, degenerate oligonucleotide primers for PCR amplification of fragments of cDNAs or genomic DNA encoding other family members in various species are designed. p75 and p78 sequences isolated from several species (e.g. chick, mouse and human) are aligned to show which residues are most conserved. Preferred primers are derived from highly conserved residues in the C-terminal third of the proteins, where they diverge most from other proteins (in particular laminin). These oligonucleotides are also used directly to screen libraries at high stringency. Second, cDNA and genomic libraries are screened by low-stringency hybridization using fragments of p75 or p78. Regions of the genes that are most homologous to one another but most divergent from other genes in the database provide the best probes for this purpose.

Mutagenesis studies have suggested that a gene called unc-6 gene is necessary for the guidance of pioneer axons and migrating cells along the body wall in C. elegans. The putative translation product of this gene has never been characterized nor has its function been clarified. The present invention discloses the translation product of unc-6 to be another member of the p75/p78 family with analogous structural and functional properties.

Functions of proteins of the p75/78 family.

p75 and p78 were identified on the basis of their ability to promote commissural axon outgrowth into collagen gels. However, these proteins are shown to have other functions, as well as actions on different classes of neurons and non-neuronal cells.

First, the proteins are shown to promote outgrowth in a variety of other matrices, not just collagen. Collagen is in fact a very unfavorable environment for the growth of commissural axons (these axons normally never encounter collagen in a normal organism). The ability of the proteins to promote outgrowth into this unfavorable environment suggested that the proteins could also promote outgrowth of these axons into other enviroments, such as glial scars in the adult nervous system or other components of the adult spinal cord and assist in the stimulation of spinal axon growth following trauma to the spinal cord.

Second, p75 and p78 were isolated on the basis of their ability to mimic one of the functions of the floor plate (outgrowth promotion). The floor plate also has another important function, namely the ability to orient commissural axon growth (i.e., chemoattraction: Tessier-Lavigne et al, 1988; Placzek et al, 1990a). In previous experiments, we showed that commissural axon orientation activity was found not just in the floor plate but also to a lesser extent in the ventral spinal cord and dermomyotome (Placzek et at, 1990b). The isolation of p75 and p78 reported here enabled us to examine their sites of expression in the embryo and demonstrate restricted distributions that correspond to the previously defined sites of orientation activity: p78 is expressed in floor plate, p75 in ventral spinal cord, and both p75 and p78 are expressed in dermomyotome (FIG. 4). Orientation activity is assayed by expressing p75 and p78 and peptides therefrom in COS cells (see Methods) and testing the ability of the COS cells to orient axon growth in the assay we have previously described (Placzek et al, 1990a). In this way, p75/p78 peptides with specified axon promoting and/or orienting activity are identified.

Third, the proteins have functions other than outgrowth promotion and orientation of axons. As discussed in the previous section, the highly basic C-terminal domain in the two proteins can function as a heparin-binding domain, capable of mediating substrate adhesion of neural and non-neural cells via heparan-sulfate proteoglycans on their surfaces. This is assayed by showing substrate adsorbed p75 and p78 mediation of cell adhesion, and inhibition by heparin. The proteins also have growth factor-like or trophic effects (i.e., effects on the proliferation, survival, and health of neural and non-neural cells). In fact, laminin itself has mitogenic and trophic effects, in addition to its ability to stimulate cell adhesion and motility (Kleinman et al, 1993). Many molecules that have adhesive properties for some cells have also been shown to have anti-adhesive and growth inhibiting properties for other cells (Calof and Lander, 1991); such functions are further characterized in standard assays using recombinant p75 and p78.

Fourth, p75 and p78 have effects on cells other than the commissural neurons that were used to assay their presence during purification. Northern and in situ hybridization analysis shows that p75 and p78 are expressed in brain regions where commissural axons are absent and we have found them to be expressed outside of the nervous system. There are several other examples of molecules affecting the migration of neural cells that also affect non-neuronal cells, in some cases playing a role in tumor cell migration and metastasis (Kleinman, 1993).

METHODS

Tissue culture

Assays using embryonic day 11 (E 11; E0=day of vaginal plug) rat dorsal spinal cord were performed as described (Tessier-Lavigne et al., 1988). For E13 assays, spinal cords were isolated from E13 embryos by dissection in L15 medium (Gibco), opened at the roof plate, and flattened down on the dissection dish in an "open book" configuration (Bovolenta and Dodd, 1990). Electrolytically sharpened tungsten needles were used to dissect approximately 50 µm×50 µm square pieces of dorsal spinal cord in L15 containing 5% heat-inactivated horse serum (HIHS). These dorsal spinal cord explants were embedded in collagen gels as described (Tessier-Lavigne et at., 1988), with four explants in each gel, with or without floor plate. Once the collagen had set, complete medium containing 5% HIHS (Tessier-Lavigne et at, 1988) was added to the wells, and explants were cultured in a humidified incubator in the presence of 5% $CO_2$.

Analysis of floor plate homogenates

Floor plates were dissected from E13 rat spinal cords and kept in L15 on ice. Homogenates were prepared exactly as described by Walter et al (1987), using approximately 1 ml of homogenization buffer per 40 floor plates. After a low speed spin to pellet nuclei and cell debris (1000×g, 10 min, 4° C.), the homogenate was spun at high speed (100,000×g, 1 hr, 4° C.). The supernatant was dialyzed against L15 salts (Gibco) and assayed. The pellet was resuspended in 1M NaCl with protease inhibitors (Walter et at., 1987), incubated for 1 hr at 4° C., and spun again at high speed. The supernatant was dialyzed against L15 salts and assayed.

Analysis of embryonic chick brain activity

E4, E5, E6, and E7 embryos, and E13 embryonic brains were homogenized by douncing with an "A" pestle under conditions described above for floor plate homogenizations. Twenty-five percent homogenates were prepared and centrifuged at 2700 rpm (1000×g) in an SA-600 rotor; the pellets were rehomogenized in one-half the original volume of homogenization buffer and recentrifuged. Supernatants were pooled and volumes adjusted to a minimum of 30 ml; 26.3 ml of each was centrifuged at 50,000 rpm (230,000× $g_{av}$) in a 50.2 Ti rotor (Beckman) for 30 min at 4° C. Pellets were resuspended in less than 5 ml 50 mM Tris-HCl pH 7.5 using a dounce, and a one-half volume of 2M NaCl, 50 mM Tris-HCl pH 7.5 solution was added. After mixing end-over-end at 4° C. overnight, the membranes were centrifuged at 70,000 rpm (200,000×$g_{av}$) in an RP100-AT4 rotor (Dupont/Sorvall) for 23 min at 4° C. Supernatants were assayed after microdialysis against F12 medium (see below). E10 brains were found easier to dissect and yielded nearly as much activity.

Biochemical purification

Buffers

| HB B | 20 mM | sucrose |
|---|---|---|
| | 10 mM | HEPES-NaOH pH 7.5 |
| | *1 mM | EDTA pH 8.0 |
| | *2 µg / ml | leupeptin |
| | *2 µg / ml | aprotinin |
| | *1 µg / ml | pepstatin A |
| HB2: | | HB1 + *1 mM PMSF |

| | | |
|---|---|---|
| RB: | 10 mM | HEPES-NaOH pH 7.5 |
| | *2 mM | EDTA pH 8.0 |
| | *4 µg / ml | leupeptin |
| | *4 µg / ml | aprotinin |
| | *2 µg / ml | pepstatin A |
| SB1: | 1.5 M | NaCl |
| | 10 mM | HEPES-NaOH pH 7.5 |
| SB2: | 1.1 M | NaCl |
| | 10 mM | HEPES-NaOH pH 7.5 |
| | *1 mM | EDTA pH 8.0 |
| | *2 µg / ml | leupeptin |
| | *2 µg / ml | aprotinin |
| | *1 µg / ml | pepstatin A |
| A1: | 900 mM | NaCl |
| | 10 mM | HEPES-NaOH pH 7.5 |
| B1: | 2 M | NaCl |
| | 10 mM | HEPES-NaOH pH 7.5 |
| A2: | 500 mM | NaCl |
| | 10 mM | HEPES-NaOH pH 7.5 |
| | 100 µM | $CaCl_2$ |
| | 10 µM | $MnCl_2$ |
| B2: | | A2 + 700 mM N-acetylglucosamine |
| DB: | 500 mM | N-acetylglucosamine |
| | 20 mM | Tris-HCl pH 8.0 |
| A3: | 20 mM | Tris-HCl pH 8.0 |
| B3: | | A3 + 2 M NaCl |
| A4: | 20 mM | $NaP_i$ pH 7.5 (dilute $Na_2HPO_4$, adjust pH with o-phosphoric acid) |
| | 1.5 M | NaCl |
| B4: | 20 mM | $NaP_i$ pH 3.0 (dilute $NaH_2PO_4$, adjust pH with o-phosphoric acid) |
| | 1.5 M | NaCl |

Buffer pH was adjusted at ambient temperature; components indicated with an asterisk were added directly before use. All buffers were used ice cold except for A1, B1, A3, B3, A4, and B4, which were used at 4° C.

Chromatography columns

Heparin-Sepharose CL-6B (HS CL-6B)

column: Bio-Rad Econo-Column with flow adapter, 2.5 cm×20 cm resin: Heparin Sepharose CL-6B, Pharmacia Wheat Germ Agglutinin Agarose (WGA Agarose)

column: Bio-Rad Poly-Prep Column, 1 ml bed volume resin: Wheat Germ Agglutinin Agarose, Vector Laboratories Heparin-Sepharose High Performance (HSHP)

column: Pharmacia HR 5/10 Column, 5 mm×10 cm resin: Heparin Sepharose High Performance, Pharmacia Immobilized Metal Adsorption Chromatography (IMAC)

column: Pharmacia HR 5/2 Column, 5 mm×2.5 cm resin: Chelating Sepharose High Performance, Pharmacia Columns (except the WGA Agarose column, which was freshly poured with new resin for each purification run) were cleaned between runs with 6M guanidinium HCl/20 mM Tris-HCl pH 8.0 (except for the IMAC column, which in addition was then stripped with 0.5M EDTA), and were stored in 0.1% $NAN_3$. All chromatography was performed at 4° C.

Purification procedure

Day one (1) For a single purification run, on a single day approximately 1000 E 10 chick brains were dissected out into 1 liter L15 medium on ice over a period of approximately 2.5 hours. These dissected brains usually included a small portion of cervical spinal cord.

(2) The brains were kept on ice prior to homogenization. After pouring off as much L15 as possible, approximately 25 ml brains were measured into a 50-ml polypropylene conical tube, and 25 ml Buffer HB1 were added. The tube was capped and inverted several times to wash the brains. The brains were poured into a small kitchen strainer to drain off excess buffer, and then transferred into a 55-ml Potter-Ehrehjem homogenizer on ice. Twenty-five ml Buffer HB1 and 0.5 ml 100 mM PMSF (in 2-propanol at ambient temperature) were added, and the brains were homogenized immediately at top speed: five up-and-down strokes followed by a pause on ice for 1 minute, followed by five additional up-and-down strokes. Usually, 1000 brains were homogenized in a total of eight batches, which were then pooled on ice, yielding approximately 360 ml of crude homogenate.

(3) The crude homogenate was aliquoted into 50-ml Oak Ridge tubes and centrifuged at 2700 rpm (1000×g) in an SA-600 rotor (Dupont/Sorvall) for 10 minutes at 4° C. The supernatants were pooled on ice (for a total of approximately 200 ml), and the pellets were vortexed to resuspend them. Fifteen ml Buffer HB2 was added to each tube per 40 ml crude homogenate originally present, and after mixing, the resuspended pellets were transferred sequentially to the homogenizer on ice and homogenized as before using one up-and-down stroke. Each was returned to its Oak Ridge tube and centrifuged at 2700 rpm in an SA-600 rotor for 10 minutes at 4° C. The supernatants were pooled with those obtained previously at this stage for a total of approximately 320 ml low speed supernatant (LSS).

(4) The LSS was aliquoted into 40-ml Oak Ridge tubes and centrifuged at 8300 rpm (10,000×g) in an SA-600 rotor for 10 minutes at 4° C. The supernatants were pooled on ice (a total of approximately 240 ml), and 25 ml Buffer HB2 was added to each tube per 40 ml LSS originally present. The pellets were resuspended by vortexing, and then sequentially transferred to the homogenizer on ice and homogenized as before using one up-and-down stroke. Each was returned to its Oak Ridge tube and centrifuged at 8300 rpm in an SA-600 rotor for 10 minutes at 4° C. The supernatants were pooled with those obtained previously at this stage for a total of approximately 450 ml medium speed supernatant (MSS).

(5) The MSS was aliquoted into 26.3 ml capacity polycarbonate bottles and centrifuged at 50,000 rpm (230,000× $g_{av}$) in a 50.2 Ti rotor (Beckman) for 35 minutes at 4° C. After discarding the supernatants, 4 ml Buffer RB was added to each tube per 26 ml MSS originally present and the pellet was separated from the tube with repeated squirts of the added buffer by using a Pipetman P-1000. The buffer and pellet were transferred to a 50-ml conical tube on ice using a 10-ml pipette; the centrifuge tube was rinsed with 1 ml Buffer RB and this rinse pooled with the previously transferred material. The contents and rinses of every six centrifuge tubes were pooled into one conical tube. Sequentially, the contents of each conical tube were transferred into a 40-ml dounce and homogenized with 10 up-and-down strokes of an "A" pestle. This homogenate was transferred back into its 50-ml conical tube, frozen in liquid nitrogen, and stored at −80° C. A total of approximately 120 ml high speed pellet (HSP) homogenate was obtained.

Day two (6) The above steps were repeated on another day with another 1000 embryonic chick brains to yield HSP homogenate.

Day three (7) The HSP homogenate derived from 2000 embryonic chick brains (in 50-ml conical tubes) was thawed quickly in a 37° C. circulating water bath and pooled in a 2 liter beaker on ice. Using a 3.5×0.5 inch magnetic stir bar, the homogenate was stirred in this beaker at medium speed (Thermolyne Nuova II, setting #6), and Buffer SB1 was added at the rate of approximately 1.5 ml/min using a peristaltic pump until the conductance of 10 µl homogenate added to 1 ml of $H_2O$ was approximately 520 µS/cm. (Conductances were measured using a Radiometer CDM80 meter possessing a CDC114 cell having a cell constant of 1 $cm^{-1}$.) At this point, the homogenate was stirred for 1 hour of additional time at a low setting (#3). The homogenate was aliquoted into five 75-ml capacity polycarbonate bottles and centrifuged at 35,000 rpm (100,000×$g_{av}$) in a 45 Ti rotor (Beckman) for 2 hours at 4° C. After discarding the supernatants, 25 ml of Buffer SB2 was added to each tube, and the pellets were separated from the walls of the tube with repeated squirts of the added buffer by using a Pipetman P-1000. For each tube, the buffer and pellet were transferred into a 40-ml dounce; the centrifuge tube was rinsed with 15 ml Buffer SB2 and this rinse was then pooled with the buffer and pellet in the dounce. After homogenizing with 10 up-and-down strokes of an "A" pestle, the homogenates of the pellets were pooled in a 600-ml beaker on ice. Using a 2.5×(5/16)-inch stir bar, this homogenate was then stirred on ice for 1 hour at a low setting (#4). A total of approximately 240 ml of low salt wash pellet (LSWP) homogenate was obtained.

(8) The LSWP homogenate was aliquoted into four 45 Ti bottles and centrifuged at 35,000 rpm in a 45 Ti for 2 hours at 4° C. The supernatants were recovered and stored at 4° C. overnight.

Day four

This supernatant was aliquoted into four bottles and centrifuged again at 35,000 rpm in a 45 Ti rotor for 2 hours at 4° C. All but approximately the last milliliter of supernatant from each bottle was recovered and pooled on ice. A total of approximately 200 ml high salt extract (HSE) was obtained.

(9) While stirring the HSE on ice (using a 2.5×(5/16)-inch stir bar and a medium setting (#5)), ice cold 10 mM HEPES-NaOH pH 7.5 was added dropwise until the conductivity of 10 µl of this HSE added to 1 ml $H_2O$ was approximately 1000 µS/cm.

(10) While diluting the HSE, the HS CL-6B column was equilibrated with 375 ml Buffer A1 at a flow rate of 2.5 ml/min (column run on a Bio-Rad Econo System). The diluted HSE was loaded onto the column at a flow rate of 1.5 ml/min. The flow-through was collected beginning 80 min after the start of loading and ending approximately 40 min after the last diluted HSE had been loaded onto the column. This flow-through fraction was the β Fraction. The β Fraction was frozen in 40-ml aliquots in liquid nitrogen and stored at −80° C. The column was washed with a total of 300 ml Buffer A1 at a flow rate of 1.5 ml/min. The bound protein was eluted with Buffer B1 at a rate of 1.5 ml/min. The peak of eluted protein was collected manually in a volume of approximately 30 ml using absorbance at 280 nm to monitor the column efflux for the beginning of the eluate peak. To the eluate fraction was added 30 µl of 1 mg/ml pepstatin A (in DMSO) and 60 µl of a solution of 1 mg/ml aprotinin and 1 mg/ml leupeptin. This eluate fraction was the α Fraction, which was stored at 4° C. overnight.

Day five

(11) The α Fraction was concentrated to a final volume of less than 1.5 ml in a 50-ml Amicon ultrafiltration cell at 55 psi nitrogen employing a YM30 membrane. The cell and membrane were washed with 0.5 ml Buffer A2 and pooled with the concentrate. The WGA Agarose column was washed with 50 ml of Buffer A2 under gravity flow. This column was loaded with the concentrate in 0.7 ml (maximum volume) batches, waiting 30 minutes between additional loadings. The column was then washed with two 1-ml volumes of Buffer A2, followed by 20 ml of Buffer A2. The column elution was begun with 0.7 ml Buffer B2, and the eluate was discarded. Elution was continued with an additional 0.3 ml Buffer B2, and the eluate was saved. After 1 hour, the elution was continued with 1 ml and then 0.7 ml Buffer B2, pooling with the previous eluate for a total WGA Agarose eluate of 2 ml.

(12) The WGA Agarose eluate was diluted with 1.3 ml Buffer DB while undergoing gentle vortexing. The HSHP column was equilibrated with 20 ml 85% Buffer A3/15% Buffer B3 at 0.5 ml/min. (This column and IMAC column were run on a Waters 650E system having a model 441 Detector.) The diluted WGA Agarose eluate was loaded into the sample loop using a silanized syringe and injected onto the column at a flow rate of 0.1 ml/min. The column was then washed with 85% Buffer A3/15% Buffer B3 at this flow rate for a total of 90 minutes for the load and the wash combined. The valve was returned to "load" position, and the column was eluted with a linear gradient from 50% Buffer A3/50% Buffer B3 to 25% Buffer A3/75% Buffer B3 over a period of 200 minutes at 0.1 ml/min, collecting 0.5 ml fractions into 1.5 ml silanized polypropylene tubes.

(13) To each of the six or seven fractions containing most of the protein eluting in the peak centered at approximately 1.5 mS/cm (10 µl fraction added to 1 ml $H_2O$, corresponding to approximately 1.35M NaCl), 22.6 µl 0.2M $NaH_2PO_4$ was added by layering the solution on the denser solution of the eluate, and then vortexing quickly. The fractions used were determined by counting from the end of the peak back to just at or over the half-height point on the leading side of the peak. The IMAC column was equilibrated at 0.5 ml/min with 75% Buffer A4/25% Buffer B4 for at least 10 minutes, and then the column was charged with 0.5 ml 0.1M $ZnSO_4$ at the same flow rate. The column was washed sequentially at 0.5 ml/min with 75% Buffer A4/25% Buffer B4 for 10 minutes, (then with the valve back at "load" position) 25% Buffer A4/75% Buffer B4 for 10 minutes, and finally with 75% Buffer A4/25% Buffer B4 for 20 minutes. The sample loop was loaded with the pooled, adjusted HSHP column fractions using a silanized syringe, and the contents of the loop were injected onto the column at 0.5 ml/min. After washing for an additional 1 minute before returning the valve to "load" position, the column was eluted with a linear gradient from 75% Buffer A4/25% Buffer B4 to 25% Buffer A4/75% Buffer B4 over a period of 20 min at 0.5 ml/min, with a 20 min wash at the end conditions thereafter. One ml fractions were collected into 1.5 ml silanized polypropylene tubes; p75 eluted isocratically (at a pH of approximately 6.5) after the flow-through, and p78 eluted in a peak centered on approximately pH 6.1.

Preparation of fractions for assay

In order to assay fractions from beyond the crude homogenate (which itself was not assayed) through the HSE fractions, 1 ml volumes were adjusted with 4M NaCl to 1M NaCl (if not already in high salt) and were mixed end-over-end at 4° C. for 1 hr. Salt-stripped membranes were removed by centrifugation for 100 min at 40,000 rpm (70,000×$g_{av}$) in a RP100-AT4 rotor (Dupont/Sorvall) with microfuge tube adapters. Aliquots of these fractions and those from the HSE step through the end of the purification were adjusted to at least 1M NaCl (if nescessary) and 1 mg/ml ovomucoid in order to stabilize the activity against freeze/thaw and dilution, and to prevent wheat germ agglutinin that had leached off the WGA Agarose column from (1) rebinding to the active protein during dialysis and (2) inhibiting outgrowth from the explants by itself. Ovomucoid alone has no effect in the E11 or E13 assays.

Volumes (between 0.1–0.2 ml) of fractions or dilutions of fractions to be assayed for activity were prepared by dialysis against F12 medium at a flow rate of 1 ml/min for at least three hours in a Gibco/BRL microdialyzer using Spectrapor 2 (Spectrum) dialysis membrane. Routinely, samples were brought up to a final volume of 0.4 ml with F12 medium (and 0.2 ml β Fraction dialyzed against F12, if the fractions were from a stage in the purification beyond the HS CL-6B column), and other components required to complete the medium (Tessier-Lavigne et al, 1988). Samples were warmed to 37° C. before addition to the explant cultures.

E11 and E13 assays were prepared as described above, except that the cultures were incubated in complete medium for up to 8 hr before the addition of the warmed samples.

SDS-PAGE

Trichloroacetic acid (TCA) precipitation of proteins and SDS-PAGE were performed as described previously (Serafini et al, 1991).

Protein microsequencing

TCA precipitation: p78

A total of 11.75 ml from IMAC fractions (from three separate purification runs) containing p78 were made 0.015% in deoxycholate by the addition of 2% deoxycholate, and were precipitated in ten batches of no more than 1.25 ml in two 12×75 mm borosilicate glass tubes. To each 1.25 ml (or lower) volume was added an equal volume of 0.015% deoxycholate (to dilute the NaCl present in the fractions) and a two-thirds volume of 24% TCA. After incubation for 1 hr on ice, the precipitate was collected by centrifugation for 30 min at 3000 rpm (2060×g) in a GH-3.7 rotor (Beckman). The remaining batches were precipitated sequentially in the two tubes after removal of the supernatants. After the final precipitation, the pellets were resuspended by vigorous vortexing in 1 ml ice cold 6% TCA (to remove NaCl), and an additional 1 ml 6% TCA was used to wash pellet fragments down from the sides of the tube. The rinsed precipitate was collected by centrifugation as before, and the supernatants were aspirated. Deoxycholate and TCA were then removed by addition of 1 ml acetone (at −20° C.) and vortexing until the white precipitate was no longer apparent. The precipitated p78 was collected by centrifugation as before, the supernatants were aspirated, and the pellets were dried for 15 min at 37° C.

TCA precipitation: p75

To increase the amount of p75 available for microsequencing, fractions from two HSHP chromatography runs containing predominantly p75 (i.e., those three fractions in each HSHP run collected just before those pooled for the last purification step) were pooled, adjusted with 0.2M $NaH_2PO_4$, and chromatographed on the IMAC column as previously described. The p75 present in a total of 14.9 ml from IMAC fractions from four purification runs was TCA precipitated as described above for p78.

CNBr proteolysis

In order to obtain internal amino acid sequence from p78 and p75, peptides were generated by cyanogen bromide (CNBr) cleavage. The pellets of TCA precipitated protein were resuspended in 50 μl of a solution of 50 mg/ml CNBr in 70% formic acid, and were pooled and incubated overnight in the dark at ambient temperature. The formic acid was removed by evaporation in a SpeedVac (Savant). The residue was resolubilized in 50 μl deionized $H_2O$ and evaporated again to dryness in order to remove the remaining formic acid.

Gel electrophoresis and electroblotting

The CNBr-generated peptides were isolated essentially as described previously (Kennedy et al, 1988). The residue remaining after the final evaporation was solubilized in SDS-PAGE sample buffer containing 25 mM Tris base, loaded into a 1.5 cm well on a 1.5 mm thick, 20 cm long 15% polyacrylamide gel, and electrophoresed until the dye front just reached the bottom of the gel. Sodium thioglycolate (0.2 mM) was added to the electrophoresis buffer in the cathode chamber in order to scavenge free radicals remaining in the gel. Peptides were blotted onto a ProBlott membrane (Applied Biosystems) and visualized essentially as described (Matsudaira et al, 1987). Briefly, the gels were soaked for ten minutes in Transfer Buffer (10 mM 3-(cyclohexylamino)-1-propanesulfonic acid (CAPS) pH 11.0/ 10% methanol). ProBlott membranes were cut to size, wetted with 100% methanol, and equilibrated with Transfer Buffer. After assembly of the blotting sandwich, electroblotting was performed in a Bio-Rad Trans-Blot Cell at 1.0 A for 30 min at 4° C. Following transfer the blots were washed with deionized $H_2O$ for 5 min, stained for 5 min in 0.1% Coomassie Brilliant Blue R-250 in 50% methanol, and then destained with 50% methanol/10% acetic acid. After washing with water, the blots were air dried, and the peptide bands were excised and stored in 0.1% trifluoroacetic acid at −20° C. Prior to sequencing, the excised bands were feathered with a scalpel.

Protein sequencing

Peptide sequencing was performed on a Porton Instruments automated gas phase sequencer (Model PI 2020G) equipped with an on line analyzer for phenylthiohydantoin (PTH)-derivatized amino acids.

N-terminal protein sequencing

A volume of 0.6 ml (plus 0.4 ml water) p75-containing pooled IMAC fractions and 1 ml p78-containing IMAC fractions were separately TCA precipitated as described previously. After aspirating the acetone wash (and without any drying), the precipitated protein in each case was dissolved in 15 μl 70% formic acid and applied 3 μl at a time to a 2×5 mm piece of ProBlott membrane, allowing the membrane to dry between additions. The tubes were washed with an additional 15 μl 70% formic acid, which was then applied to the membranes. Sequencing was performed directly on these membrane pieces after feathering them.

N-terminal sequencing was also performed on impure p75/p78 subjected to SDS-PAGE and electroblotting as outlined above, with the p75 and p78 bands excised separately.

RNA isolation

Sixty-two E10 chick brains were dissected as described above and snap frozen in liquid nitrogen. Tissue was homogenized using a Polytron (Brinkmann) and total cellular RNA was isolated as described (Auffray and Rougeon, 1980). A total of 15.9 mg of total cellular RNA was obtained, a yield of 256 μg of total RNA per 0.22 g brain. RNA was isolated from total cellular RNA using oligo dT cellulose (Collaborative Research) as described (Ausubel et at., 1990). Seven and one-half mg of E10 chick brain RNA provided 353 μg poly(A)+ RNA, a yield of approximately 5%.

PCR generation of a fragment of the gene encoding p78

Twenty-five μg E10 chick brain poly(A)$^+$ RNA was reverse transcribed in a 100 μl reaction using 1000 U M-MLV (Gibco/BRL) under standard conditions (Ausubel et al, 1990). The RNA was heated to 95° C. for 5 min prior to its addition to a reaction mix lacking enzyme. Enzyme was added, and after 10 min at ambient temperature the reaction was incubated for 1 hr at 37° C. The reaction was then heated to 95° C. for 5 min and was quenched on ice and stored at −20° C.

Gel-purified, degenerate oligonucleotides designed from what were considered unambiguous stretches of amino acid sequence were used in two-stage nested PCR to obtain a fragment of the gene encoding p78. In the first stage reaction, the sense primer sequence was TAYGGNAARACNTGGGT (SEQ ID NO:01) (from the amino acid sequence YGKTWV (SEQ ID NOS:26/27, residues 168–173/139–144)) and the antisense primer sequence was GCYTCYTGYTCRTTYTG (SEQ ID NO:02) (from the amino acid sequence QNEQEA (SEQ ID NOS:26/27, residues 197–202/168–173)). In the second stage reaction, the sense primer sequence was TGGGTNCCNTTYCARTT (SEQ ID NO:03) (corresponding to the amino acid sequence WVPFQF (SEQ ID NO:26, residues 172–177)) and the antisense primer was that used in the first reaction. PCR was performed in a 50 μl reaction containing 1× PCR buffer (per Perkin Elmer Cetus), 0.1 mM dNTPs, 1 μM sense primer, 1 μM antisense primer, 2 μl cDNA synthesis reaction, and 0.5 μl (2.5 U) Taq DNA polymerase (Perkin Elmer Cetus). The second stage reaction was identical in composition except that the cDNA synthesis reaction was replaced by 1 μl of a 1:10 dilution of the first reaction. An MJ Research MiniCycler with temperature probe control was used for PCR. Taq polymerase was added after the samples had been brought to 92° C.; the cycling program for both reactions was 95° C. for 30 s, 37° C. for 30 s, increase by 1° C. every 5 s to 72° C., 72° C. for 1 min, and twenty-nine iterations of the cycle followed by 15 min at 72° C.

One half of the second PCR reaction was electrophoresed in a 1.5 mm thick 15% polyacrylamide minigel, and the single observed band of approximately 100 bp was excised and eluted in 100 μl H$_2$O over 7.5 hr in a 37° C. shaking incubator. The fragment was cloned into the pCRII vector using a TA-cloning kit (Invitrogen). Transformants were screened with PCR amplification across the cloning site, and four positive clones with 92 bp inserts were sequenced to yield 62 bp of unambiguous sequence of the gene encoding p78.

PCR general;ion of a fragment of the gene encoding p75

Two-stage nested PCR was also used to obtain a fragment of the gene encoding p75. The first stage consisted of four reactions, each having as sense primer the same degenerate oligonucleotide pool that was used in the first stage of cloning the p78 gene fragment, and having four different pools of degenerate oligonucleotides based on a single amino acid sequence (VCLNCR (SEQ ID NOS:26/27, residues 368–373/344–349)) as the antisense primer: (1) CKRCARTTNAGRCARAC, (SEQ ID NO:04) (2) CKRCARTYNAGRCAYAC, (3) (SEQ ID NO:05) CKRCARTTYAARCARAC, (SEQ ID NO:06) (4) CKRCARTTYAARCAYAC (SEQ ID NO:07). PCR was performed as described above except that 1 μl of a cDNA synthesis reaction was used, and the Taq polymerase was added after the reaction had been heated to 94° C. The temperature probe was not used to control the cycling program, which consisted of 97° C. for 1 min, X °C. for 1 min, 74° C. for 1 min, thirty-four more iterations of the cycle, followed by 74° C. for 20 min; "X" equalled 35, 40, 45, 50, 55, or 60. Twenty μl of each reaction was analyzed on a 2% agarose gel, and predominating in reactions using two of the four antisense pools (but present in all) was a product of approximately 630 bp that only appeared at the higher (more stringent) annealing temperatures, all of which would be expected for a bona fide p75 gene fragment. For each of the four reactions carried out with 55° C. annealing, this 630 bp product was electrophoresed into 0.8% low melting point agarose. The four second stage reactions were performed as were the first stage reactions, except that the input DNA consisted of 0.5 μl of melted low melting point agarose containing the 630 bp products, and the sense primer had the sequence TGGGTNCCNTAYCARTAYTA (SEQ ID NO:08) (corresponding to the amino acid sequence WVPYQYY (SEQ ID NO:27, residues 143–149)) while the antisense primer had the sequence GCRTGNCCRTTRCAYTTRCA (SEQ ID NO:09) (corresponding to the amino acid sequence CKCNGHA (SEQ ID NOS:26/27, residues 286–292/262–268)). In each case, a single band of approximately 380 bp was amplified. Fifteen μl from each of the reactions was combined, phenol/chloroform/isoamyl extracted, and the DNA precipitated. The isolated 380 bp product was digested with Sac I (which recognizes a site at this point in the gene for p78), and that small portion which remained uncut was isolated using Geneclean (Bio101), reamplified, redigested with Sac I, and cloned into the pCRII vector as described above. Transformants were screened with PCR across the cloning site, and two positives contained 377 bp inserts yielding 341 bp of unambiguous sequence of the gene encoding p75.

cDNA cloning

Library construction cDNA libraries, both oligo dT primed and specifically primed, were constructed using the ZAP cDNA Gigapack II Gold Cloning Kit (Stratagene) according to the manufacturer's instructions. cDNAs were size selected using a BRL cDNA size selection column in order to insure an insert size greater than 500 bp. In this way, an E10 chick brain cDNA library was constructed in the lambda ZAP vector using as starting material 5 μg of E10 chick brain poly(A)$^+$ RNA. For the isolation of 5' and 3' sequences, additional libraries were constructed using sequence specific first strand synthesis primers. Sequence obtained using 3' RACE (see below) was used to design a p78 oligonucleotide complimentary to sequence 3' of the translational stop codon with an attached 5' Xho I site, primer W1. Primer W1 was then used to prime the synthesis of first strand cDNA for a specific p78 library. Similarly, sequence 3' to the translational stop site in the p75 cDNA and sequence in the 5' end of the Clone 25 p75 cDNA were used to construct two primers, p75X1 and p75X2, to prime the first strand synthesis of cDNA libraries designed to obtain the missing 5' sequence of p75. cDNAs generated using sequence specific primers were cloned directly into Eco RI/Xho I digested pBluescript SK(+) vector (Stratagene).

3' RACE

Sequence corresponding to the 3' end of the p78 cDNA was amplified and cloned using the RACE protocol as described by Frohman and Martin (1989). The 3' poly(T) primer and primers $R_i$ and $R_o$ were used exactly as described, and the p78 specific 5' primers R5, R6, and R7 were used for nested PCR reactions. Vent DNA polymerase (New England Biolabs) was used for RACE reactions using the buffer provided by NEB and a final $MgSO_4$ concentration of 4 mM.

Probe design and synthesis

Probes used to screen the libraries were of two types: (1) random primed probes generated from gel-purified templates using a kit (Boehringer Mannheim) and (2) probes isotopically labelled by the incorporation of $a^{32}P$-dCTP during PCR. The reaction conditions for the amplification of a p78 61 bp probe (probe Z1) were as follows: Two µM each of primers p78o100 and p78o101; 50 µM dTTP, dATP, dGTP; 100 µCi $a^{32}P$-dCTP (17 pmoles at 6000 Ci/mM); 1× PCR buffer; and 2.5 U Taq DNA polymerase. For all PCR probe generation, the Taq polymerase was added after the reactions had been brought to the denaturation temperature. The amplification conditions were: (1) 95° C. for 30 s, (2) 60° C. for 30 s, (3) 72° C. for 30 s, with nine iterations of the program. The reaction conditions used to generate a p78 584 bp probe (probe Z2) were as follows: primers P1 and P2 each at 0.1 µM; 0.1 mM dATP, dTTP and dGTP; 3.4 µM dCTP; 200 µCi $a^{32}P$-dCTP (33 pmoles at 6000 Ci/mM); 1× PCR buffer; and 2.5 U Taq polymerase. The amplification conditions were: (1) 94° C. for 30 s, (2) 64° C. for 45 s, (3) 7220 C. for 1 min, with 24 iterations of the program. The reaction conditions used to generate a p75 258 bp probe (probe Z3) using primers Q3 and Q4 were the same as those for probe Z2 with the exception of using dCTP at 1.25 µM. Reaction conditions for probe Z4 synthesis were essentially as described above for probe Z2, but used the primers Q1 and Q2 to generate a 243 bp probe specific for p78. For a 5' p75 probe (probe Z5) synthesis, the reaction conditions were the following: primers OCM1 and OCM2 at 0.1 mM; 25 µM dATP, dGTP, dTTP; 2.5 µM dCTP; 100 µCi $a^{32}P$-dCTP (17 pmoles at 6000 Ci/mM); 1× Taq buffer; and 5 U Taq. The amplification conditions were as follows: (1) 94° C. for 30 s, (2) 48° C. for 40 s, (3) 72° C. for 40 s, with 24 iterations of the program.

Library screening

For screening, phage plaques or bacterial colonies were lifted onto duplicate filters (Hybond-N, Amersham), denatured and lyzed by autoclaving at 100° C. for 1 min, and the DNA UV crosslinked to the membrane. Before prehybridization the filters were washed in 1× SSC, 0.5% SDS to remove any residual protein. Probe was denatured before use at 95° C. for 5 minutes, and then chilled on ice or directly added hot to hybridization mixes.

Using probe Z1 at $1\times10^6$ cpm/ml, $1\times10^6$ clones of the E10 chick brain cDNA library were screened at high stringency (hybridization conditions: 6× SSC, 0.5% SDS, 2× Denhardt's, 100 µg/ml salmon sperm DNA at 55° C.; wash conditions: 1× SSC, 0.5% SDS at 55° C.). This initial screen identified a single internally primed 1 kb clone corresponding to p78, Clone 20. A second $1\times10^6$ clones were screened with probes Z2 and Z3. In this screen, the filters were again screened at high stringency (hybridization conditions: 6× SSC, 5× Denhardt's, 0.5% SDS, 100 µg/ml salmon sperm DNA at 65° C., wash conditions: 0.1× SSC, 0.1% SDS, 65° C.) with $1\times10^6$ cpm/ml of each probe. This second screen identified one cDNA corresponding to p78, Clone 29, and four cDNAs corresponding to p75: Clones 22, 25, 28, 34. The filters representing the $2\times10^6$ E10 chick brain clones were stripped and rescreened using probes (at $1\times10^6$ cpm/ml) randomly primed on gel isolated cDNAs of Clones 13, 25, and 29 using essentially the hybridization conditions described by Church and Gilbert (1980): prehybridization and hybridization in 500 mM $NaP_i$ pH 7.2, 1% SDS, 1 mM EDTA at 65° C., with washing in 40 mM $NaP_i$ pH 7.2, 1% SDS at 65° C. This screen identified an additional four partial p75 cDNAs. Three further cDNAs corresponding to p75, Clones 6, 7, and 9, were identified in a screen of an additional $1\times10^6$ clones of the E10 chick brain cDNA library using probe Z3 (at $1\times10^6$ cpm/ml) and Church hybridization conditions. An additional 1.7 kb p78 clone, Clone 13, was isolated by screening $2\times10^6$ lambda ZAP clones of an amplified E2.5 spinal cord cDNA library with probe Z4 using the above conditions. Phage were isolated and inserts excised in vivo and recirculatized into pBluescript II SK(−) as recommended by Stratagene.

Specifically primed cDNA libraries constructed in pBluescript were screened using Church conditions with probe Z4 or probe Z5, as appropriate, to identify clones containing cDNAs encoding the full coding sequences of p78 and p75.

Primers

| Primers | | | | | | | | |
|---|---|---|---|---|---|---|---|---|
| p78o100 | sense: | TCT | ACT | CCA | CGC | AGT | GCC | GC | (SEQ ID NO: 10) |
| p78o101 | antisense: | TGC | TTG | GTG | ATG | GCG | GCG | CG | (SEQ ID NO: 11) |
| Q1 | sense: | GTA | CAA | CAA | GCC | GAG | CCG | | (SEQ ID NO: 12) |
| Q2 | antisense: | AGT | CGT | CCT | CGT | TCT | C | | (SEQ ID NO: 13) |
| Q3 | sense: | TCT | ACG | GCA | AGC | CCA | GCA | AG | (SEQ ID NO: 14) |
| Q4 | antisense: | CGT | CCT | CCT | CGC | CAG | CCT | | (SEQ ID NO: 15) |
| P1 | sense: | ACC | TGA | CGT | GCT | GGC | AGT | CC | (SEQ ID NO: 16) |
| P2 | antisense: | CCG | TGT | TGT | GCT | TGC | AGT | CG | (SEQ ID NO: 17) |
| OCM2 | sense: | CCG | AGT | TCG | TCA | ACG | CC | | (SEQ ID NO: 18) |
| OCM1 | antisense: | CGT | TCT | AGA | TGC | CGT | TC | | (SEQ ID NO: 19) |
| R5 | sense: | CAA | AGC | CTC | CAA | GGG | GAA | GC | (SEQ ID NO: 20) |
| R6 | sense: | AGA | TCC | ACA | TCC | TGA | AAG | CG | (SEQ ID NO: 21) |
| R7 | sense: | ACA | AAC | AGG | GCA | GCA | ACC | GG | (SEQ ID NO: 22) |

W1, p78 primer for directed library synthesis:

AGA GAG AGA GAG AAC TAG TCT CGA GCT TCC ATC
CCT CAA TAC GAG            (SEQ ID NO:23)

p75X1, p75 primer for directed library synthesis:

AGA GAG AGA GAG AAC TAG TCT CGA GGT AGA GGT
CGG TGA GGC CAT (SEQ ID NO:24)

p75X2, p75 primer for directed library synthesis:

AGA GAG AGA GAG AAC TAG TCT CGA GTC CGT TCA
CAC GAT ATG TAT (SEQ ID NO:25)

DNA sequencing

Nested deletions for sequencing were generated using exo III digestion as described (Ausubel et al., 1990). Sequence was also obtained in some instances by subcloning small fragments or by using specific internal oligonucleotide primers. Dideoxysequencing was performed using the Sequenase kit (USB). In addition, sequence compressions were resolved by a combination of dITP sequencing (Sequenase USB) and Exo(–)PFU Cyclist DNA sequencing (Stratagene).

Oligonucleotide synthesis and purification

Oligonucleotides were synthesized using a Cyclone Plus DNA Synthesizer (Millipore). Oligonucleotides were polyacrylamide gel purified using standard methods (Sambrook at al., 1989).

Northern analysis

For Northern blot analysis, 1–5 µg of poly(A)$^+$ RNA from various chick tissues was denatured with formaldehyde, separated on a 1% agarose gel containing formaldehyde, and blotted to Hybond N (Amersham) as described (Sambrook et al., 1989). Probes were randomly primed from gel isolated p78 and p75 cDNA templates.

Southern analysis of genomic DNA

Chicken genomic DNA was isolated as follows (see Laird, et al, 1991): Seven E11 chick brains were dissected out and placed into 25 ml of 100 mM Tris-HCl pH 8.3, 5 mM EDTA, 0.2% SDS, 200 mM NaCl, 100 µg/ml proteinase K in a 50-ml conical tube; after 14.5 hr incubation at 55° C. with agitation, 25 µg DNase-free RNase A was added and the incubation continued for another 3 hr. The solution was centrifuged at 8310 rpm (10,000×g) in an SA-600 rotor at 4° C. for 15 min; supernatant was poured into an equal volume of 2-propanol and the tubes were mixed gently end-over-end. Genomic DNA was removed from the tube using a plastic pipette tip, and was dissolved in 2 ml TE overnight at 55° C., yielding 1.25 mg/ml DNA.

Ten µg genomic DNA was digested with 30 U Eco RI in 20 µl over a 5 hr period, electrophoresed in a 0.8% agarose gel, and then transferred to Hybond-N (Amersham) using standard conditions. The blot was probed sequentially with random-primed radiolabelled probes made with Clone 13 (for p78) and Clone 25 (for p75) as templates using hybridization conditions described by Church and Gilbert (1980).

In situ hybridization

In situ hybridization was performed essentially as described in Ausubel et at., eds. (1990).

Expression of recombinant p78 and p75

Sequences encoding the entire coding region of either p78 or p75 in an Eco RI/Xho I fragment are subcloned into the COS cell expression vector pcDNA1 (Invitrogen) yielding the plasmids p78EXC1 (for p78) and p75EXC2 (for p75). Early passage COS cells are seeded at $2.5 \times 10^5$ cells per 35 mm well in six-well plates, and are transfected approximately 18–20 hr later with 1 µg p78EXC1 or p75EXC2 DNA (prepared by PEG precipitation) using 6 µl Lipofectamine (Gibco/BRL) according to the manufacturer's instructions. Complete medium (DME-H21) is conditioned for at least 24 h in order to accumulate expressed protein. At the end of the conditioning period, medium and cells are harvested, and the cells are extracted with 1M NaCl to extract adsorbed recombinant protein. Recombinant protein is purified through methods based on the established purification of the proteins from embryonic chick brain.

Recombinant protein is also obtained using a baculovirus expression system (Ausubel, 1990), and is purified as described above.

REFERENCES CITED IN EXAMPLES

Auffray, C., and Rougeon, F., (1980) Purification of mouse immunoglobulin heavy-chain messenger RNAs from total myeloma tumor RNA. *Eur. J. BioChem.* 107: 303–314.

Ausubel, F. M., Brent, R., Kingston, R. E., Moore, D. D., Seidman, J. G., Smith, J. A., Struhl, K., eds. (1990) *Current protocols in molecular biology.* Greene Publishing Associates and Wiley-Interscience.

Calof, A. L., and Lander, A. D. (1991). Relationship between neuronal migration and cell-substratum adhesion: laminin and merosin promote olfactory neuronal migration but are anti-adhesive. *J. Cell Biol,* 115: 779–794.

Church, G. M. and Gilbert, W. (1984) Genomic Sequencing. *Proc. Natl. Acad. Sci. USA* 81: 1991–1995.

Cooke, R. M., Wilkinson, A. J., Baron, M., Pastore, A., Tappin, M. J., Campbell, I. D., Gregory, H., and Sheard, B. (1987). The solution structure of human epidermal growth factor. *Nature* 327: 339–341.

Engel, J. (1989). EGF-like domains in extracellular matrix proteins: localized signals for growth and differentiation? *FEBS Letters* 251: 1–7.

Frohman, M. A., and Martin, G. R. (1989) Rapid amplification of cDNA ends using nested primers. *Technique* 1: 165–170.

Kennedy, T. E., Gawinowicz, M. A., Barzilai, A., Kandel, E. R., and Sweatt, J. D. (1988a). Sequencing of proteins from two-dimensional gels using in situ digestion and transfer of peptides to polyvinylidene difluoride membranes: Application to proteins associated with sensitization in Aplysia. *Proc. Natl. Acad. Sci. USA* 85: 7008–7012.

Kleinman, H. K., Weeks, B. S., Schnaper, H. W., Kibbey, M. C., Yamamura, K., and Grant, D. S. (1993). The laminins: a family of basement membrane glycoproteins important in cell differentiation and tumor metastases. *Vitamins and Hormones* 47: 161–187.

Laird, P. W., Zijderveld, A., Linders, K., Rudnicki, M. A., Jaenisch, R., and Berns, A. (1991). Simplified mammalian DNA isolation procedure. *Nucl. Acids Res.* 19: 4293.

Massagué, J. (1991). A helping hand from proteoglycans. *Curr. Biol.* 1: 117–119.

Matsudaira, M. P. (1987). Sequence from picomole quantities of proteins electroblotted onto polyvinylidene difluoride membranes. *J. Biol. Chem.* 262: 10035–10038.

Placzek, M., Tessier-Lavigne, M., Jessell, T., and Dodd. J. (1990a). Orientation of commissural axons in vitro in response to a floor plate-derived chemoattractant. *Development* 110: 19–30.

Placzek, M., Tessier-Lavigne, M., Yamada, T., Dodd, J. and Jessell, T. M. (1990b). Guidance of developing axons by diffusible chemoattractants. *Cold Spring Harbor Symposia on Quantitative Biology* 55: 279–302.

Sambrook, J., Fritsch, E. F., Maniatis, T. (1989). *Molecular cloning: a laboratory manual.*, 2nd ed. Cold Spring Harbor Lab., New York.

Serafini, T., Stenbeck, G., Brecht, A., Lottspeich, F., Orci, L., Rothman, J. E., and Wieland, F. T. (1991). A coat subunit of Golgi-derived non-clathrin-coated vesicles with homology to the clathrin-coated vesicle coat protein b-adaptin. *Nature* 349:215–220.

Tessier-Lavigne, M., Placzek, M., Lumsden, A. G. S., Dodd, J., and Jessell, T. M. (1988). Chemotropic guidance of developing axons in the mammalian central nervous system. *Nature* 336: 775–778.

von Heijne, G. (1986). A new method for predicting signal sequence cleavage sites. *Nucl. Acids Res.* 14: 4683–4690.

Walter, J. et al (1987). Recognition of position-specific properties of tectal cell membranes by retinal axons in vitro. *Development* 101: 685–96.

Yurchenco, P. D. and Cheng, Y.-S. (1993). Self-assembly and calcium-binding sites in laminin. *J. Biol. Chem.* 268: 17286–17299.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated nucleic acid encoding a vertebrate netrin polypeptide wherein said nucleic acid
   (a) encodes a vertebrate nettin polypeptide selected from the group consisting of SEQ ID NO: 26, SEQ ID NO: 27, and SEQ ID NO: 40,
   (b) is selected from the group consisting of SEQ ID NO: 41, SEQ ID NO: 42, and SEQ ID NO: 43, or
   (c) hybridizes under low stringency conditions to a nucleic acid selected from the group consisting of SEQ ID NO: 41, SEQ ID NO: 42, and SEQ ID NO: 43 and wherein the encoded nettin either selectively increases spinal axon outgrowth or directs spinal outgrowth orientation and wherein the encoded nettin is a naturally occurring vertebrate homolog of the nettin polypeptides of SEQ ID NOS: 26, 27, or 40.

2. An isolated nucleic acid of claim 1 which encodes a vertebrate netrin polypeptide selected from the group consisting of SEQ ID NO: 26, SEQ ID NO: 27, and SEQ ID NO: 40.

3. An isolated nucleic acid of claim 2 selected from the group consisting of SEQ ID NO: 41, SEQ ID NO: 42, and SEQ ID NO: 43.

4. An isolated nucleic acid of claim 1 that hybridizes under low stringency conditions to a nucleic acid selected from the group consisting of SEQ ID NO: 41, SEQ ID NO: 42, and SEQ ID NO: 43 and wherein the encoded netrin either selectively increases spinal axon outgrowth or directs spinal outgrowth orientation and wherein the encoded netrin is a naturally occurring vertebrate homolog of the netrin polypeptides of SEQ ID NOS: 26, 27, or 40.

5. An isolated nucleic acid of claim 4 wherein the encoded netrin is a mammalian homolog.

6. An isolated nucleic acid of claim 5 wherein the encoded netrin is a human homolog.

7. An isolated nucleic acid of claim 4 wherein the encoded netrin contains at least one amino acid sequence selected from the group consisting of
   (a) amino acid residues 289–294 of SEQ ID NO: 26,
   (b) amino acid residues 296–304 of SEQ ID NO: 26,
   (c) amino acid residues 308–315 of SEQ ID NO: 26,
   (d) amino acid residues 320–338 of SEQ ID NO: 26,
   (e) amino acid residues 345–350 of SEQ ID NO: 26,
   (f) amino acid residues 352–368 of SEQ ID NO: 26,
   (g) amino acid residues 373–380 of SEQ ID NO: 26,
   (h) amino acid residues 385–401 of SEQ ID NO: 26,
   (i) amino acid residues 408–416 of SEQ ID NO: 26,
   (j) amino acid residues 418–423 of SEQ ID NO: 26,
   (k) amino acid residues 427–434 of SEQ ID NO: 26,
   (l) amino acid residues 439–451 of SEQ ID NO: 26, and
   (m) amino acid residues 272–280 of SEQ ID NO: 27.

8. An isolated cell comprising the isolated nucleic acid of claim 1.

9. A process for the production of a vertebrate netrin polypeptide comprising culturing the isolated cell of claim 8 under conditions suitable for the production of said polypeptide and recovering said polypeptide.

* * * * *